US012201528B2

(12) United States Patent
Whitman et al.

(10) Patent No.: US 12,201,528 B2
(45) Date of Patent: Jan. 21, 2025

(54) SYSTEMS AND METHODS FOR MINIMALLY INVASIVE ANNULOPLASTY

(71) Applicant: Micro Interventional Devices, Inc., Newtown, PA (US)

(72) Inventors: Michael P. Whitman, New Hope, PA (US); Peter Datcuk, Quakertown, PA (US)

(73) Assignee: MICRO INTERVENTIONAL DEVICES, INC., Newtown, PA (US)

( * ) Notice: Subject to any disclaimer, the term of this patent is extended or adjusted under 35 U.S.C. 154(b) by 0 days.

(21) Appl. No.: 18/492,809

(22) Filed: Oct. 24, 2023

(65) Prior Publication Data
US 2024/0065838 A1   Feb. 29, 2024

Related U.S. Application Data

(63) Continuation of application No. 17/072,002, filed on Oct. 15, 2020, now Pat. No. 11,826,254.
(60) Provisional application No. 62/915,176, filed on Oct. 15, 2019.

(51) Int. Cl.
*A61F 2/24* (2006.01)
*A61B 17/04* (2006.01)
*A61B 17/00* (2006.01)

(52) U.S. Cl.
CPC ........ *A61F 2/2466* (2013.01); *A61B 17/0469* (2013.01); *A61B 2017/00367* (2013.01); *A61B 2017/00398* (2013.01); *A61F 2220/0008* (2013.01); *A61F 2220/0016* (2013.01)

(58) Field of Classification Search
CPC ............ A61F 2/2466; A61F 2220/0008; A61F 2220/0016; A61B 17/0469; A61B 2017/00367; A61B 2017/00398
See application file for complete search history.

(56) References Cited

U.S. PATENT DOCUMENTS

| 7,452,327 | B2 | 11/2008 | Durgin et al. |
| 8,216,272 | B2 | 7/2012 | Shipp |
| 9,364,235 | B2 | 6/2016 | Ranucci et al. |
| 2005/0251175 | A1 | 11/2005 | Weisenburgh, II et al. |
| 2006/0271074 | A1 | 11/2006 | Ewers et al. |

(Continued)

FOREIGN PATENT DOCUMENTS

WO   2017/100211   6/2017

OTHER PUBLICATIONS

International Search Report and Written Opinion Issued On Jan. 14, 2021 In Corresponding PCT Application No. PCT/US2020/055861.

(Continued)

*Primary Examiner* — Phong Son H Dang
(74) *Attorney, Agent, or Firm* — DUANE MORRIS LLP

(57) ABSTRACT

An apparatus for deploying a tissue anchor is disclosed. The apparatus includes a catheter tube having a proximal end and a distal end defining the catheter's length, where the distal end has an anchor housing configured to hold a tissue anchor before deployment; and a pusher wire positioned within the catheter tube and extending through the length of the catheter tube. The apparatus is configured to provide a pushing force on the pusher wire from the proximal end of the catheter tube, thus displacing the pusher wire in a distal direction to the pusher wire's fully extended anchor deployment position which in turn deploys the tissue anchor from the anchor housing in the distal direction by pushing the tissue anchor in the distal direction.

5 Claims, 70 Drawing Sheets

(56) References Cited

U.S. PATENT DOCUMENTS

| | | |
|---|---|---|
| 2010/0121355 A1 | 5/2010 | Gittings et al. |
| 2012/0029538 A1 | 2/2012 | Reeser |
| 2012/0253392 A1 | 10/2012 | Bentley et al. |
| 2013/0012961 A1 | 1/2013 | Reeser |
| 2014/0316458 A1 | 10/2014 | Whitman et al. |
| 2015/0320413 A1 | 11/2015 | Gittings et al. |
| 2016/0095704 A1 | 4/2016 | Whitman |
| 2017/0189061 A1 | 7/2017 | Weisbrod et al. |
| 2018/0116800 A1 | 5/2018 | Alon |
| 2018/0153550 A1 | 6/2018 | Souls et al. |
| 2019/0008504 A1 | 1/2019 | Stiggelbout |
| 2019/0307331 A1 | 10/2019 | Saadat et al. |
| 2020/0015922 A1 | 1/2020 | Cauldwell et al. |
| 2022/0401214 A1 | 12/2022 | Saul |

OTHER PUBLICATIONS

Extended European Search Report Issued Sep. 10, 2023 In Corresponding European Patent Application No. 20877514.8.

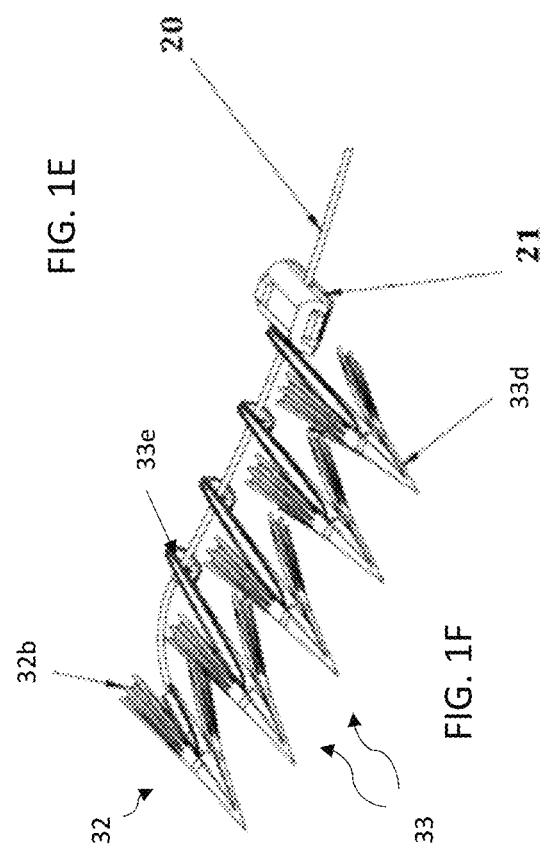

SECTION A-A

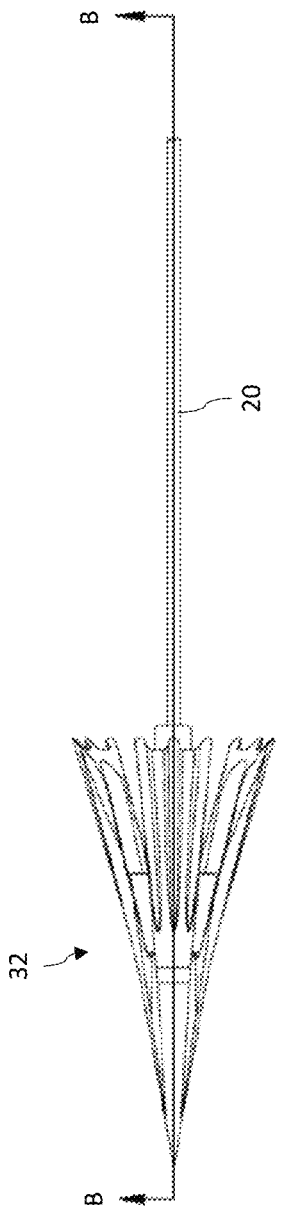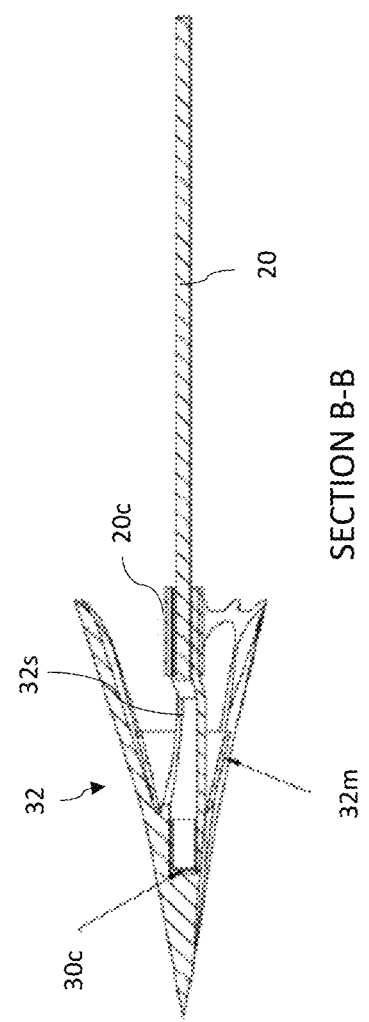
FIG. 3A
SECTION B-B
FIG. 3B

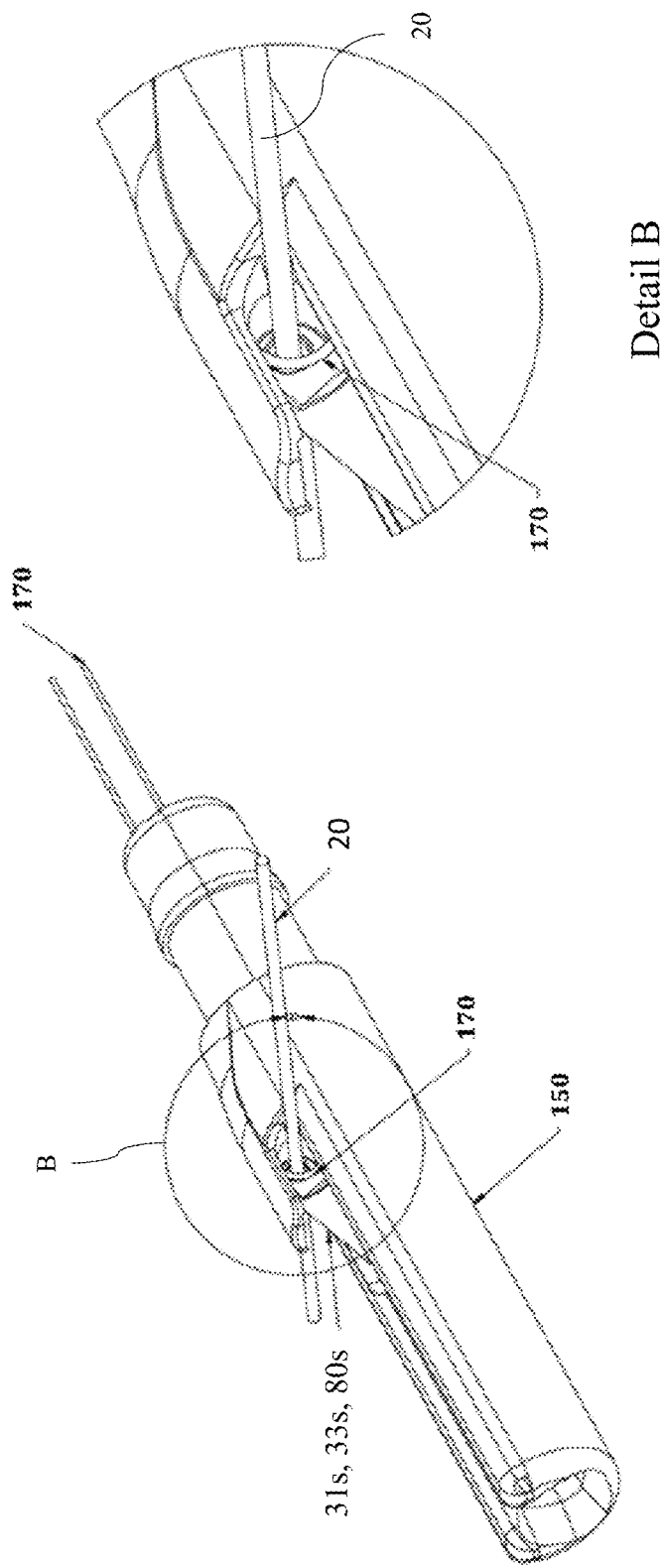

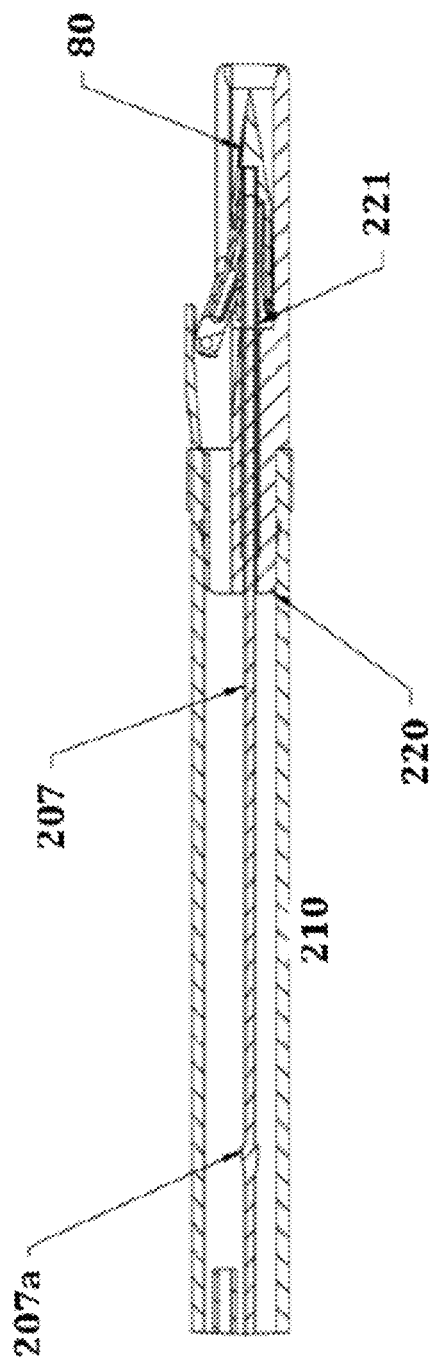

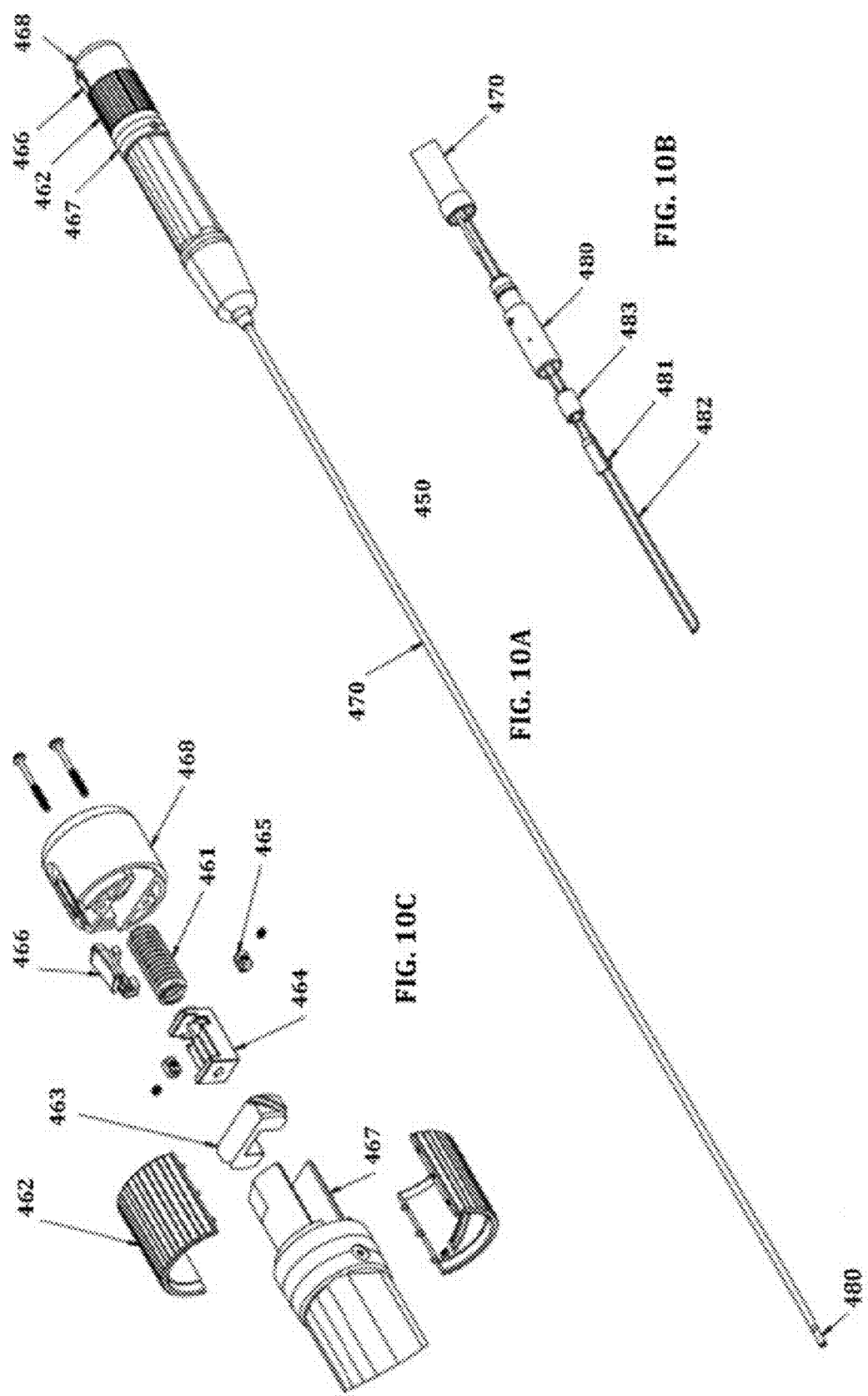

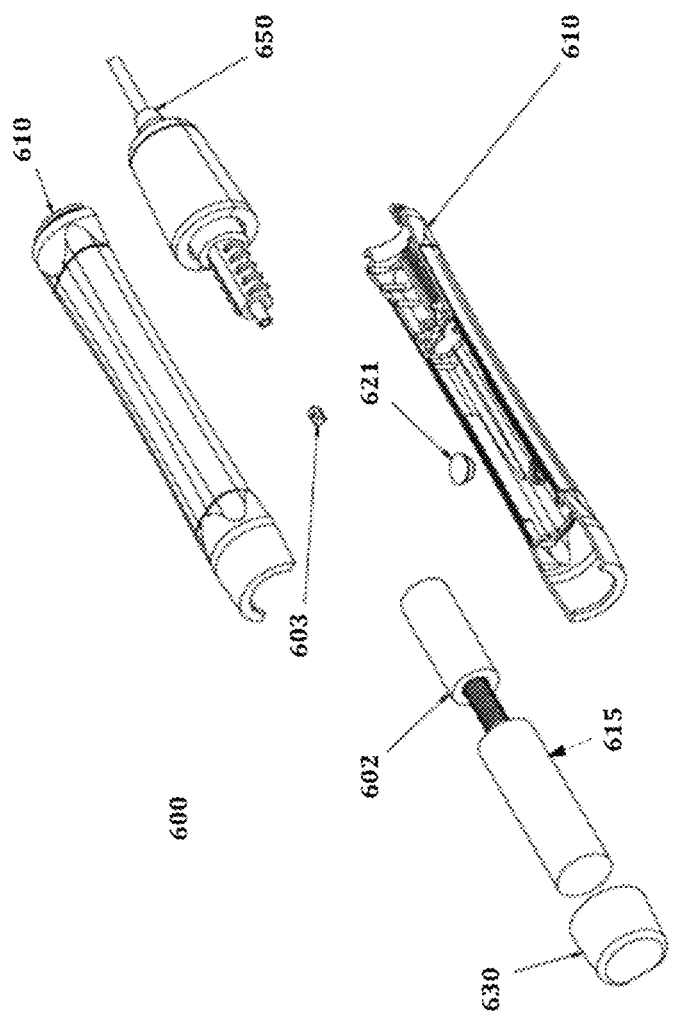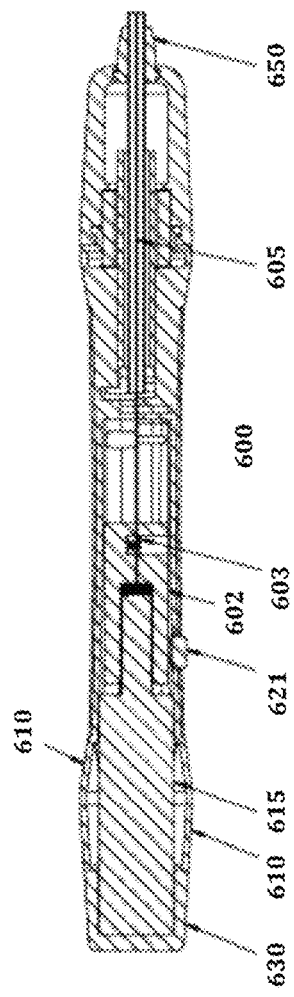

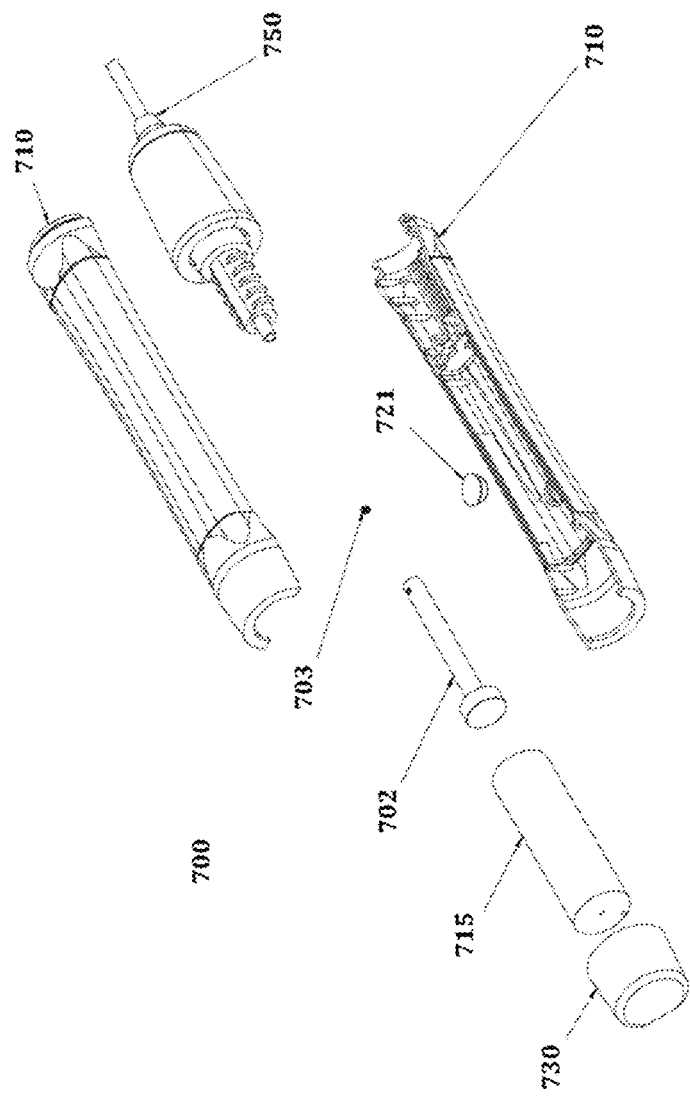
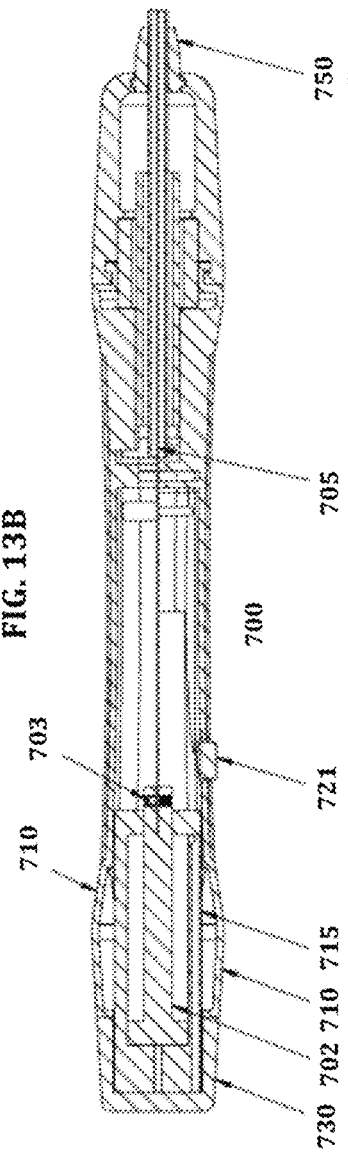
FIG. 13A
FIG. 13B

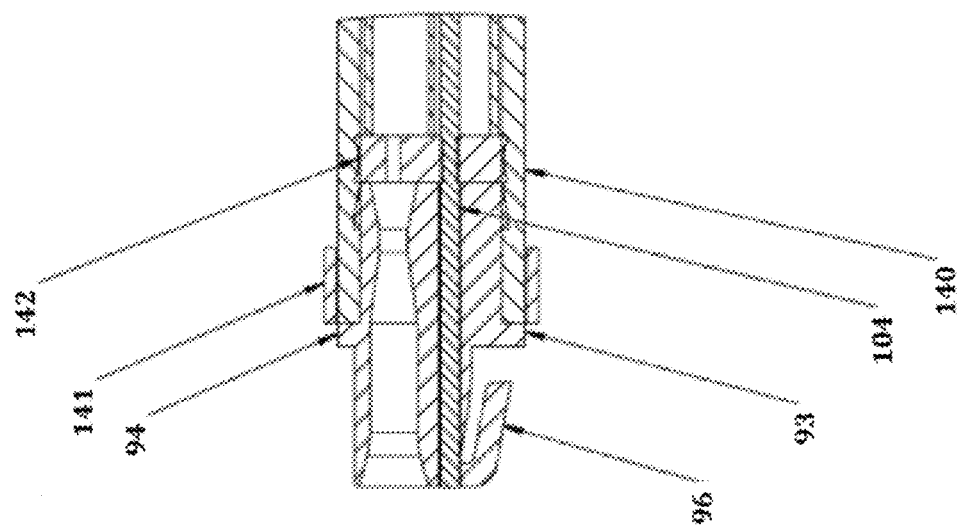
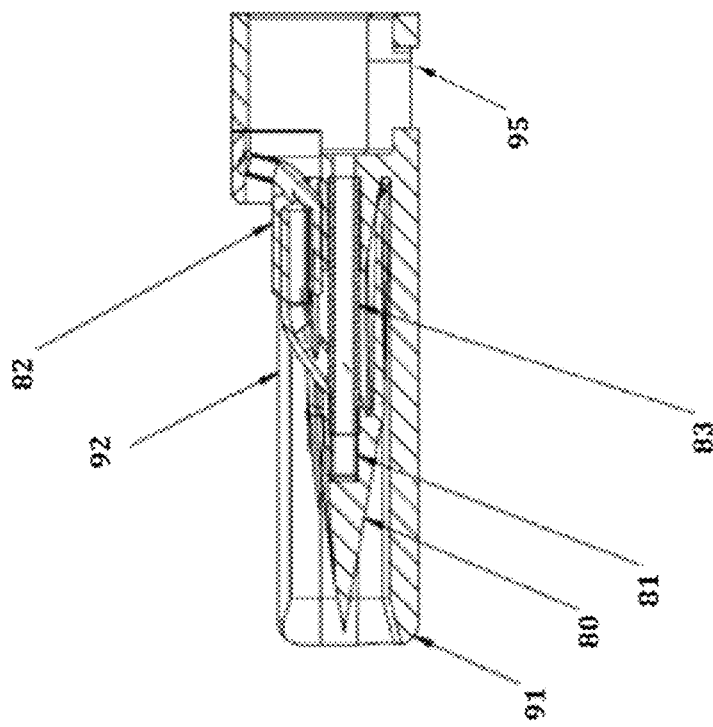
FIG. 16A

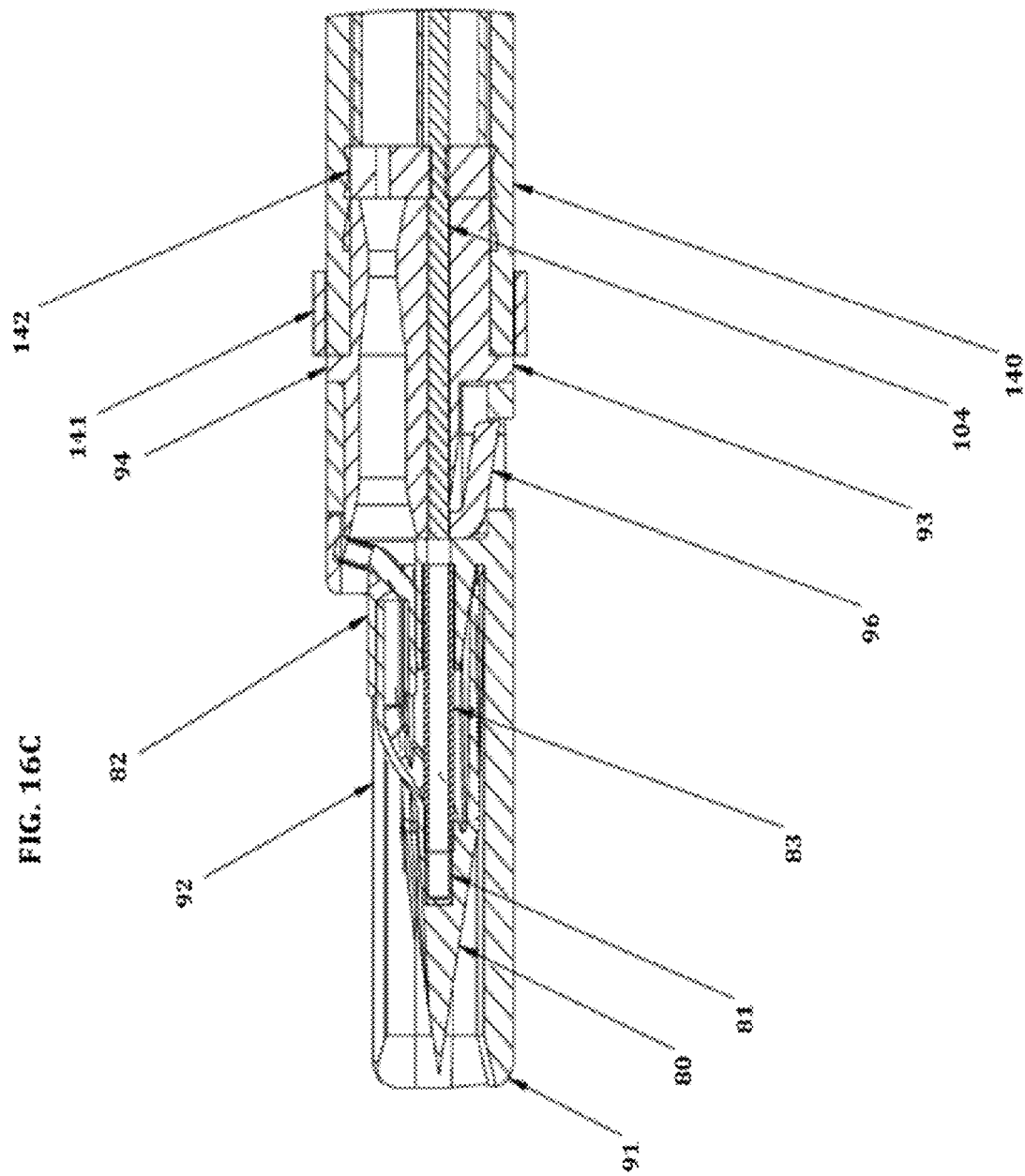

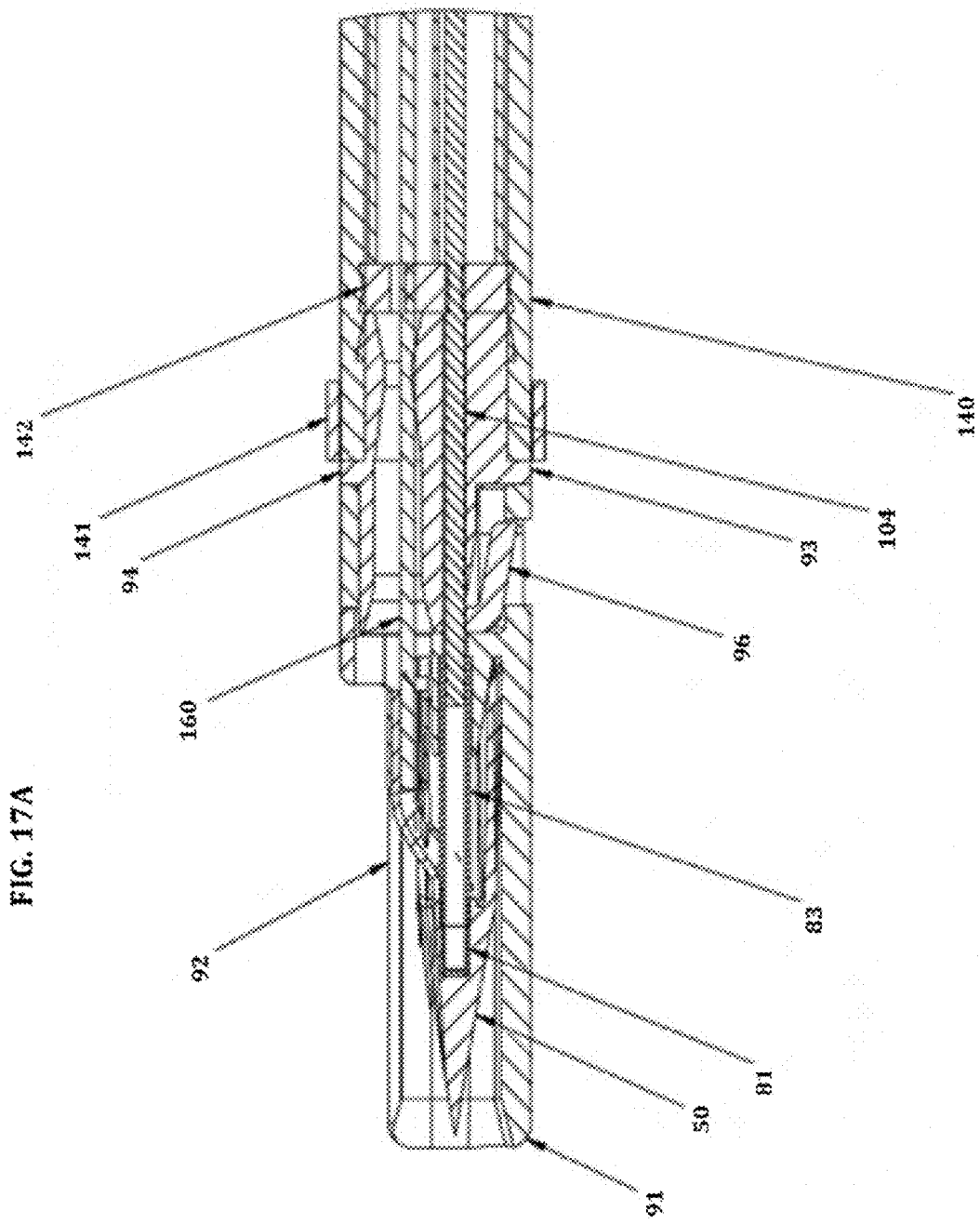

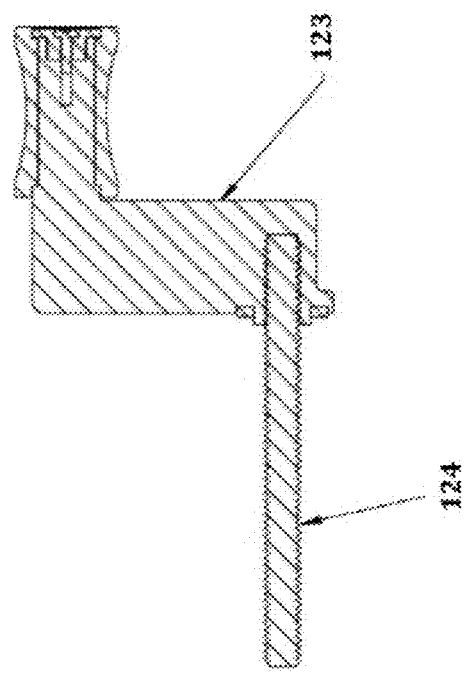
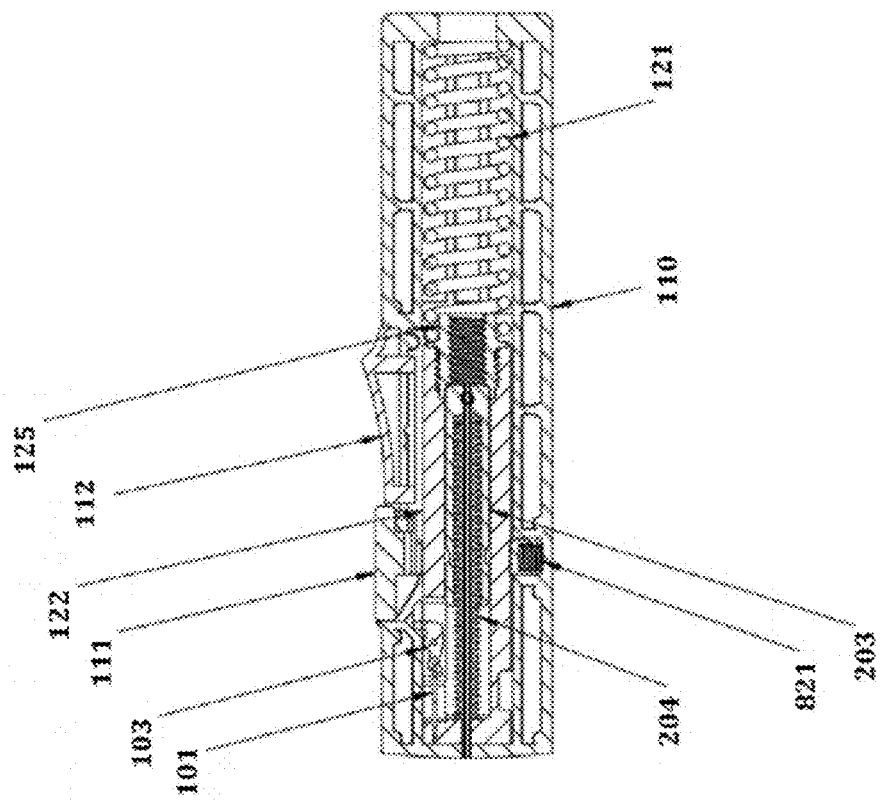
FIG. 18A

SYSTEMS AND METHODS FOR MINIMALLY INVASIVE ANNULOPLASTY

CROSS-REFERENCE TO RELATED APPLICATIONS

This application is a continuation of U.S. patent application Ser. No. 17/072,002, filed on Oct. 15, 2020, the entire contents of which is incorporated herein by reference.

FIELD OF THE INVENTION

The present invention relates to systems and devices for percutaneously carrying out minimally-invasive surgical intervention.

BACKGROUND

The treatment of tricuspid and mitral valves is well documented. Surgical procedures have been in existence for over 70 years and are well documented in textbooks such as Carpentier's Reconstructive Valve Surgery, Sanders 1957. While these treatments are effective in reducing regurgitation, they are generally very invasive procedures requiring anesthesia and surgical intervention. Advances in percutaneous structural heart disease treatments such as transcatheter aortic valve implantation (TAVI) have greatly advanced the standard of care for these diseases. TAVI is rapidly becoming the standard of care as this percutaneous procedure has obviated the need for surgical intervention. Interventional percutaneous approaches have the benefit of accessing the heart through the circulatory system, eliminating the need for surgical incisions, general anesthesia and the comorbidities associated with such. Specifically, tricuspid and mitral diseases generally fall into one of two categories: functional disease and degenerative disease. No effective percutaneous interventional procedures currently exist to address these disease states. For instance, the treatment of tricuspid and mitral valve disease requires that the patient be under general anesthesia, have a sternotomy or other access to the heart, catheters placed in the heart, the heart placed on bypass, and direct visualization gained through surgical access. There are a number of comorbidities associated with this access and recovery from bypass. There is a need for a percutaneous approach to the treatment of diseases as the improvement of patient recovery and long-term efficacy are well documented.

SUMMARY

In accordance with example embodiments of the present invention, systems for transcatheter tricuspid and mitral valve interventions are provided.

Example embodiments of the present invention include a percutaneous device that delivers low mass anchors to the annulus of either the tricuspid and/or mitral valve forming a fixation point, allowing for the reconfiguration of the annulus (i.e., annuloplasty). The anchors are connected by a suture or other material that allows for the anchors to be drawn into apposition and secured utilizing a lock. Once the anchors are drawn into a position such that the structure will enable reduced regurgitation and restructuring of the valve, the lock is applied to fix the anchors in position.

Provided is an apparatus for deploying a tissue anchor comprising: a catheter tube having a proximal end and a distal end defining the catheter's length, wherein the distal end comprising an anchor housing configured to hold a tissue anchor before deployment; and a pusher wire positioned within the catheter tube and extending through the length of the catheter tube, wherein the pusher wire has a proximal end and a distal end corresponding with the proximal end and the distal end of the catheter tube, wherein the apparatus is configured to provide a pushing force on the pusher wire from the proximal end of the catheter tube, thus displacing the pusher wire in a distal direction to the pusher wire's fully extended anchor deployment position which in turn deploys the tissue anchor from the anchor housing in the distal direction by pushing the tissue anchor in the distal direction.

BRIEF DESCRIPTION OF THE DRAWINGS

Further features and aspects of example embodiments of the present invention are described in more detail below with reference to the appended figures. All figures are schematic are not intended to show actual dimensions.

FIG. 1E shows an overhead view of the anchors according to an exemplary embodiment of the present invention.

FIG. 1F shows an overhead view of the anchors and suture lock according to an exemplary embodiment of the present invention.

FIGS. 3A-3C show an anchor for use in the anchor deployment mechanism of FIG. 1A in accordance with an example embodiment of the present invention.

FIGS. 6A-6C show a distal anchor housing of the anchor deployment mechanism in FIG. 1A in accordance with an example embodiment of the present invention.

FIGS. 7A-7B show an anchor deployment mechanism in accordance with an example embodiment of the present invention.

FIG. 10A shows another configuration of an suture cutting mechanism in accordance with an example embodiment of the present invention.

FIG. 10B shows a distal anchor housing of the suture cutting mechanism of FIG. 10A.

FIG. 10C shows an exploded view of the suture cutting mechanism of FIG. 10A.

FIG. 12A shows an exploded view of an anchor deployment mechanism in accordance with an example embodiment of the present invention.

FIG. 12B shows a cross sectional view of the anchor deployment mechanism of FIG. 11A.

FIG. 13A shows an exploded view of an anchor deployment mechanism in accordance with an example embodiment of the present invention.

FIG. 13B shows a cross sectional view of the anchor deployment mechanism of FIG. 11A.

FIG. 16A shows a cross sectional view of the anchor deployment mechanism in accordance with an example embodiment of the present invention.

FIG. 16C shows a cross sectional view of the anchor deployment mechanism in accordance with an example embodiment of the present invention.

FIG. 17A shows a cross sectional view of the anchor deployment mechanism in accordance with an example embodiment of the present invention.

FIG. 18A shows a cross sectional view of the anchor deployment mechanism in accordance with an example embodiment of the present invention.

DETAILED DESCRIPTION

As set forth in greater detail below, example embodiments of the present invention allow for the reliable and effective percutaneous intervention in heart tissue that limits the possibility of human error, e.g., by quickly and reliably deploying surgical anchors by simple user operation. In some examples, two or more surgical anchors are driven into tissue in succession, with the possibility of being connected to each other by one or more sutures. The anchors are driven in succession to permit the anchors to be driven into the tissue at different locations while remaining connected by one or more sutures, and then drawn together to bring the affected tissue into apposition. As applied to, for example, a failing heart valve experiencing heart valve regurgitation, drawing together the heart valve tissue can repair the heart valve to proper healthy operation.

Figure 1A:
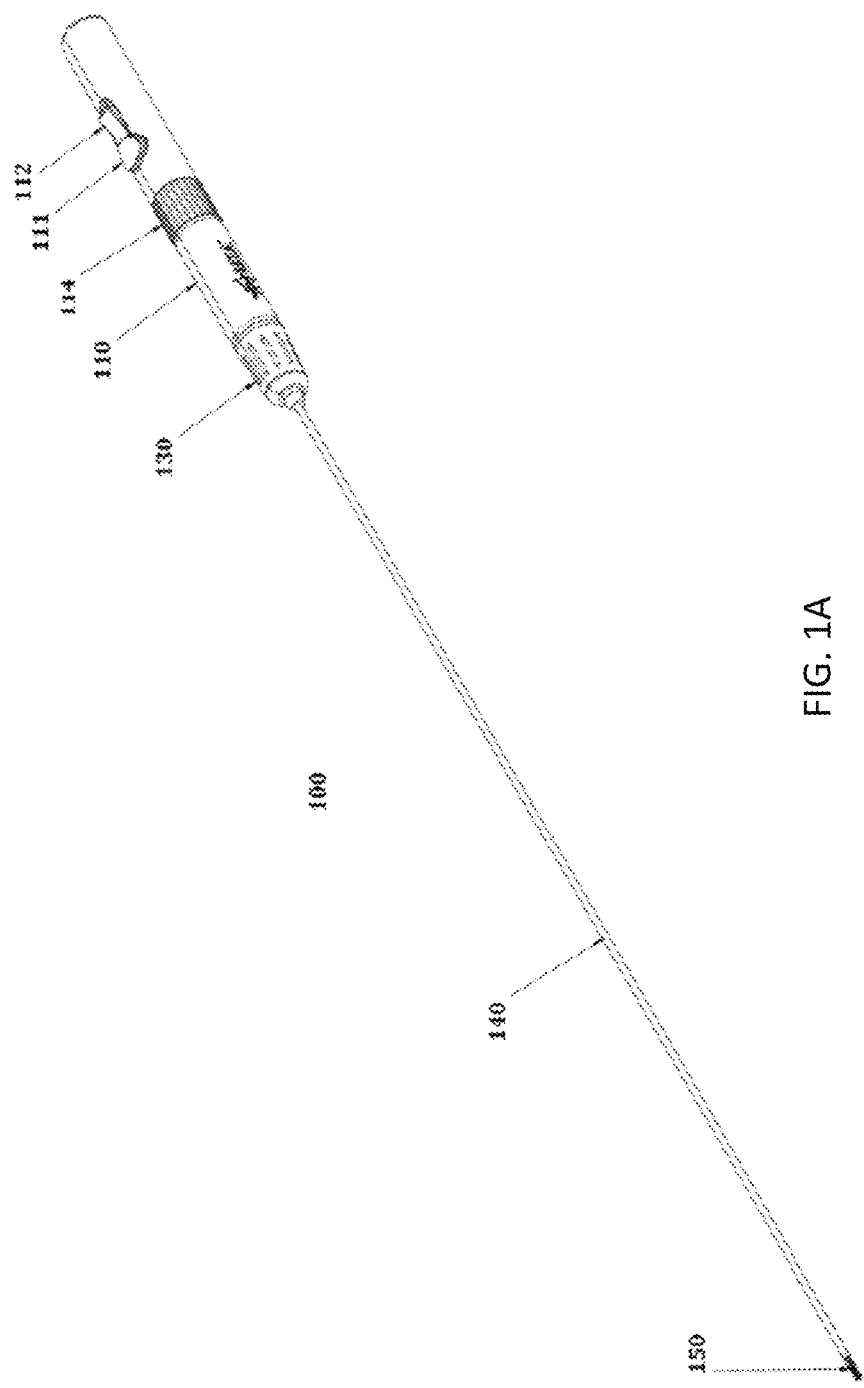
FIG. 1A shows an anchor deployment mechanism in accordance with an example embodiment of the present invention.

FIG. 1A shows an anchor deployment mechanism 100 in accordance with an example embodiment of the present invention. As depicted in FIG. 1A, anchor deployment mechanism 100 can include a handle 110, a release button 111, a safety button 112, stabilization pin control knob 114, deflection knob 130, a catheter tube 140, and a distal anchor housing 150.

Figure 1B:
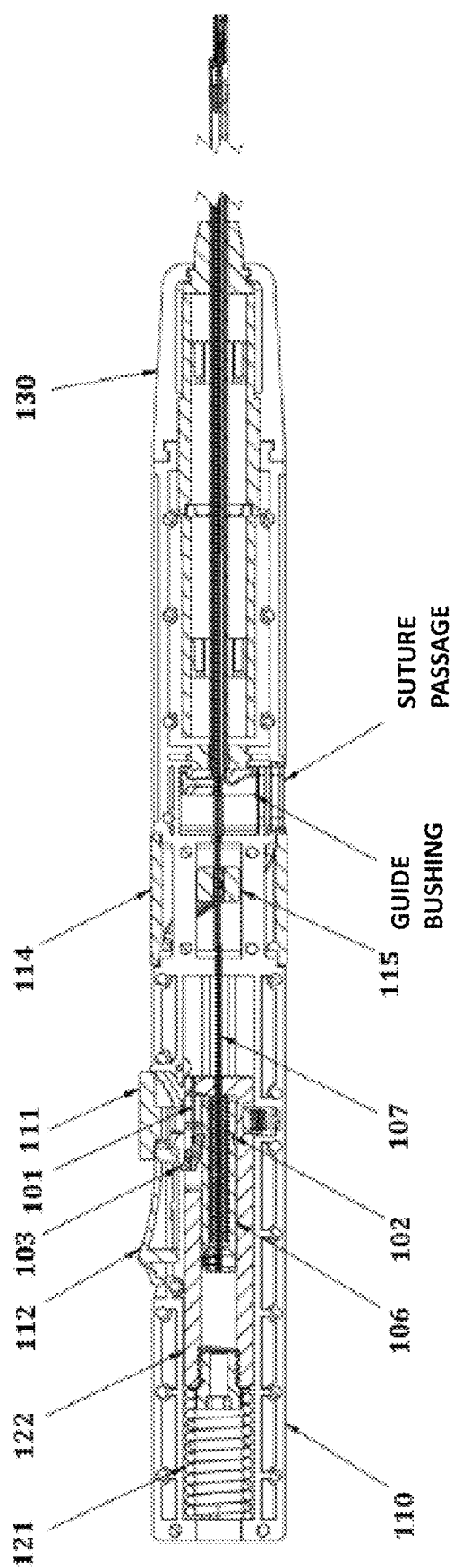
FIG. 1B shows a cross-sectional view of the anchor deployment mechanism of FIG. 1A in accordance with an example embodiment of the present invention.

FIG. 1B is a cross-sectional view of the anchor deployment mechanism of FIG. 1A. As depicted in FIG. 1B, the anchor deployment mechanism may also include a pawl spring 101, a ratchet 102, a pawl 103, ratchet housing 106, a pusher wire 107, a compression spring 121 and a pusher 122. In an example embodiment, the elements within the handle 110 are configured to impart a pushing force on anchors located in the distal anchor housing 150. For example, if the safety button 112 is maintained in an "off" position, a user can selectively initiate the transfer of a pushing force from the compression spring 121 in a compressed state to the anchors by engaging the release button 111. Specifically, when the release button 111 is engaged (e.g., pressed), the release button disengages from a slot in the pusher 122, allowing the compressed spring 121 to decompress and exert a pushing force in the distal direction. In an example embodiment, the pushing force from the decompression of the compressed spring 121 is transmitted to the anchors via guide and pusher wire 107 in the handle 110. In another example embodiment, the pushing force exerted on the anchors may be imparted by other electrical, mechanical, pneumatic, or hydraulic operation. For example, an electrical operation can be applied to create an electrical pushing force, via an electrical linear actuator. As a further example, a mechanical operation can be applied to create a mechanical pushing force, via a motorized or geared actuator. As a further example, a pneumatic or hydraulic operation can be applied via a compressed carbon dioxide (or a similar gas) cartridge housed in the handle of the device, or a fluid, and selectively opening the cartridge to expel the gas or fluid into a cylindrical chamber to drive the pusher wire.

FIG. 1B further illustrates a stabilization pin control knob 114 for deploying stabilization pins 151 (see FIGS. 2C-2F) from the distal end of the device. Stabilization pin control knob 114 may be coupled to a stabilization pin control screw 115, such that turning of the stabilization pin control knob 114 imparts a force on the stabilization pin control screw 115 to drive the screw in proximal or distal directions. By moving the stabilization pin control screw 115 in the distal direction, stabilization pins 151 may be pushed to extend beyond the distal end of the device, as shown in FIGS. 2D-2F.

Figure 1C:
FIG. 1C shows an overhead view of anchors according to an exemplary embodiment of the present invention.

FIG. 1C shows an array of anchors connected via a tensioning element, the suture 20, in accordance with an example embodiment. In an example embodiment, the array comprises a primary anchor 30 and a plurality of secondary anchors 31. The primary anchor 30 is the first one in the array that gets placed or anchored into the target tissue in the patient and is attached to the terminal end of the suture 20. The secondary anchors 31 are the anchors that get anchored into the target tissue in the patient subsequently. Each of the anchors 30 and 31 includes a distal end 30d and 31d, respectively, and a stem 30s and 31s, respectively, extending proximally from the distal end. Further, the proximal ends of the stems of the secondary anchors 31 include an eyelet 31e. The suture 20 whose terminal end is connected to the primary anchor 30 is threaded through the eyelets 31e of the secondary anchors 31 thus connecting the secondary anchors 31 in series behind the primary anchor 30.

In an example embodiment, each of the primary and secondary anchors 30 and 31 can also include a plurality of corrugated wings or barbs 30b and 31b, respectively, that extend proximally and radially outward from the distal ends 30d, 31d of the respective anchors, and, in an example embodiment, are radially flexible with respect to the distal ends, so that the wings or barbs 30b, 31b can be compressed towards the stems or extended radially outward. Further, in the illustrated examples shown in FIGS. 1C and 1D, the distal ends 30d, 31d of each of the primary and secondary anchors 30 and 31 are hollow.

Further, as depicted in the figure, the suture 20 can be attached to the primary anchor 30 and connected to a plurality of secondary anchors 31 via the respective eyelets 30e, 31e. In an example embodiment, the eyelets 30e, 31e allow the secondary anchors 31 to slide along the suture 20.

Figure 1D:
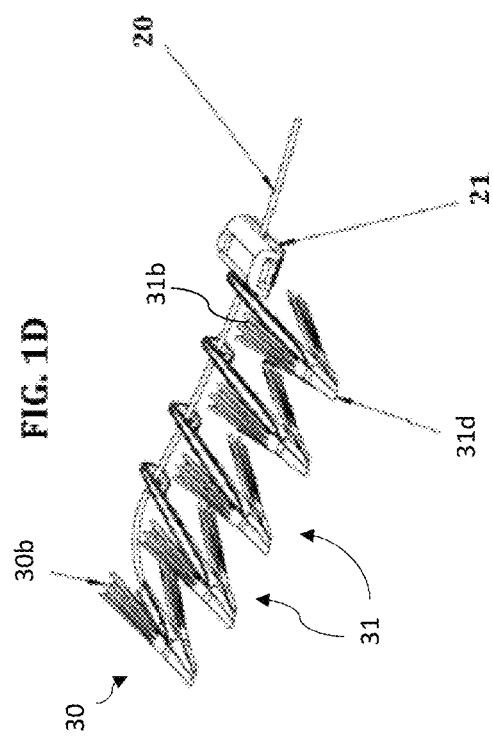
FIG. 1D shows an overhead view of the anchors and suture lock according to an exemplary embodiment of the present invention.

Accordingly, as depicted in FIG. 1D, once the primary anchor 30 and the secondary anchors 31 are driven/anchored into the target tissue, the anchors, and hence the tissue, can be drawn closer together by pulling on the suture 20 tight. The resulting arrangement of the anchors, 30, 31 and the tissue anchored thereto can be held in place with a suture lock 21 that is clamped onto the suture 20. The structure and operation of the suture lock 21 is described in more detail below with reference to FIGS. 8A-9L.

In an example embodiment, these anchors 30 and 31 can be implanted around a heart valve annulus, such as the tricuspid or mitral valve annulus, or other tissue that needs to be drawn together. Accordingly, after the anchors 30 and 31 are anchored in place at appropriate locations about the valve annulus, the valve annulus tissue can be restructured by drawing the suture 20 to move the anchors 30 and 31 together. This addresses the heart valve regurgitation that may occur as valve leaflets lose the ability to properly coapt as a result of the annulus prolapsing over time, limiting the leaflet effectiveness. By bringing the annulus back to a tighter configuration and allowing the valve leaflets to properly coapt, the valve structure is optimized and regurgitation is minimized. This procedure supports various repair and closure procedures, including tricuspid valve repair, mitral valve repair, chordae repair, patent foramen ovale closure, atrial septal defect closure, arterial closure, arterial access site closure, among others.

FIGS. 1E and 1F show another embodiment of an array of anchors connected via a suture 20. In this example embodiment, the primary anchor 32 and the plurality of secondary anchors 33 are similar to the configuration of anchors 30 and 31, respectively, depicted in FIGS. 1C and 1D, except that the distal ends 32d and 33d of the anchors 32 and 33 are tapered to a pointed tip, and are not hollow. The anchors 32 and 33 also comprise a plurality of corrugated wings or barbs 32b and 33b, respectively, that extend proximally and radially outward from the distal ends 32d, 33d of the respective anchors, and, in an example embodiment, are radially flexible with respect to the distal ends, so that the wings or barbs 32b, 33b can be compressed towards the stems or extended radially outward. Each of the anchors 32 and 33 includes a distal end 32d and 33d, respectively, and a stem 32s and 33s, respectively, extending proximally from the distal end. Further, the proximal ends of the stems of the secondary anchors 33 include an eyelet 33e. The purpose of the eyelet 33e is the same as that of the eyelet 31e on the secondary anchors 31 described above.

Figure 2A:
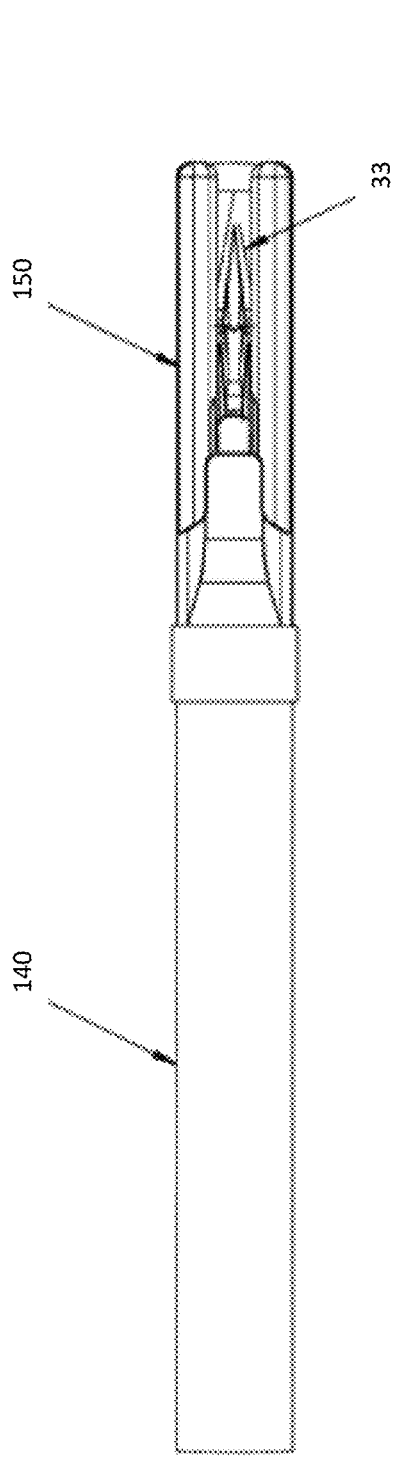
FIGS. 2A-2C show a configuration of a distal anchor housing of the anchor deployment mechanism in FIG. 1A in accordance with an example embodiment of the present invention.
Figure 2B:
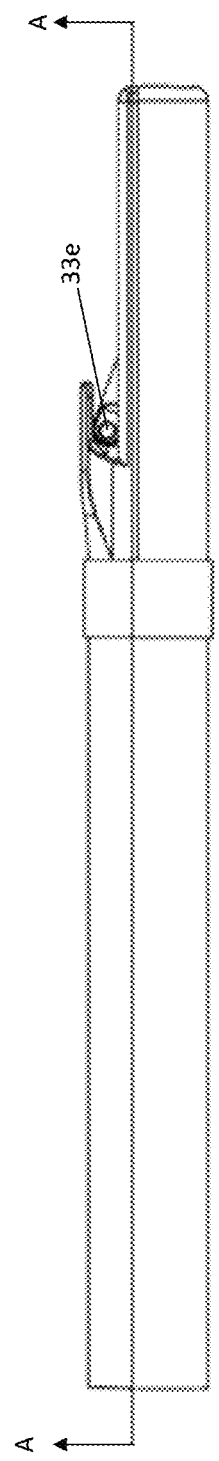
Figure 2C:
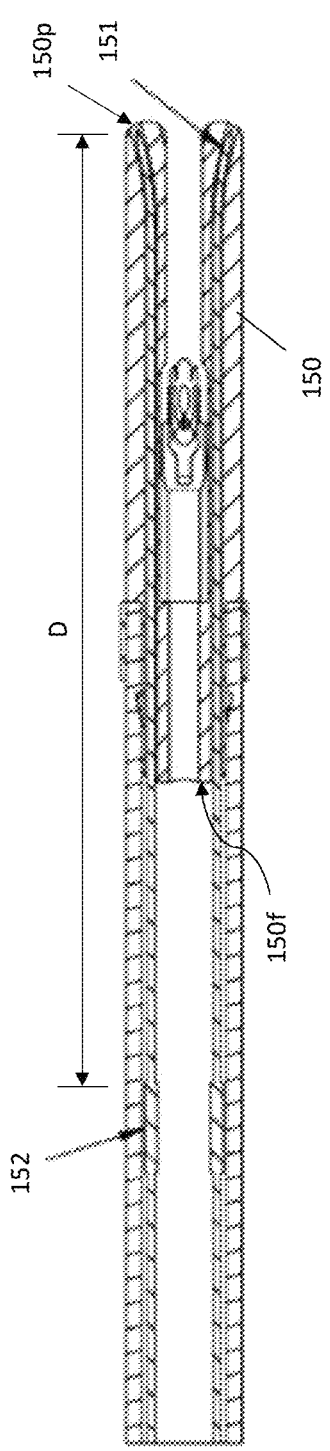
Figure 2D:
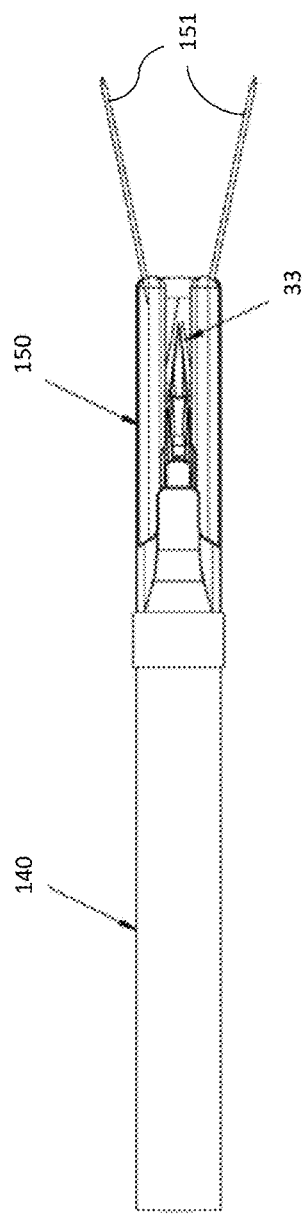
FIGS. 2D-2F show another configuration of a distal anchor housing of the anchor deployment mechanism in FIG. 1A in accordance with an example embodiment of the present invention.
Figure 2E:
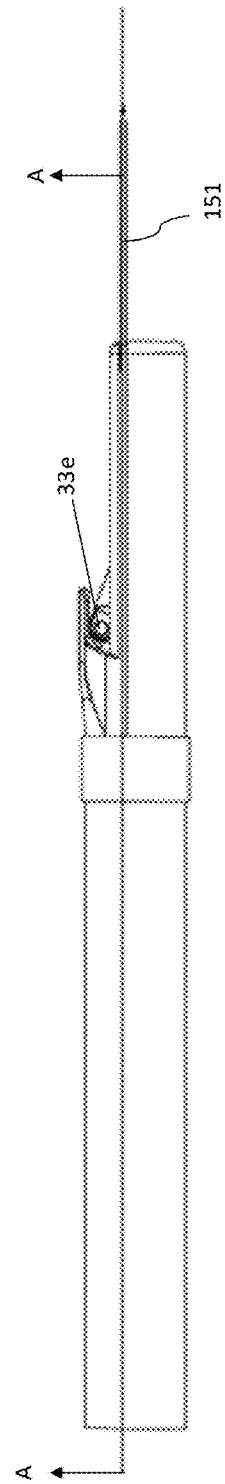
Figure 2F:
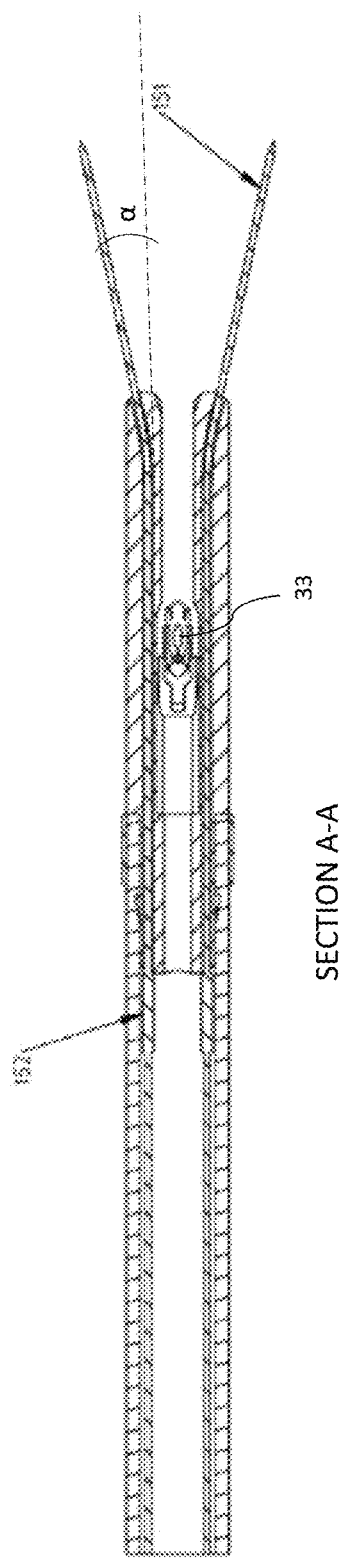

FIGS. 2A-2C show a configuration of a distal anchor housing 150 of the anchor deployment mechanism in FIG. 1A in accordance with an example embodiment of the present invention. As depicted in the longitudinal cross-sectional view in FIG. 2C, the distal anchor housing 150 in this embodiment includes one or more stabilization pins 151. In these illustrations, a secondary anchor 33 is loaded into the distal anchor housing 150 for deployment. In the deployment position loaded in the distal anchor housing 150, the corrugated barbs 33b are in their compressed position against the stem 33e of the anchor 33.

In FIGS. 2A-2C, the stabilization pins 151 are in their retracted position within the distal anchor housing 150. As shown in FIGS. 2D-2F, the anchor deployment device 100 is configured to extend the stabilization pins 151 out of the distal anchor housing 150 in the distal direction. By placing the distal end of the distal anchor housing 150 against the surface of the target tissue location and deploying the stabilization pins 151 into the tissue, the anchor deployment mechanism 100 can be more securely held against the surface of the target tissue before deploying a tissue anchor 30, 31, 32, or 33. Secure positioning of the anchor deployment mechanism 100 can aid in accurately and properly deploying the anchors into the tissue. Further, in an example embodiment, the stabilization pins 151 can be made with a tip sharp enough to pierce the native annulus of the heart. Further, the stabilization pins 151 may be configured to extend from the distal anchor housing 150 at an angle α denoted in FIG. 2F. The angle α can be a perpendicular angle, acute angle, or obtuse angle to the surface of the tissue. In some embodiments, α can be about 5°-20°, and preferably about 13° for applications such as annuloplasty. In an example embodiment, the stabilization pins 151 can enter the tissue to a maximum, set depth regardless of a deflection of catheter tube 140. This is necessary because the catheter length changes as the distal end is deflected. As in the pusher wire, the set depth is achieved by building in an "over travel" length of the stabilization pins, which is longer than the set depth. This "over travel" length allows for sufficient length of the stabilization pins (or, similarly, the pusher wire), regardless of the angle of deflection of the distal end of the device.

Referring to FIG. 2F, a stabilization pin stop 152 is provided on each of the stabilization pins 151 at a fixed distance D from the tip of the stabilization pin 151. The stabilization pin stop 152 can be provided as a bump or a thicker portion that has a larger diameter than the rest of the stabilization pin 151. The stabilization pins 151 can freely travel in the distal direction until the stabilization pin stop 152 contacts a mating geometry at the proximal face 150f of the anchor housing 150 that prevents the stabilization pin 151 from traveling or extending beyond a preset distance in the distal direction by interfering with the proximal end of the anchor housing. At this point, the distal projection of the stabilization pin 151 is at its maximum. The over travel described above is necessary because the catheter tube 140 is deflected at a variety of angles when stabilization pins are being extended. Building in more length than is required and including the stabilization pin stop 152 ensures that they always travel the desired distance regardless of the catheter tube deflection.

Figure 2H:
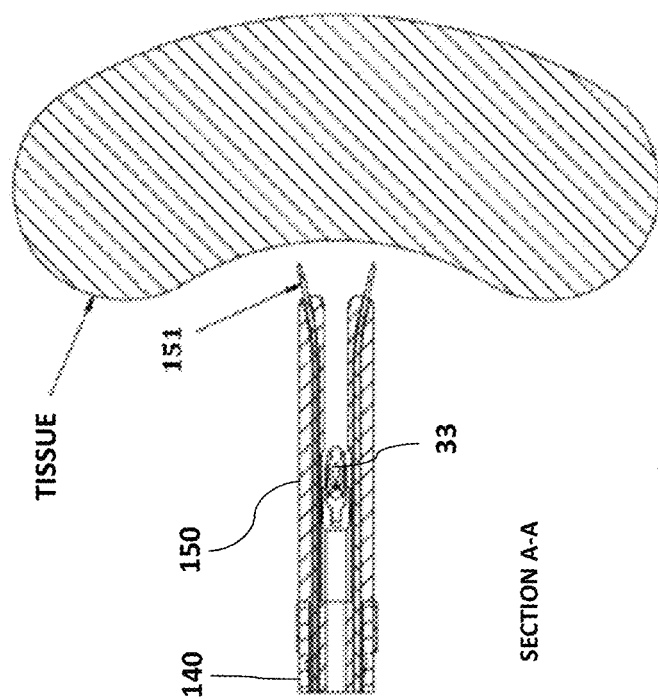
FIGS. 2G-2H show the stabilization pins of FIG. 2A prior to contact with tissue in accordance with an example embodiment of the present invention.
Figure 2G:
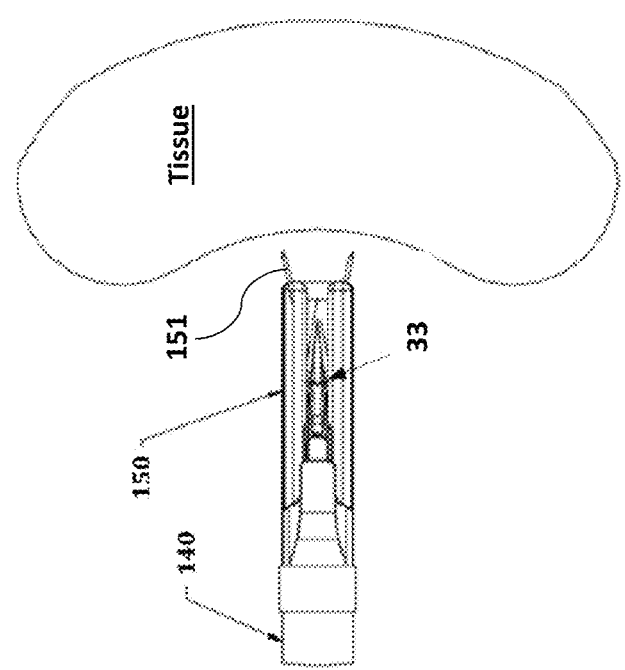

FIGS. 2G and 2H show the stabilization pins 151 prior to contact with the target tissue in accordance with an example embodiment. In particular, the stabilization pins 151 are shown extending partially from the distal anchor housing 150 but the distal anchor housing 150 has not yet in contact with the tissue.

Figure 2J:
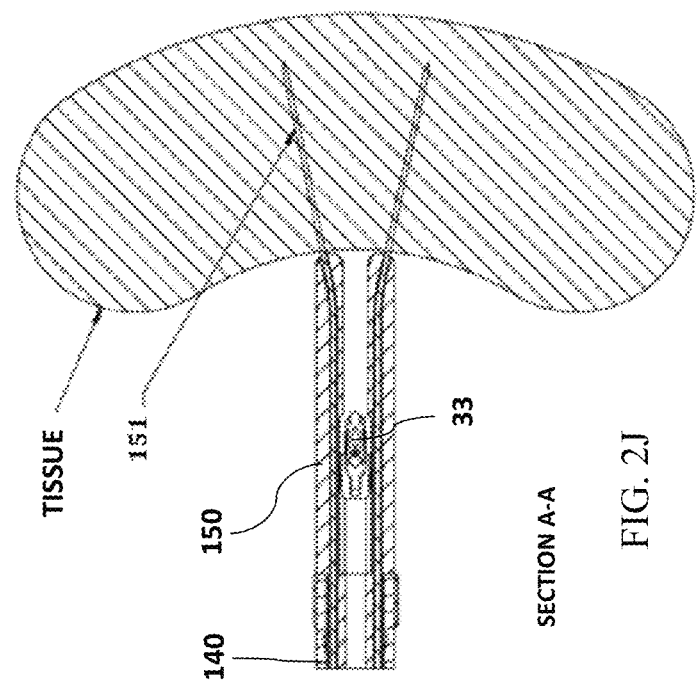
FIGS. 2I-2J show the stabilization pins of FIG. 2A after contact with tissue in accordance with an example embodiment of the present invention.
Figure 2I:
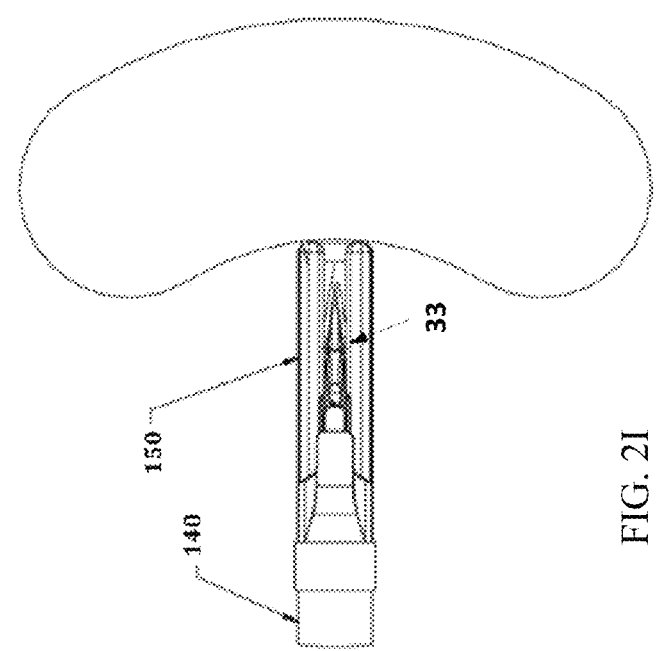

FIGS. 2I and 2J shows after the distal anchor housing 150 has made a contact with the tissue at the desired location and the stabilization pins 151 have been fully deployed into the tissue securing the placement of the distal anchor housing 150 in accordance with an example embodiment. In particular, the sectional view in FIG. 2J shows the stabilization pins 151 embedded within the tissue.

In an example embodiment, the stabilization pins 151 can be used as a sensor to determine when the anchor deployment mechanism is in the proper position against the target tissue site to deploy the anchors. As an example, with the stabilization pins 151 partially extending from the distal anchor housing 150 as shown in FIGS. 2G and 2H, the stabilization pins 151 can be electrically biased, so that the current passes between the stabilization pins 151 through the tissue when the distal end of the distal anchor housing 150 is pressed against or into the tissue. When the stabilization pins 151 are in contact with the tissue, a closed circuit will be achieved between the stabilization pins 151 through the tissue. Once the circuit is closed, one can determine that the distal anchor housing 150 is in contact with the tissue by measuring the impedance between the stabilization pins 151. After contact is detected, the anchor 33 can then be deployed into the tissue.

In some example embodiments, the stabilization pins 151 can be used to detect various levels of impedance, to differentiate between the types of tissue or fluid that may be encountered, such as blood, tissue, the right coronary artery, previously ablated or damaged tissue, other arteries, or other structures that would not be conducive to proper anchor deployment or patient outcomes. For example, the stabilization pins 151 may be configured to detect the electrical impedance of the tissue or fluid encountered by the stabilization pins. The existence of a tissue or fluid between the stabilization pins can create a form of a circuit, a voltage can be applied to the pins, and the opposition of that circuit to the applied voltage can be measured in an electrical feedback system. If the impedance levels are detected to be consistent which predetermined levels corresponding to, e.g., healthy tissue depth, and not levels known to correspond to blood or inadequate tissue depth, then it can be assumed that the stabilization pins have made adequate tissue contact. The detected impedance levels can be presented on a user interface or other display integrated into, or in communication with, the surgical device, including an indication that the stabilization pins have reached a sufficient tissue depth. For example, the display may indicate "sufficient tissue depth," "insufficient tissue depth, "tissue contact," "no tissue contact," "damaged tissue," "artery detected at deployment site," or other information determined by the detected impedance. To enable the electrical features of the stabilization pins 151, the anchor deployment mechanism 100 would be operably connected to one or more appropriate electrical equipment that would be known to those skilled in the art.

Moreover, in an example embodiment, the stabilization pins 151 may be radiopaque, thereby allowing the stabilization pins 151 to be easily identifiable under fluoroscopy. The stabilization pins 151 are positioned near the distal end of the surgical device, and so the visibility of the stabilization pins under fluoroscopy is useful in determining the location of the distal end as the surgical device is being manipulated towards a site for deploying anchors. In this manner, it is helpful to avoid impacting any significant structure or tissue that should not be engaged by the surgical device.

Figure 3C:
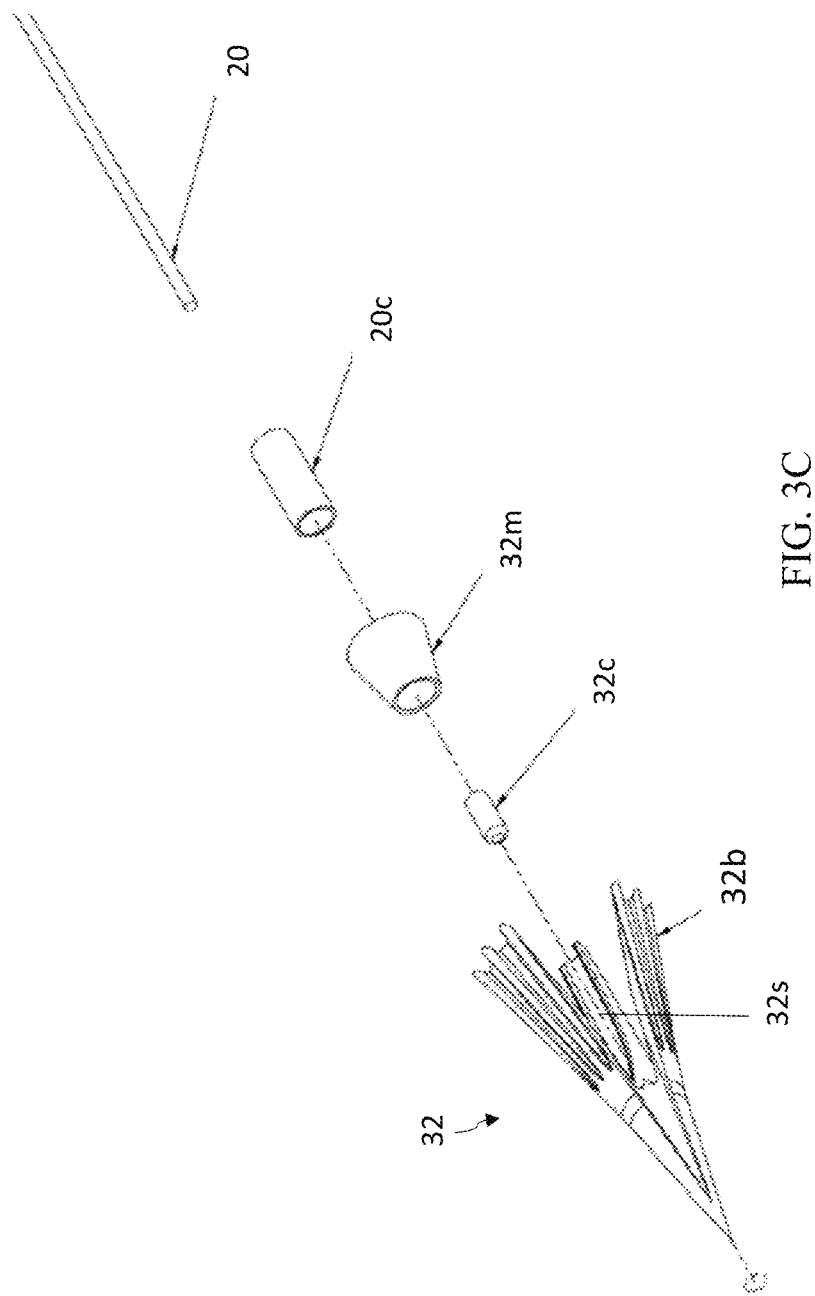

FIGS. 3A-3C show the primary anchor 32 for use in the anchor deployment mechanism 100 of FIG. 1A in accordance with an example embodiment. In an example embodiment, the primary anchor 32 includes a distal end 32d and a stem 32s extending proximally from the distal end. Further, the anchor 32 also includes a plurality of corrugated wings or barbs 32b that extend proximally and radially outward from the distal end of the anchor 32, and, in an example embodiment, are radially flexible with respect to the distal end 32d, so that the wings or barbs 32b may be compressed towards the stem 32s or extended radially outward. Further, in an example embodiment, the anchor 32 can include an anchor cup 32c, a mesh 32m, and an anchor crimp band 20c.

In an example embodiment, the anchor cup 32c is closed at its distal end and open at its proximal end, and may be positioned within the distal end 32d of the anchor 32. Further, the anchor cup 32c is configured to receive the pusher wire 107 of the deployment mechanism 100 via its open proximal end. The anchor cup 32c is provided to protect the anchor 32 from being damaged by the pusher wire 107 during deployment of the anchor. The anchor cup 32c is preferably made of strong material such as stainless steel for that purpose. A tissue anchor 30, 31, 32, or 33 are deployed into the tissue using the anchor deployment mechanism 100 by triggering the pusher wire 107 to quickly push or jab the anchor into the tissue. The pusher wire 107 can be made of stainless steel and the anchors are usually made of a plastic or polymer material. Therefore, the pusher wire 107 can damage the anchor 32 during deployment. The anchor cup 32c also prevents the pusher wire 107 from being embedded in the anchor 32 and possibly pull the anchor out from the tissue during the retraction of the pusher wire 107 after anchor deployment. In an example embodiment, the anchor cup 32c being provided in a metallic form adds another combined beneficial feature because metal is radiopaque, thereby allowing the anchor 32 to be easily identifiable under fluoroscopy.

In an example embodiment, the mesh 32m can be placed between the wings or barbs 32b of the anchor 32, to occupy the distal portion of the space between the barbs 32b to maintain hemostasis. In particular, the mesh 32m minimizes blood flow through the hole in the tissue potentially created by the deployment of the anchor 32. In addition, the mesh 32m can promote coagulation and decrease adverse risk if the anchor 32 is deployed in a manner that breaches a tissue wall. In an example embodiment, the mesh 32m can be comprised of 17 grams per square meter (gsm) polypropylene.

In an example embodiment, the anchor crimp band 20c is located at a proximal end of the anchor stem 32s. The anchor 32 is an example of a primary anchor according to the present disclosure so the anchor is non-slidably affixed to the distal end of the suture 20. The distal end of a suture 20 may be securely affixed to the stem 32s of the anchor 32 by the crimp band 20c which may be closed tightly around the distal end of the suture 20.

Figure 4B:
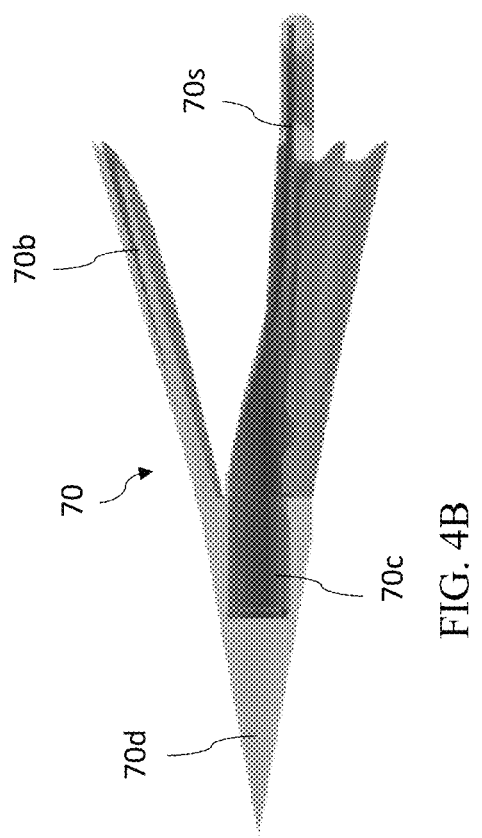
FIGS. 4A-4C show another anchor for use in the anchor deployment mechanism of FIG. 1A in accordance with an example embodiment of the present invention.
Figure 4C:
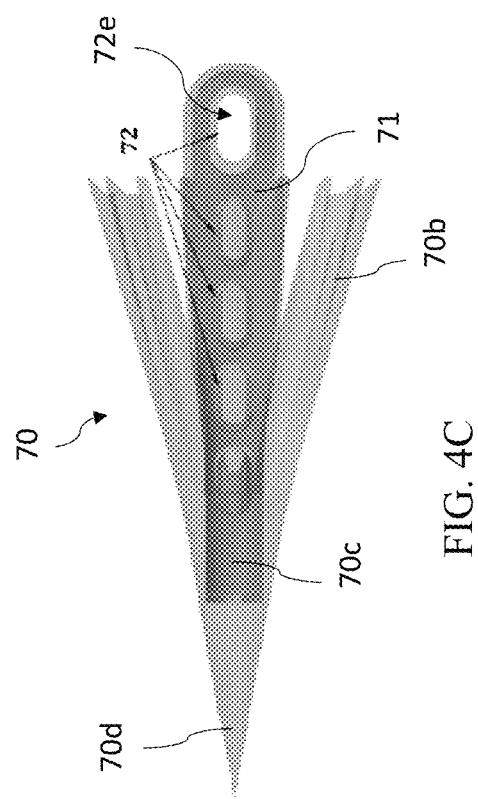
Figure 4A:
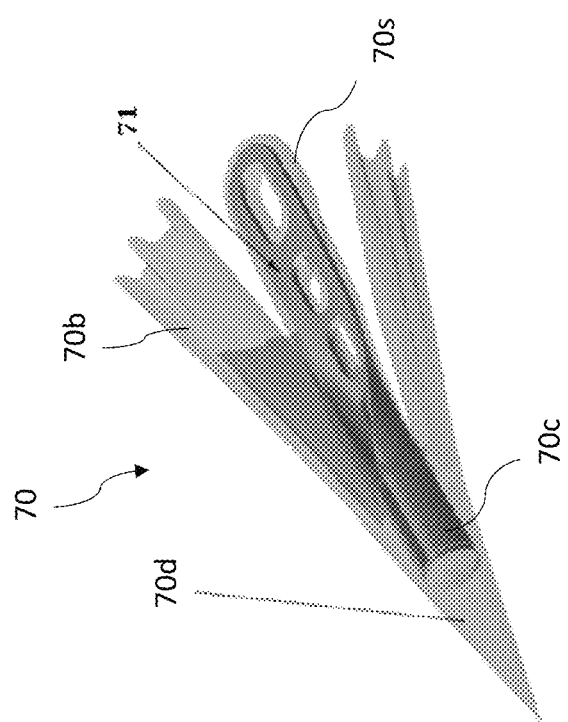

FIGS. 4A-4C show another example of a tissue anchor 70 for use in conjunction with the anchor deployment mechanism 100 of FIG. 1A in accordance with an example embodiment. The tissue anchor 70 is an example of a secondary anchor. FIG. 4A is a perspective view of the anchor 70. FIG. 4B is a side view of the anchor 70. FIG. 4C is a top view of the anchor 70. In an example embodiment, the anchor 70 includes a distal end 70d and a stem 70s extending proximally from the distal end. Further, the anchor 70 also includes a plurality of corrugated wings or barbs 70b that extend proximally and radially outward from the distal end of the anchor 70, and, in an example embodiment, are radially flexible with respect to the distal end 70d, so that the wings or barbs 70b may be compressed towards the stem or extended radially outward.

In an example embodiment, the anchor 70 can be comprised of a soft, compliant material such as polypropylene. Further, in an example embodiment, the anchor 70 can also include a stem insert 71. The stem insert 71 includes an anchor cup portion 70c at its distal end and a plurality of fenestrations 72 at its proximal end. In an example embodiment, the purpose of the anchor cup 70c is the same as the anchor cup 32c discussed above in reference to the tissue anchor 32. The anchor cup 70c is configured to receive a pusher wire such as the pusher wire 107 of the anchor deployment mechanism 100 via its open proximal end.

The stem insert 71 including the anchor cup portion 70c is preferably made of strong material such as stainless steel. The stem insert 71 can be overmolded by the polypropylene that forms the rest of the anchor 70.

Further, in an example embodiment, the fenestrations 72 can facilitate tissue ingrowth after implantation, thereby enhancing the durability of the anchor 70. At least one of the fenestrations such as the one denoted as 72e can be used to feed the suture 20 through like the eyelets 31e and 33e in the anchor embodiments 31 and 33. In some embodiments, some of the fenestrations 72 in the stem insert can be overmolded with the anchor body material (e.g. polypropylene). Depending on the particular shape of the stem insert 71, overmolding more portions of the stem insert 71 could help prevent any unwanted separation of the stem insert 71 from the anchor body while still maintaining their ability to facilitate tissue ingrowth. For example, in the example shown in FIG. 4C, the fenestrations 72 other than the one denoted as 72e are overmolded with polypropylene.

Figure 4E:
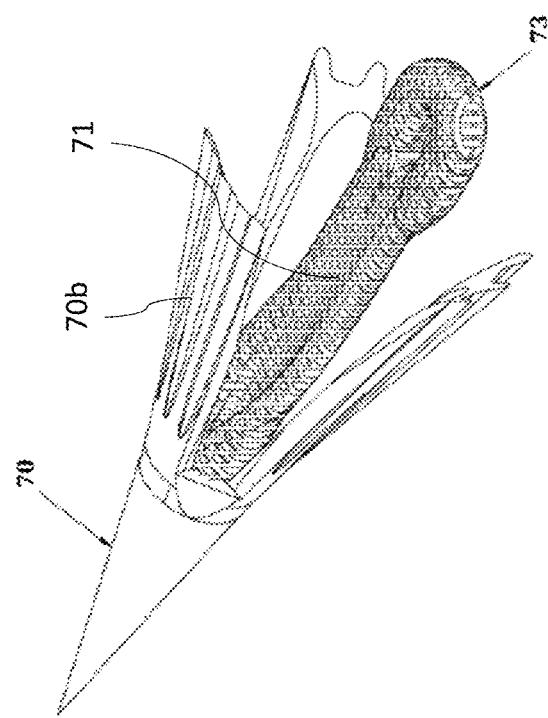
FIG. 4E shows another anchor for use in the anchor deployment mechanism of FIG. 1A in accordance with an example embodiment of the present invention.
Figure 4D:
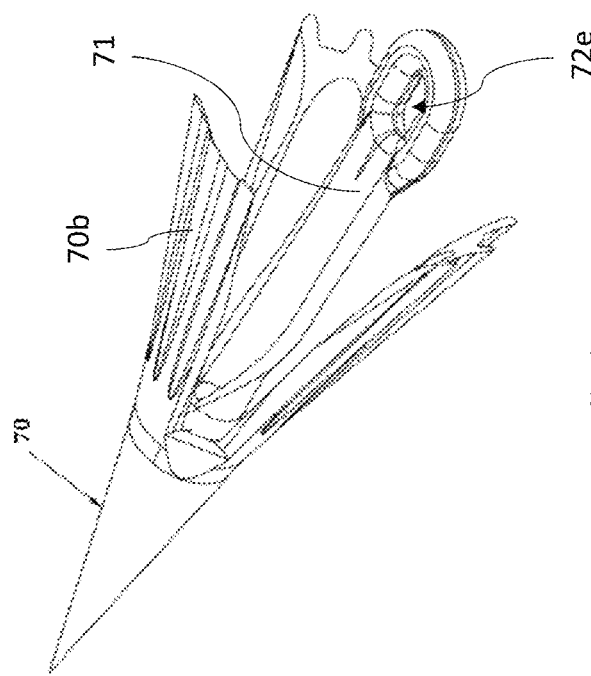
FIG. 4D shows another anchor for use in the anchor deployment mechanism of FIG. 1A in accordance with an example embodiment of the present invention.

FIG. 4D illustrates an alternative exemplary embodiment of the anchor 70, without the fenestrations 72 as part of stem insert 71. Further, as illustrated in FIG. 4E, the whole of anchor 70, or some portion thereof, can be jacketed in Fibrin or other biologic coating 73 to promote tissue ingrowth.

Figure 4G:
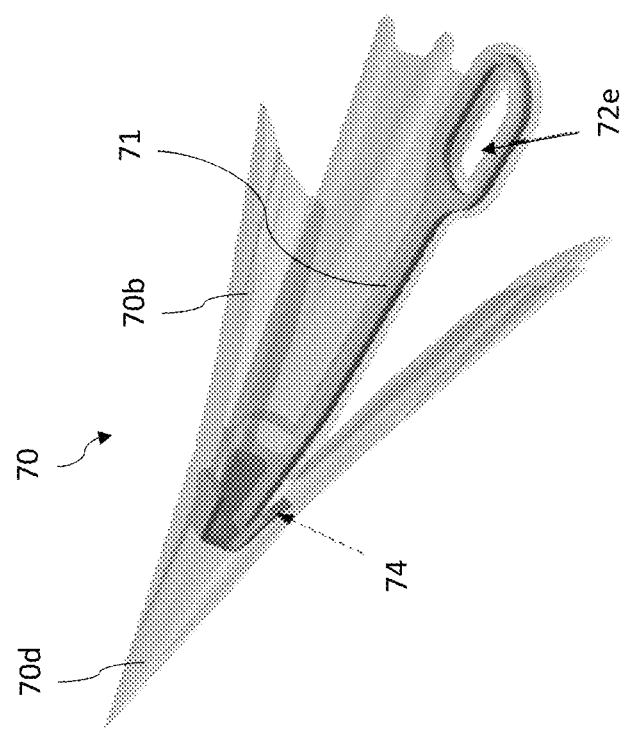
FIGS. 4F-4G show another anchor for use in the anchor deployment mechanism of FIG. 1A in accordance with an example embodiment of the present invention.
Figure 4F:
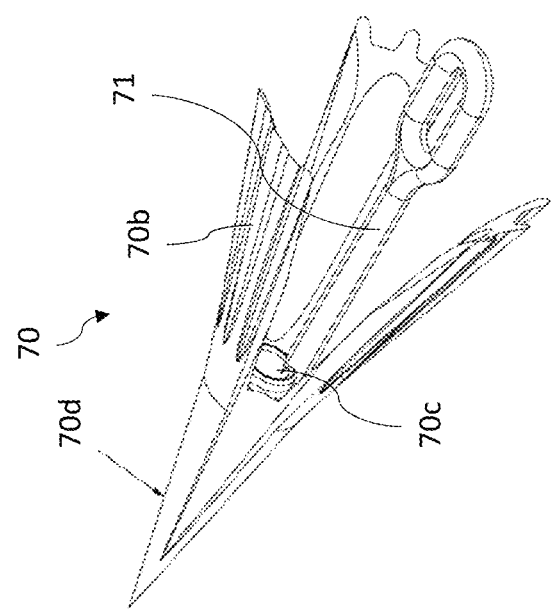

FIGS. 4F-4G show another alternative embodiment of the anchor 70, without the fenestrations 72 as part of stem insert 71, and including an alternative embodiment of the anchor cup 70c. In this embodiment, the anchor cup portion of stem insert 71 is comprised of tabs 74 aligned with the wings or barbs of the anchor 70. As mentioned previously, the stem insert 71 is made of a metal such as stainless steel. In FIG. 4G, the body of the anchor 70 formed of polypropylene is rendered to be translucent to show the tabs 74.

In addition, in any of the embodiments of the anchor, the stem insert 71 can be comprised of a metal, thereby providing some metallic rigidity to the anchor 70. Further, the stem insert 71 can also be radiopaque, thereby allowing the stem insert 71 to be easily identifiable under fluoroscopy.

Figure 5B:
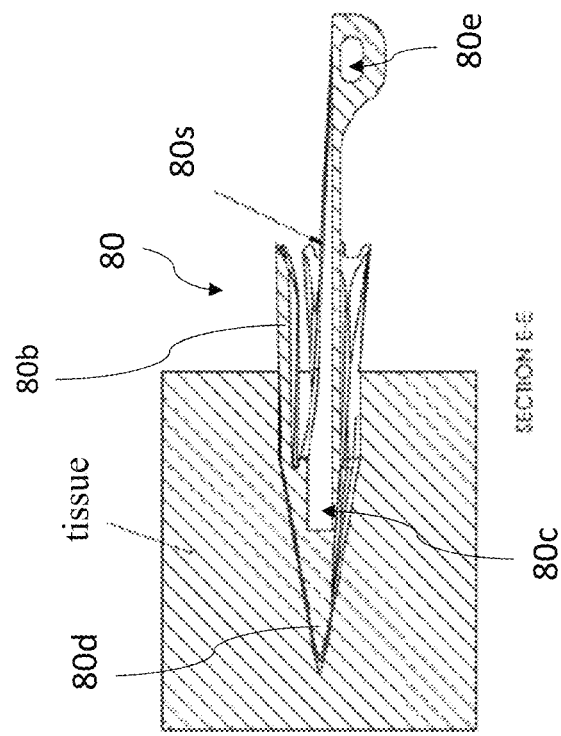
FIGS. 5A-5B show another anchor for use in the anchor deployment mechanism of FIG. 1A in accordance with an example embodiment of the present invention.
Figure 5A:
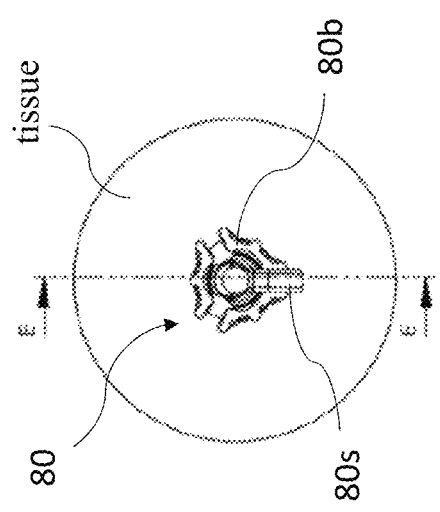

FIGS. 5A-5B show another anchor 80 for use in the anchor deployment mechanism 100 of FIG. 1A in accordance with an example embodiment of the present invention. FIGS. 5A and 5B are illustrations of the anchor 80 at a point in time during the deployment procedure where the anchor 80 has partially penetrated into the tissue. FIG. 5A shows a view from the proximal end of the anchor 80 and FIG. 5B is a longitudinal sectional view taken along the section line E-E in FIG. 5A. In both views, the flexible corrugated barbs 80b have collapsed radially inward toward the stem 80s as the anchor advances into the tissue. The circle around the anchor 80 in FIG. 5A denotes the tissue region surrounding the anchor. In an example embodiment, the anchor 80 includes a distal end 80d and a stem 80s extending proximally from the distal end 80d. In an example embodiment, the anchor 80 also includes a plurality of corrugated wings or barbs 80b that extend proximally and radially outward from the distal end 80d of the anchor 80, and, in an example embodiment, are radially flexible with respect to the distal end, so that the wings or barbs 80b may be compressed towards the stem 80s or extended radially outward (similar to the canopy of an umbrella). In an example embodiment, the distal end 80d of the anchor 80 is hollow. Further, in an example embodiment, the stem 80s is flexible with respect to the distal end 80d of the anchor 80 and the wings or barbs 80b of the anchor 80. The stem 80s can also include a concave profile as viewed from the proximal end of the stem which allows the pusher wire to slip into the concave portion and be guided toward the anchor cup 80c during the deployment of the anchor. This concave profile can be better seen in the anchor embodiment 32 in FIG. 3C. The anchor 32 has a stem 32s. The stem 32s is generally a tubular shaped structure but is open along its length as shown. Thus, the stem 32s forms a trough like structure that is being referred to herein as concave profile. Further, as the anchor 80 is an example of a secondary anchor, the proximal end of the stem also includes an eyelet 80e through which the suture 20 can be threaded.

In an example embodiment, the anchor 80 includes three wings or barbs 80b that are configured to collapse upon entering the tissue as depicted in the figure. In particular, the three wings or barbs 80b can be at an equal distance away from each other, thereby providing radial symmetry between the wings or barbs. The radial symmetry enables the anchor 80 to advance into the tissue in a straight path. Although not shown in FIG. 5B, if the anchor deployment mechanism 100 is being used to deploy the anchor 80 into the tissue, the pusher wire 107 would be positioned in the anchor cup 80c and pushing the anchor 80 in the distal direction.

Figure 5C:
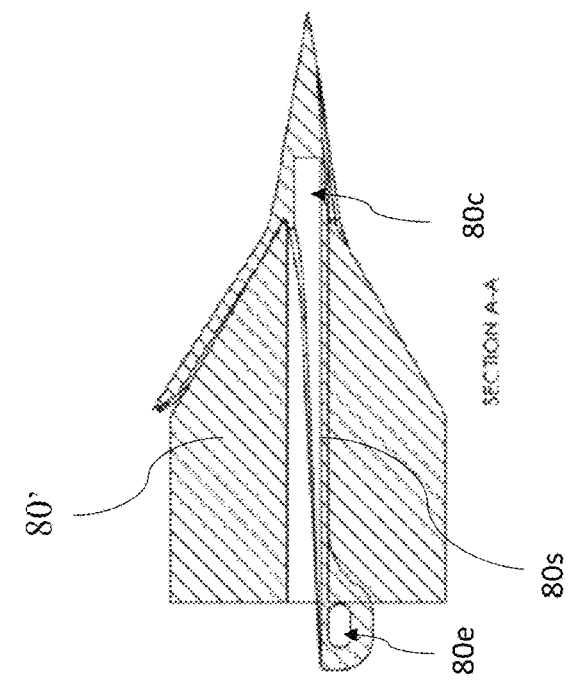
FIGS. 5C-5E show the anchor in FIG. 5A in accordance with another example embodiment of the present invention.
Figure 5D:
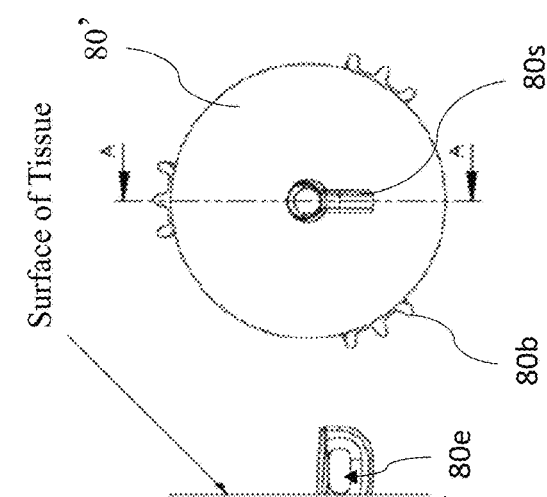
Figure 5E:
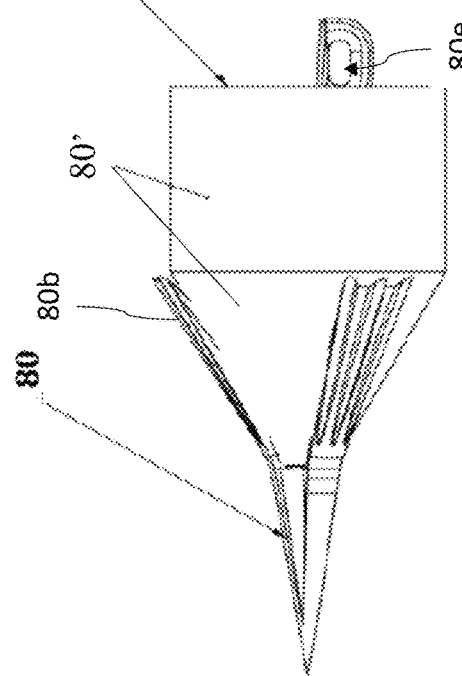

FIGS. 5C-5E show the anchor 80 of FIGS. 5A-5B in accordance with another example embodiment. FIG. 5C is a side view of the fully deployed anchor 80. FIG. 5D is a view of the fully deployed anchor 80 from the proximal end. FIG. 5E is a longitudinal sectional view of the fully deployed anchor 80 taken along the section line A-A in FIG. 5D. In particular, FIGS. 5C-5E show the anchor 80 after it is fully embedded into the tissue. In an example embodiment, after the anchor 80 has entered the tissue into its fully seated position, when a tension is applied to the suture 20 (not shown in FIGS. 5A-5E) to pull the array of anchors (i.e. one primary anchor and subsequently deployed plurality of secondary anchors 80) together by the suture 20, the suture 20 would apply some amount of pulling force in proximal direction. This proximal pulling action causes the three wings or barbs 80b to open up in response and captures a roughly cone shaped volume of tissue 80' in the proximal direction from the barbs 80b as shown in FIGS. 5C-5E. This results in maximizing the volume of the tissue that resists pullout of the anchor 80. Thus, stress may be distributed over a greater mass of tissue.

Figure 6C:
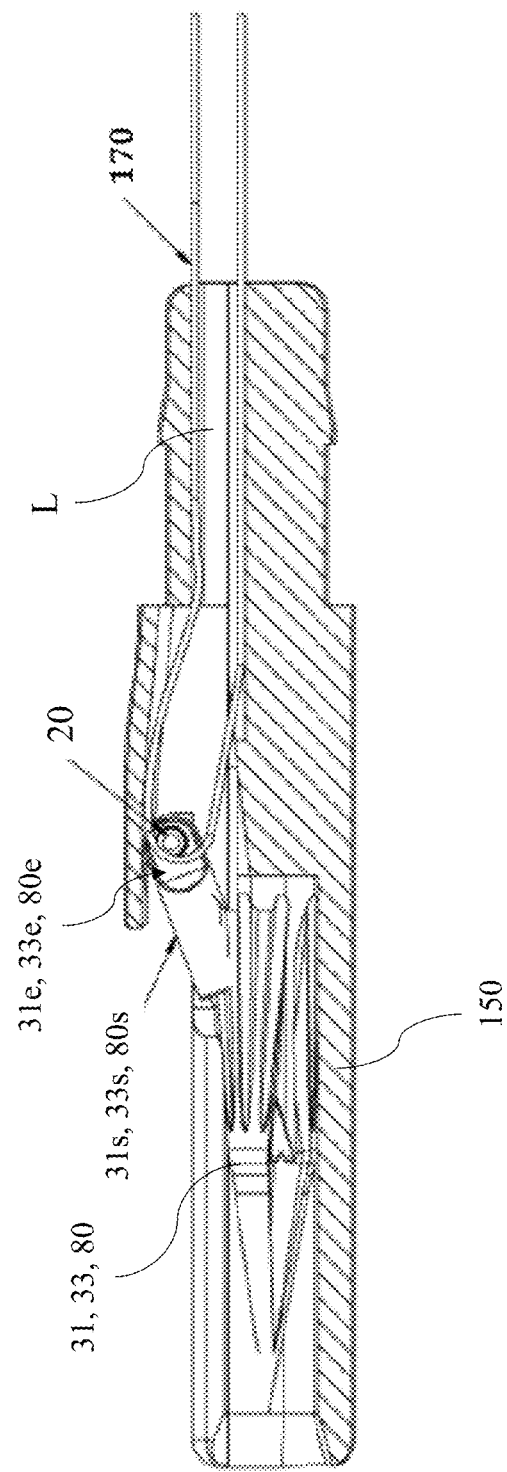

FIGS. 6A-6C show a distal anchor housing 150 of the anchor deployment mechanism 100 in FIG. 1A in accordance with an example embodiment of the present invention. After a primary anchor is deployed at the surgical site, before a secondary anchor, such as 31, 33, or 80 can be deployed at the surgical site, such secondary anchor need to be first loaded into the distal anchor housing 150 and the free end of the suture 20, which is attached to the already deployed primary anchor, is threaded through the eyelet 31e, 33e, or 80e of the secondary anchor 31, 33, 80, respectively. Then, the free end of the suture 20 needs to be threaded through the length of the catheter tube 140 of the anchor deployment mechanism 100 up to or close to the handle 110. However, because the suture 20 is floppy like a thread, this threading task can be difficult if not impossible. According to an embodiment of the present disclosure, the anchor deployment mechanism 100 can be configured with a snare 170 to recapture the suture 20 and thread it through the catheter tube 140.

For example, according to the surgical procedure of the present disclosure, after a primary anchor 30 or 32 has been deployed in the tissue of the surgical site, the suture 20 remains connected to that primary anchor and a secondary anchor 31, 33, or 80 can be applied to the same surgical site by loading a secondary anchor to the distal anchor housing 150 of the anchor deployment mechanism 100, threading the free end of the suture 20 through the eyelet 31e, 33e, or 80e of the secondary anchor, and then threading the free end of the suture 20 through a loop of snare 170 as shown in FIGS. 6A-6C.

Next, the distal anchor housing 150 end of the anchor deployment mechanism 100 is percutaneously inserted to the surgical site by sliding the loaded secondary anchor along the suture 20. As can be seen in the longitudinal cross-section view of the distal anchor housing 150 in FIG. 6C, the snare 170 is positioned adjacent to the eyelet 31e, 33e, or 80e of the secondary anchor 31, 33, or 80. The snare 170 is positioned within a lumen L that extends from the distal anchor housing 150 through the catheter tube 140 to the handle 110. Therefore, the suture 20 which is now captured by the loop of snare 170 can be threaded through the length of the catheter tube 140 by pulling of the snare 170 through the lumen L to draw the suture 20 in the proximal direction of the device, via a snare grip (not shown), located in the handle of the device. Once the suture 20 has been drawn back to the proximal handle, the secondary anchor 31, 33, or 80 can be deployed in a similar manner to the primary anchor. Similarly, additional secondary anchors can be deployed by repeating this process.

Additionally, a suture locking device and the suture cutting device described below can also be deployed to the same surgical site by similar procedural steps: (1) passing the free end of the suture 20 through the suture locking device or the suture cutting device; (2) attaching the suture locking device or the suture cutting device to the distal end of the catheter tube 140; (3) passing the free end of the suture 20 through the snare 170; (4) recapturing the suture 20 through the catheter tube 140 by pulling the snare 170 through the lumen L; then (5) deploying the suture locking device or the suture cutting device to the surgical site by advancing the catheter tube 140 percutaneously to the surgical site. In some embodiments, the above-recited steps (2) and (3) may be performed in reverse order. In particular, this loading of the suture 20 within the catheter tube 140 allows for increased friction control and precise suture management when applying a secondary anchor to the same suture that is attached to a primary anchor. Further, the snare 170 may be composed of a nitinol wire for improved strength and precision.

Figure 6D:
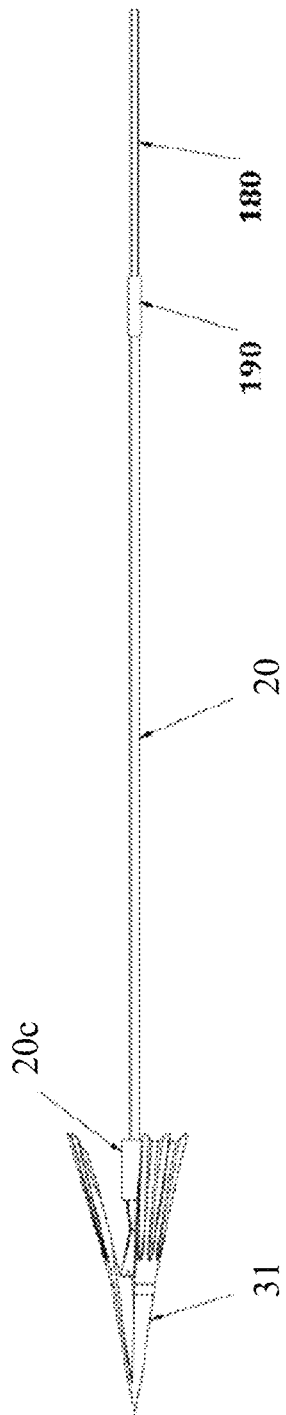
FIG. 6D shows an anchor and suture for use with the anchor deployment mechanism in FIG. 1A in accordance with an example embodiment of the present invention.

Alternatively, according to an exemplary embodiment, instead of using the snare 170, a wire 180 attached to the free end of the suture 20 can be used to facilitate the reloading of the suture 20 through the catheter tube 140 during the secondary anchor loading procedure, suture locking device loading procedure, or the suture cutting device loading procedure. FIG. 6D shows a suture 20 connected to a primary anchor 31. As in FIG. 3A, the distal end of the suture 20 may be securely attached to the anchor 31 by a crimp band 20c. In this embodiment, the free end of the suture 20 may be connected to a wire 180. The wire 180 may be made from any material that is stiffer than the suture 20, including nitinol or stainless steel. The wire 180 may be crimped or otherwise attached to the suture 20, such as by a wire-suture crimp band 190. In this exemplary embodiment, after the primary anchor 31 has been deployed into the surgical site, instead of passing the free end of the suture 20 through both the eyelet 32e of a secondary anchor 32 and the snare 170, the wire 180, connected to the free end of the suture 20, may be passed through the anchor eyelet 32e and then passed into the lumen L, shown in FIG. 6C, provided in the distal anchor housing 150 at the distal end of the catheter. Alternatively, the catheter tube 140 may include a hole in the side of the catheter, located at a position proximal to the distal end. The stiffness of the wire 180 allows for the wire to be passed into the distal end of the catheter tube 140 with ease through at least some portion of the length of the catheter, and out through the side hole. The wire 180 may be manipulated to draw the suture 20 through the anchor eyelet, into the distal end of the catheter, such that the free end of the suture 20 can be drawn through the hole in the catheter. The hole in the catheter may be located at a position proximal to the distal end, far enough from the distal end such that, when the distal end of the catheter is returned to the surgical site, the free end of the suture 20 remains sufficiently outside of the surgical site that it may be manipulated during the surgical procedure. In an exemplary embodiment, the hole is located 20 centimeters from the distal end. In this manner, a secondary anchor can be deployed on the same suture as the primary anchor. In particular, this exemplary embodiment permits the securing of the suture 20 without drawing the suture all the way to the proximal handle, allowing for a shorter suture, and limiting the concern that the suture will experience unnecessary proximal force that may cause the deployed anchors to damage tissue.

Figure 7A:
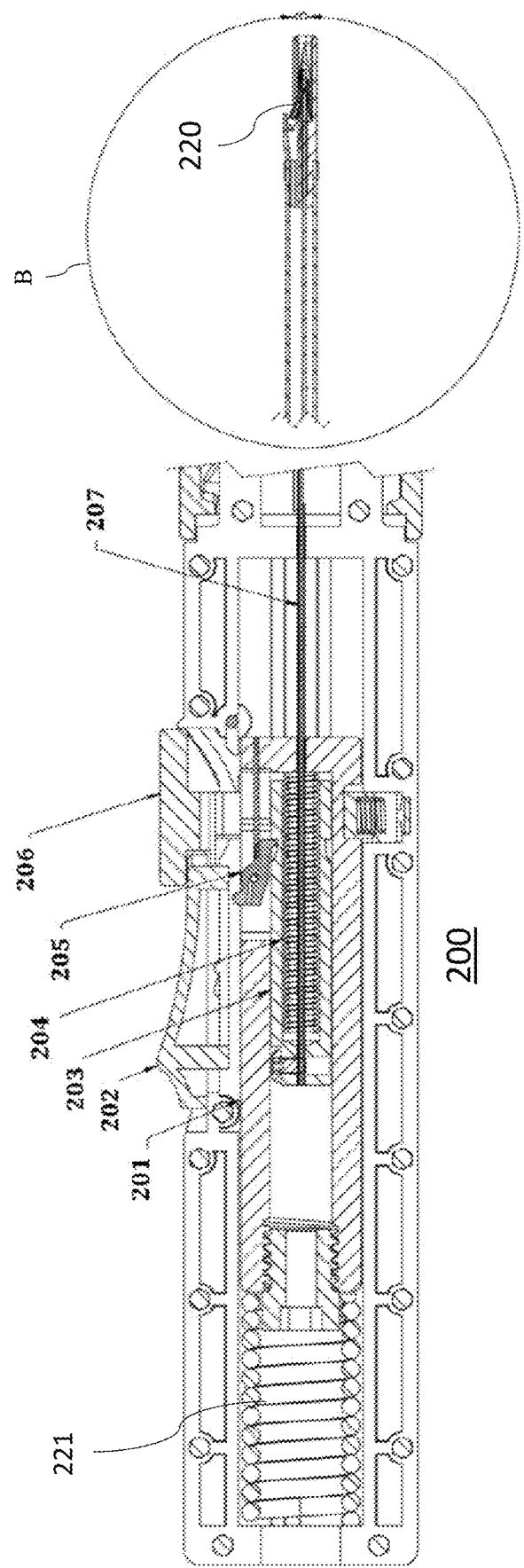

FIGS. 7A-7B show an anchor deployment mechanism 200 in accordance with an example embodiment of the present invention. FIG. 7B shows the detailed view of the distal end of the anchor deployment mechanism 200 denoted as area B in FIG. 7A. The structure of the mechanism in the handle portion of the anchor deployment mechanism 200 is similar to those of the anchor deployment mechanism 100 discussed above. As depicted in the figure, an anchor deployment device 200 can include a compression spring 221 a pusher carriage 201, a safety button 202, a pin retractor 203, a pin retractor spring 204, a pawl 205, a release button 206, pusher wire 207, a catheter tube 210, and a distal anchor housing 220. In an example embodiment, the pusher wire 207 can include a stop 207a. Further, the distal anchor housing 220 can include an anchor support tube 221 and the anchor 80. In an example embodiment, the elements within the anchor deployment device 200 are configured to impart a pushing force on the anchor 80 located in the distal anchor housing 220. For example, if the safety button 202 is maintained in an "off" position, a user can selectively transfer a pushing force from the pusher carriage 201, via the pusher wire 207, to the anchor 80 by engaging the release button 206. However, as depicted in the figure, the safety button 202 is maintained in an "on" position, thereby preventing the user from engaging the release button and, thus, the deployment of the anchor 80. Further, the anchor deployment device 200 can be configured to retract the pusher wire 207 back into the anchor deployment device 200, e.g. immediately after anchor deployment, with the pin retractor 203 and the corresponding pin retractor spring 204. In particular, the pin retractor 203 can retract the pusher wire 207 after the pawl 205, which maintains the position of the pin retractor 203, is tripped. As such, if the pawl 205 is not tripped, then the pin retractor 203 will remain in connection with the pawl 205 and, therefore, will not cause the pusher wire 207 to retract.

In an example embodiment, the catheter tube 210 is steerable such that the catheter tube 210 may be articulated or bent to suit the needs of the application. When the catheter tube 210 is in its bent form, a pusher wire (e.g., wire 207) may not meet the distal end of the catheter in the same relative position as it would in a straight, unbent catheter. Accordingly, there is a need to provide a uniform distance for the pusher wire 207 to drive the anchors from the distal end of the catheter, independent of the form or shape of the steerable catheter. To solve this problem, a collar or flange, i.e., the stop 207a, may be added to the pusher wire 207 at a predetermined distance from the distal end of the pusher wire 207. In an example embodiment, the collar extends radially from the pusher wire, creating a diameter large enough to abut a mating geometry at the proximal face of distal anchor housing 220 and stop the distal movement of the pusher wire 207, to keep the pusher wire 207 from extending beyond the distal end of the anchor housing 220 at more than a predetermined distance. In an example embodiment, the pusher wire 207, independent of the positioning of the steerable catheter tube 210, will be pushed to this predetermined distance.

For example, if the pusher carriage 201 travels 23 mm and the anchor 80 is allowed to travel no more than 16 mm, then the pusher wire 207 is set back 6 mm from contact with the anchor 80 (i.e. contact with the anchor cup 80c of the anchor 80) when the catheter tube 210 is straight. As the catheter tube 210 is deflected up to 90 degrees, the overall length of the catheter tube 210 will be shortened by approximately 6 mm, which is compensated for by the gap between the distal tip of the pusher wire 207 and the anchor 80 when the catheter tube 210 is straight. In an example embodiment, the stop 207a on the pusher wire 207 contacts the proximal surface of the distal anchor housing 220 after the anchor 80 travels 16 mm.

Figure 7C:
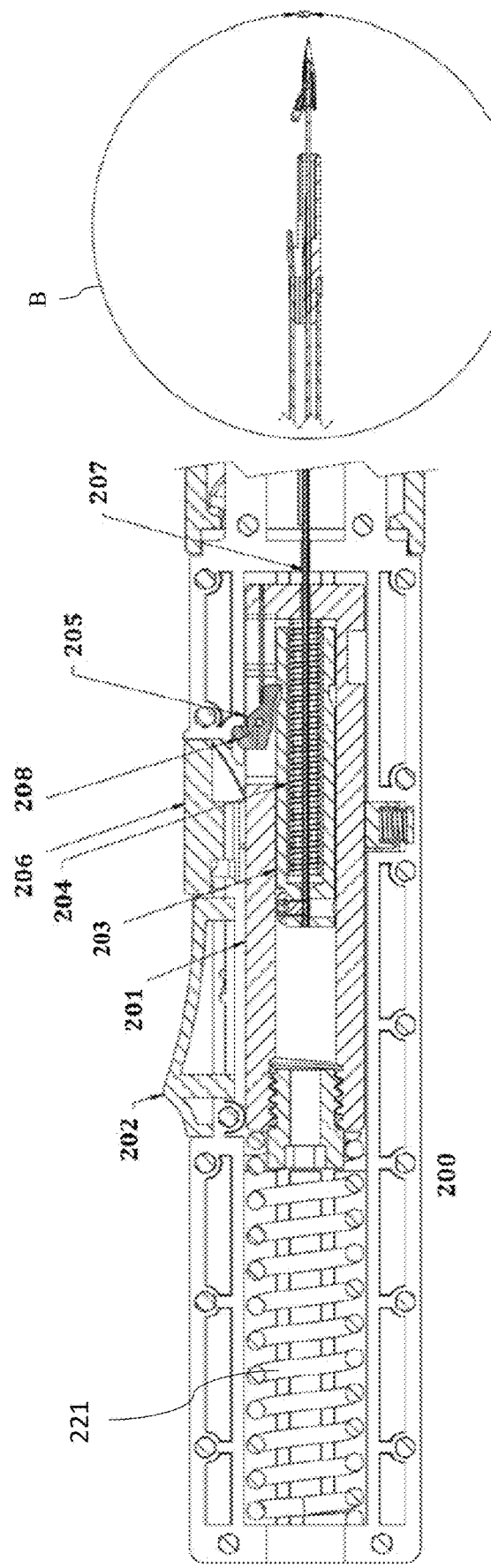
FIGS. 7C-7D show another configuration of the anchor deployment mechanism in FIG. 7A in accordance with an example embodiment of the present invention.
Figure 7D:
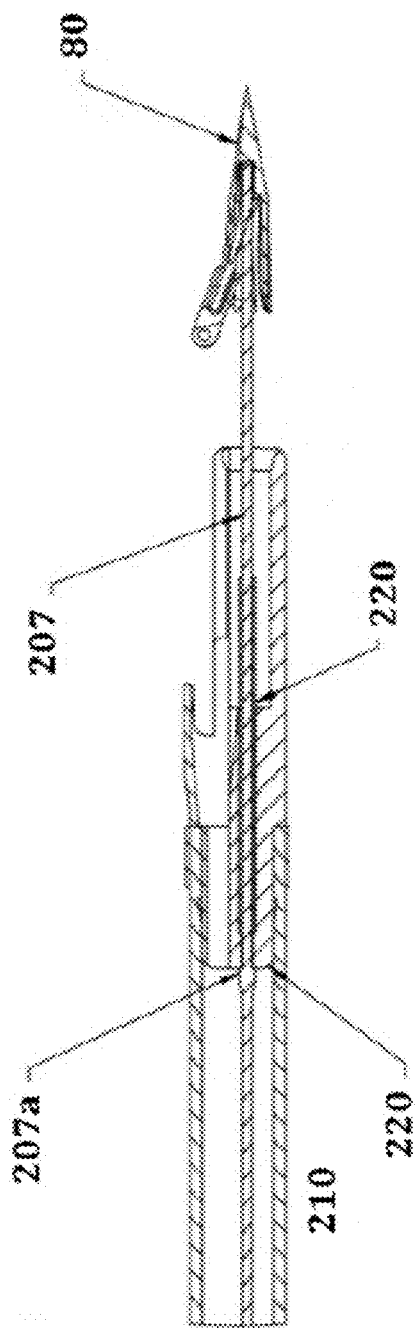

FIGS. 7C-7D show another configuration of the anchor deployment mechanism 200 shown in FIG. 7A in accordance with an example embodiment. In particular, FIG. 7C shows the anchor deployment device 200 with the safety button 202 in an "off" position, thereby allowing the user to engage the release button 206 to transfer a pushing force from the pusher carriage 201 to the anchor 80. Specifically, when the release button 206 is engaged (e.g., pressed), the release button 206 disengages from a notch in the pusher carriage 201, thereby allowing the compression spring 221 to push the pusher carriage 201 in the distal direction which, in turn, exerts a pushing force on the anchor 80 in the distal direction. In an example embodiment, the pushing force from the pusher carriage 201 is transmitted to the anchor 80 via the pusher wire 207. In another example embodiment, the pushing force exerted on the anchor may be imparted by other electrical, mechanical, pneumatic, or hydraulic operation. Further, as depicted in FIG. 7D, the anchor 80 is pushed in the distal direction until the stop 207a on the pusher wire 207 contacts the proximal surface of the distal anchor housing 220. In addition, after deployment of the anchor 80, the pawl 205 may contact a pin 208. This is an intermediate stage, as the pusher carriage 201 depicted in this figure has not reached full travel.

Figure 7E:
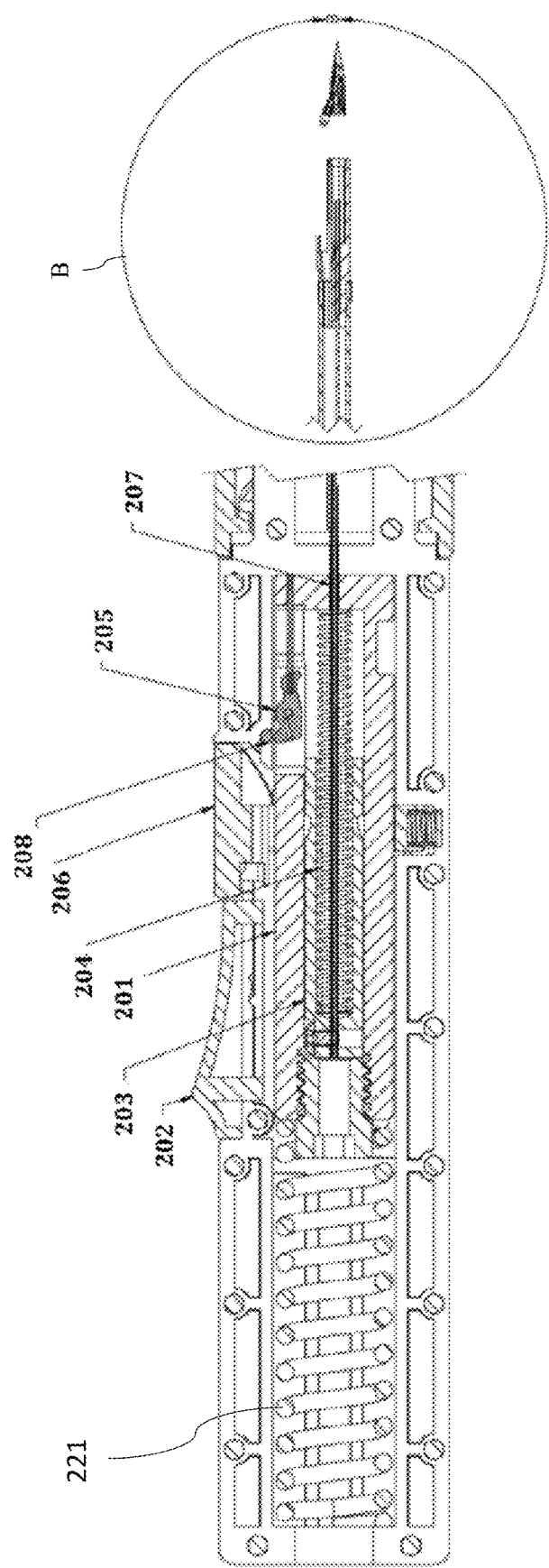
FIGS. 7E-7F show another configuration of the anchor deployment mechanism in FIG. 7A in accordance with an example embodiment of the present invention.
Figure 7F:
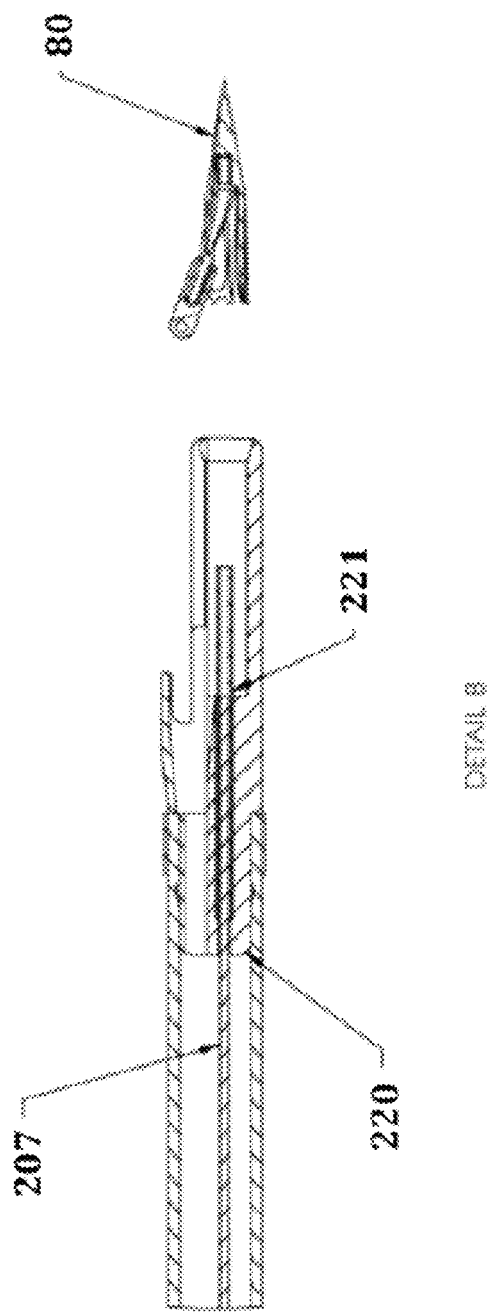

FIGS. 7E-7F shows another configuration of the anchor deployment mechanism in FIG. 7A in accordance with an example embodiment of the present invention. In particular, FIG. 7E shows the anchor deployment device 200 after full travel of pusher carriage 201, and the pawl 205 tripped by the pin 208. In an example embodiment, the pin 208 can cause the pawl 205 to trip after a retract button (not shown) is engaged (e.g., pressed). Further, as depicted in the figure, after the pawl 205 is tripped, the pin retractor 203 is released from the pawl 205's grip, which causes the corresponding pin retractor spring 204 to extend in the proximal direction. In an example embodiment, the extension of the pin retractor spring 204 in the proximal direction causes the pin retractor 203 to also move in the proximal direction. Further, because the proximal end of the pusher wire 207 is attached to the proximal end of the pin retractor 203, the pusher wire 207 is pulled (i.e., retracted) in the proximal direction. In an example embodiment, the pusher wire 207 can be retracted immediately after the anchor 80 is deployed into tissue. As such, the pusher wire 207 is retracted without the anchor 80.

Figure 8A:
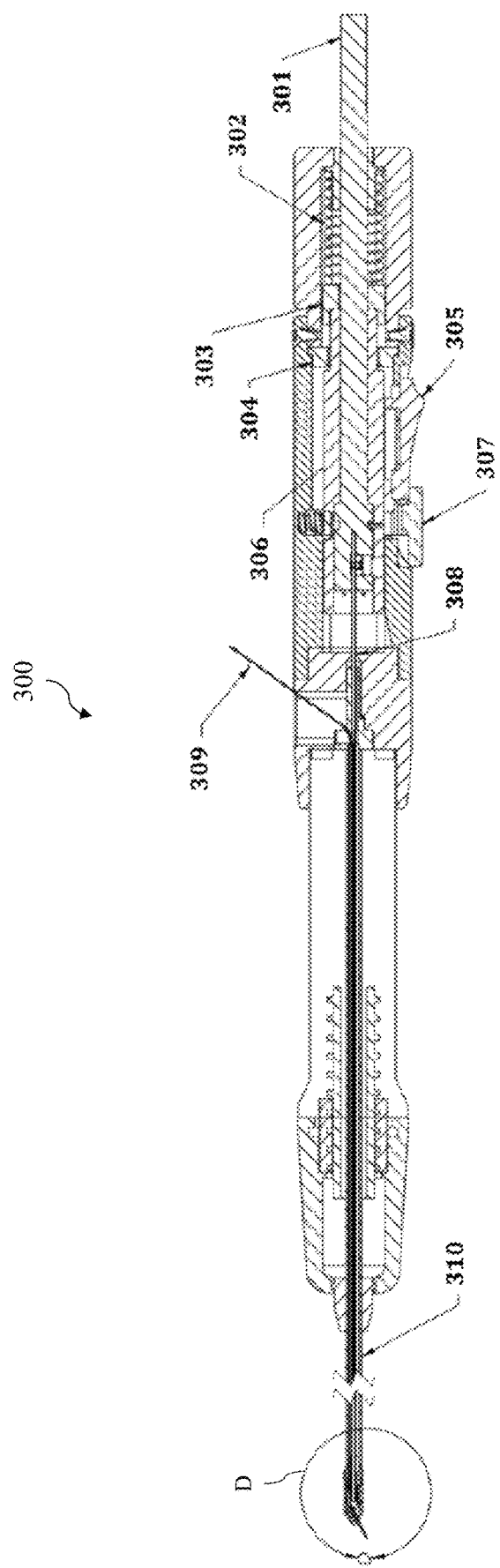
FIGS. 8A-8B show an suture lock deployment mechanism in accordance with an example embodiment of the present invention.
Figure 8B:
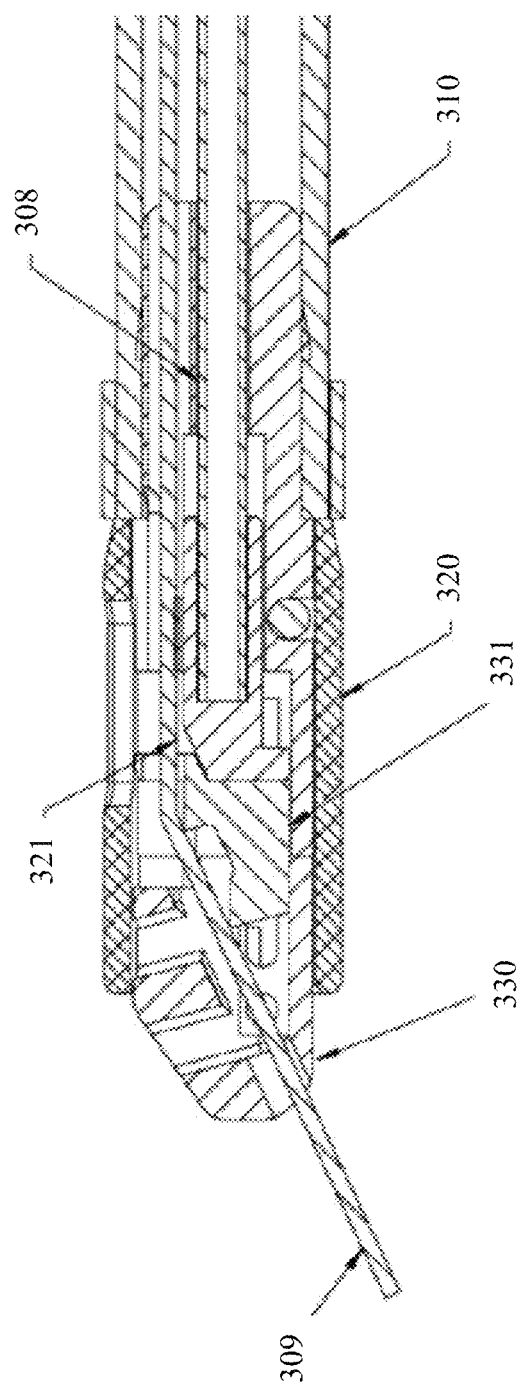

FIGS. 8A-8B show a suture locking mechanism in accordance with an example embodiment of the present invention. As depicted in the figure, a suture locking device 300 can include a release shaft 301, a deployment spring 302, a spring sleeve 303, a stepped washer 304, a safety button 305, a pusher 306, a release button 307, a pusher tube 308, a suture 309, a catheter tube 310, a distal housing 320, a suture locking housing 330, and a suture locking tab 331. In an example embodiment, the distal housing 320 can include a drive shaft 321. In an example embodiment, the suture locking housing 330 and the suture locking tab 331 can be detached from the distal housing 320. Further, in an example embodiment, the suture 309 may pass through the suture locking housing 330 at a particular angle (e.g., 20° to 35°). Further, the suture locking tab 331 can also be inserted into the suture locking housing 330. In an example embodiment, after the suture locking tab 331 is inserted into the suture locking housing 330, the geometry inside of the suture locking housing 330 forces the suture 309 to make a series of tight bends. In an example embodiment, the linear motion of the suture locking tab 331 generate the tight bends in the suture 309, which requires low force to lock the lock but generates high slip force thus preventing the suture 309 from slipping out of the locked assembly of the suture locking housing 330 and the suture locking tab 331. In addition to the compression fit described above, corresponding mechanical features of the suture locking tab and suture locking housing secure the components together (see FIGS. 8K-8L).

In an example embodiment, the suture locking tab 331 can be attached to the suture locking housing 330 after the pusher tube 308 is released in the distal direction, e.g., during deployment of the suture lock. In an example embodiment, a suture lock can be deployed via the interaction of the deployment spring 302, the spring sleeve 303, the stepped washer 304, the safety button 305, the pusher 306, the release button 307, the pusher tube 308, and the catheter tube 310 in the suture lock deployment device 300. For example, assuming the safety button 305 is maintained in an "off" position, a user can selectively transfer a pushing force from the deployment spring 302 to the suture locking tab 331 by engaging the release button 307. Specifically, after the release button 307 is engaged (e.g., pressed), the deployment spring 302, which is a compression spring, decompresses and, therefore, exerts a pushing force in the distal direction. In an example embodiment, the pushing force from the decompression of the deployment spring 302 is transmitted to the suture lock via the pusher tube 308 through the catheter tube 310. Further, as depicted in the figure, after the suture lock is deployed, the suture locking tab 331 can be attached to the suture locking housing 330 to begin the crimping of the suture 309.

Figure 8C:
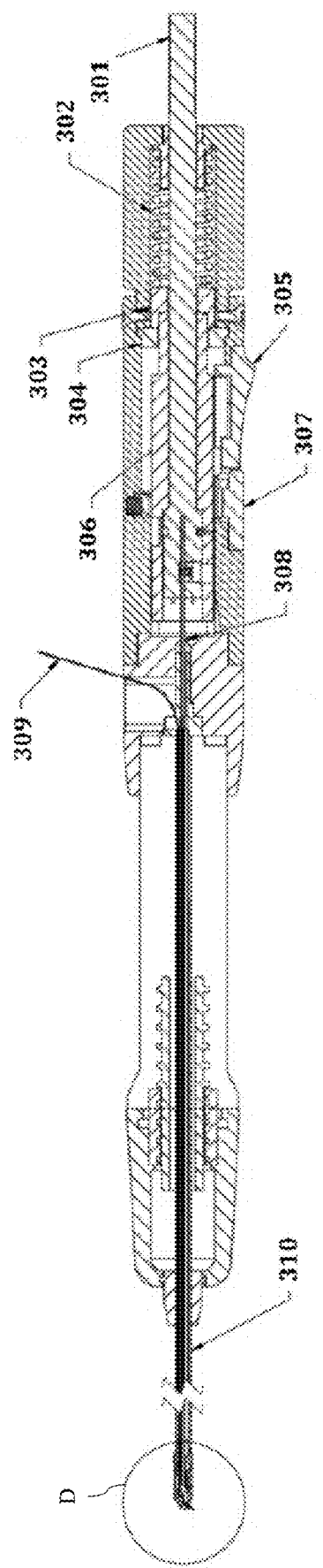
FIGS. 8C-8D show another configuration of the suture lock deployment mechanism in FIG. 8A in accordance with an example embodiment of the present invention.
Figure 8D:
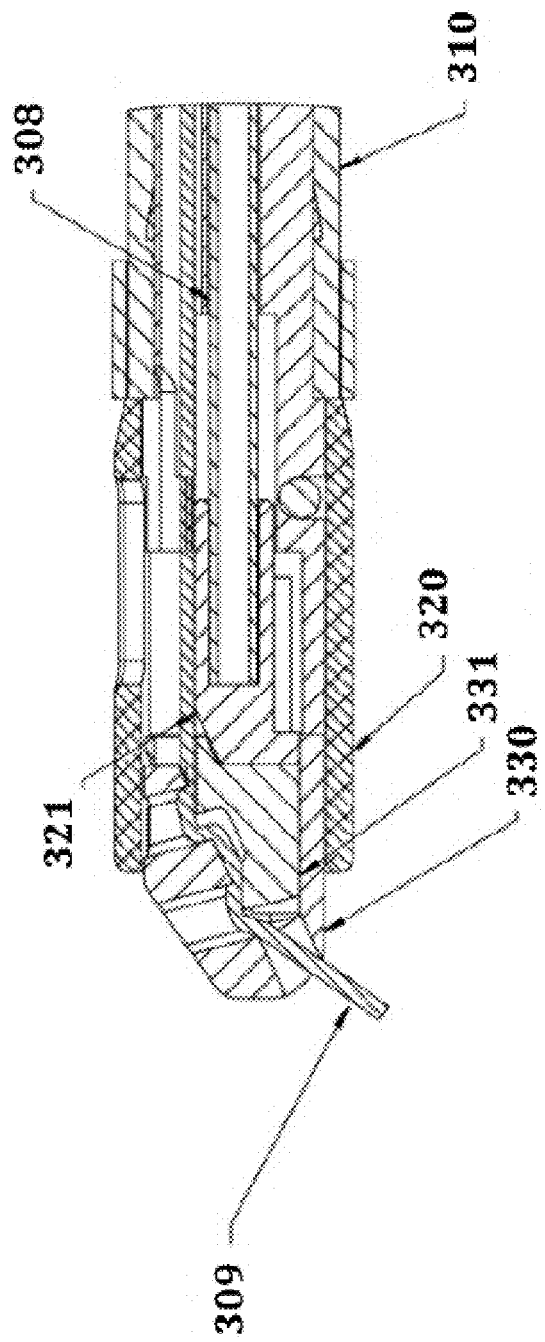

FIGS. 8C-8D show another configuration of the anchor deployment mechanism in FIGS. 8A-8B in accordance with an example embodiment of the present invention. In particular, FIG. 8C shows the suture lock deployment device 300 as the suture 309 is being crimped by the attachment of the suture locking tab 331 to the suture locking housing 330.

Figure 8E:
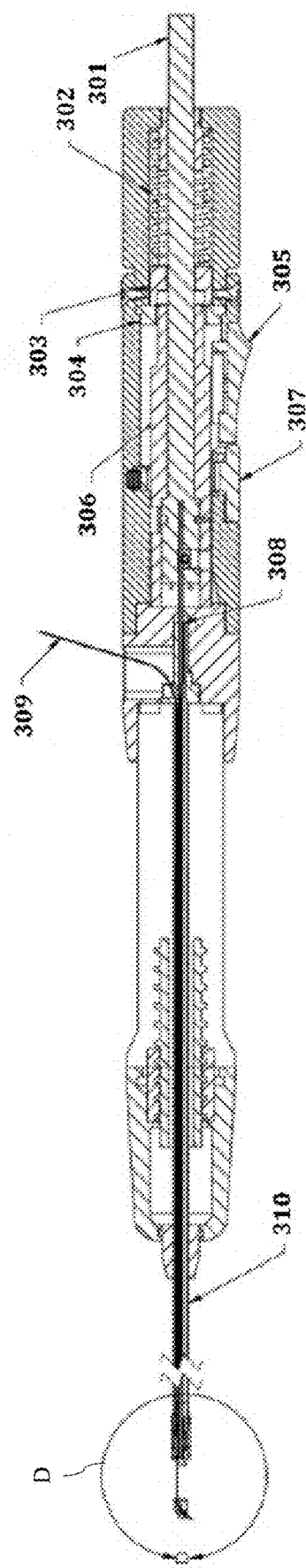
FIGS. 8E-8F show another configuration of the suture lock deployment mechanism in FIG. 8A in accordance with an example embodiment of the present invention.
Figure 8F:
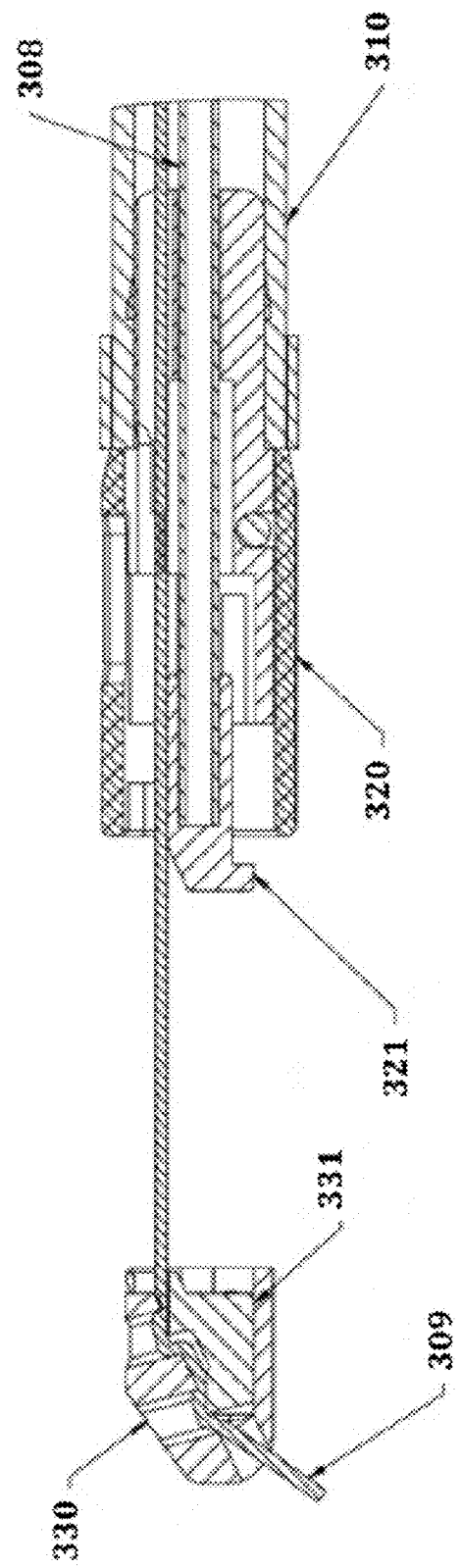
Figure 8H:
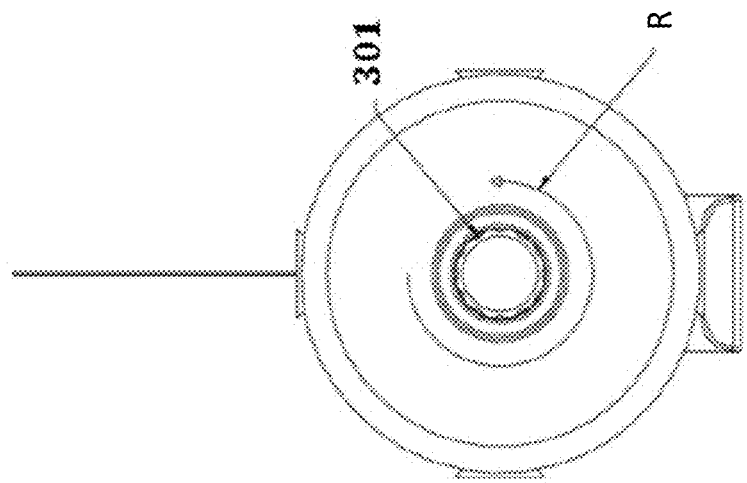
FIGS. 8G-8H show another configuration of the suture lock deployment mechanism in FIG. 8A in accordance with an example embodiment of the present invention.
Figure 8G:
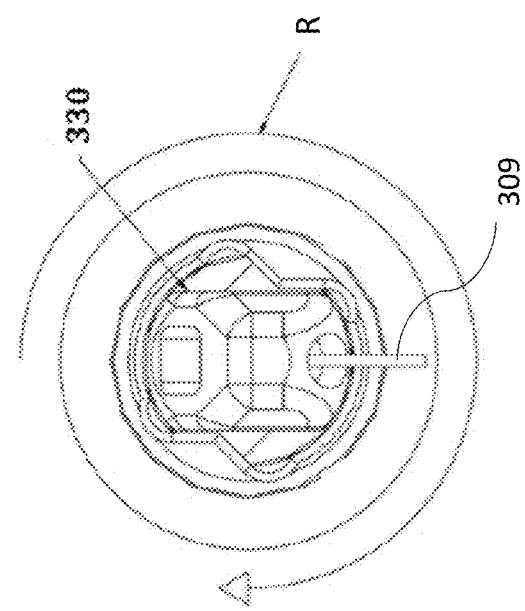
Figure 8J:
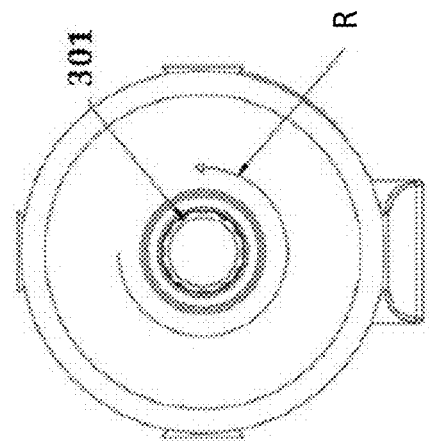
FIGS. 8I-8J show another configuration of the suture lock deployment mechanism in FIG. 8A in accordance with an example embodiment of the present invention.
Figure 8I:
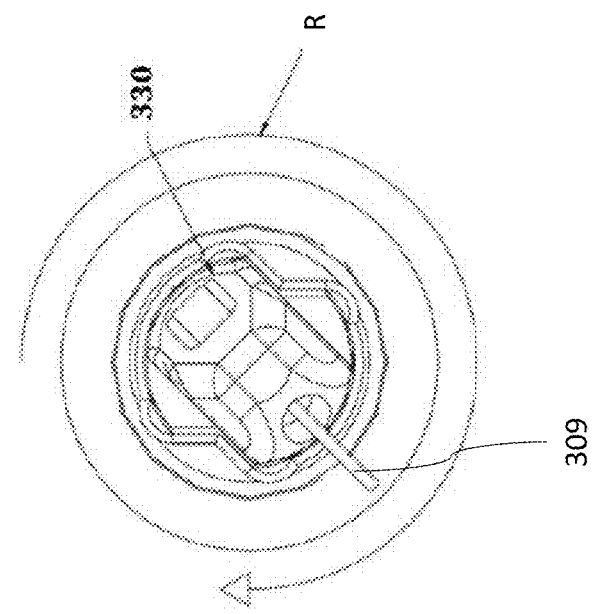

FIGS. 8E-8F show another configuration of the suture lock deployment mechanism in FIGS. 8A-8B in accordance with an example embodiment of the present invention. In particular, FIGS. 8E-8F show the suture lock housing 330 and the suture locking tab 331 being detached from the distal housing 320. In an example embodiment, the suture lock housing 330 and the suture locking tab 331 can be detached from the distal housing 320 by rotating the release shaft 301 from the proximal end of the handle of the suture lock deployment device 300 as depicted in FIGS. 8G, 8H, 8I and 8J. In an example embodiment, FIGS. 8G-8H show the suture lock housing 330 and the suture locking tab 331 assembly before the release shaft 301 is rotated. FIGS. 8I-8J shows the suture lock housing 330 and the suture locking tab 331 assembly after the release shaft 301 is rotated in the direction noted by the arrow R. In an example embodiment, the suture lock housing 330 the suture locking tab 331 assembly may be detached from the distal housing 320 after the suture lock housing 330 and the suture locking tab 331 are rotated 45°. In an example embodiment, the release shaft 301 can be rotated in a counter-clockwise rotation as depicted in FIGS. 8G, 8H, 8I and 8J. FIGS. 8G and I are end view seen from the distal end of the suture lock deployment device 300. FIGS. 8H and 8J are end view seen from the proximal end of the suture lock deployment device 300.

Figure 8K:
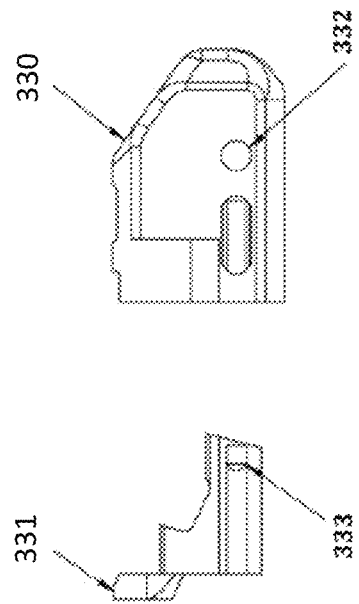
FIGS. 8K-8L show another configuration of the suture lock deployment mechanism in FIG. 8A in accordance with an example embodiment of the present invention.
Figure 8L:
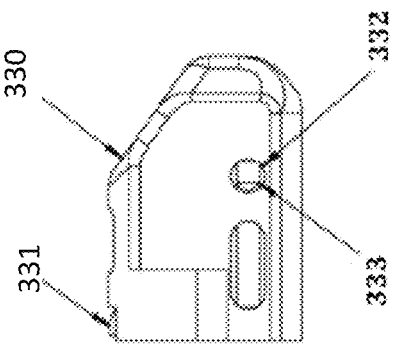
Figure 8M:
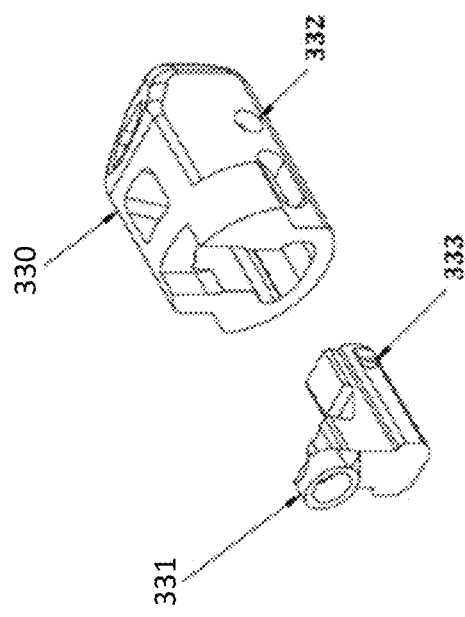
FIGS. 8M-8N show another configuration of the suture lock deployment mechanism in FIG. 8A in accordance with an example embodiment of the present invention.
Figure 8N:
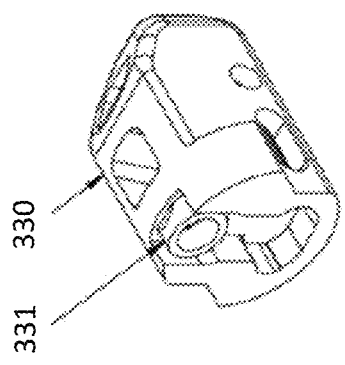

FIGS. 8K, 8L, 8M, and 8N illustrate perspective and side views of the suture lock housing 330 and the suture locking tab 331, with FIGS. 8K-8L illustrating the suture lock housing 330 and the suture locking tab 331 in an un-locked state corresponding to FIGS. 8A-8B, and FIGS. 8M-8N illustrating the suture lock housing 330 and the suture locking tab 331 in a locked state corresponding to FIGS. 8C, 8D, 8E, and 8F. In an exemplary embodiment, the suture lock housing 330 and the suture locking tab 331 are held together with the aid of a receptacle 332 and a retention feature 333. The retention feature 333 may be a tab or other extension from the suture locking tab 331, which may be compressed as the suture locking tab 331 is inserted into the suture lock housing 330, and which may expand when the retention feature reaches the receptacle 332, to resist separation of the suture lock housing 330 and suture locking tab 331. Alternatively, the retention feature 333 may be situated on the suture lock housing 330, and the receptacle 332 on the suture locking tab 331. To release or separate the suture locking tab 331 from the suture lock housing 330, the retention feature may be compressed to slide from receptacle 332.

Figure 9A:
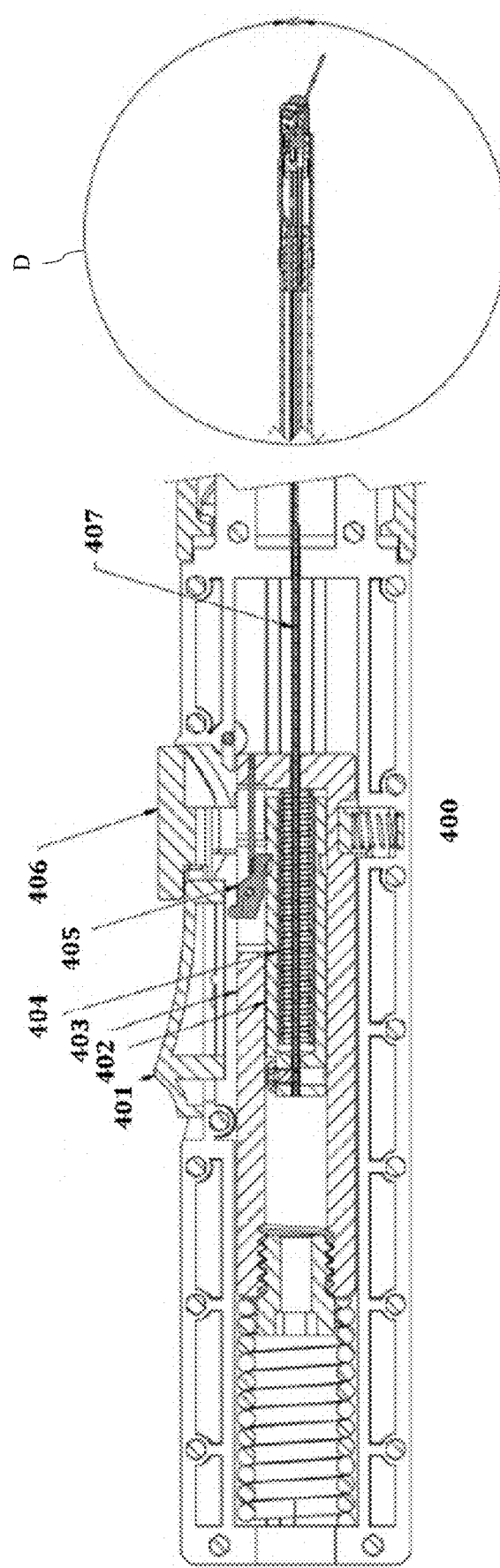
FIGS. 9A-9B show an suture lock deployment mechanism in accordance with an example embodiment of the present invention.
Figure 9B:
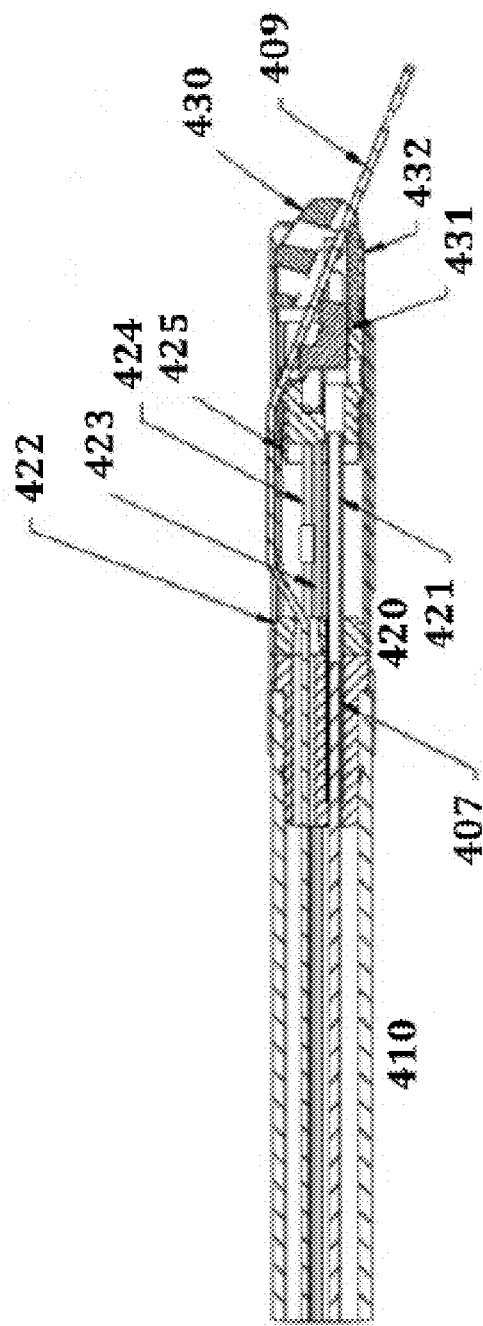

FIGS. 9A-9B shows a suture locking mechanism in accordance with an example embodiment of the present invention. As depicted in the FIG., suture locking mechanism 400 can include a safety button 401, a pin retractor 402, a pusher 403, a pin retractor spring 404, a pawl 405, a release button 406, a pusher wire 407, a suture 409, a catheter tube 410, a distal housing 420, a suture locking housing 430, a suture locking tab 431, and an actuator 432. In an example embodiment, the distal housing 420 includes a support tube 421, a cutting block 422, a suture cutting control wire 423, a suture lock control wire 424, and a suture cutting blade 425.

In an example embodiment, the elements within the suture locking mechanism 400 are configured to lock and hold a suture after deployment of an anchor (not shown) into tissue. For example, if the safety button 401 is maintained in an "off" position, a user can selectively transfer a pushing force from the pusher 403, via the pusher wire 407, to the suture locking tab 431 by engaging the release button 406. However, as depicted in the figure, the safety button 401 is maintained in an "on" position, thereby preventing the user from engaging the release button 406 and, thus, the deployment of the suture locking tab 431. Further, in an example embodiment, the pusher wire 407 may be retracted back into the suture locking mechanism 400 with the pin retractor 402 and the corresponding pin retractor spring 404. In particular, the pin retractor 402 can retract the pusher wire 407 after the pawl 405, which maintains the position of the pin retractor 402, is tripped. As such, if the pawl 405 is not tripped, then the pin retractor 402 will remain in connection with the pawl 405 and, therefore, not cause the pusher wire 407 to retract.

Further, in an example embodiment, the suture locking housing 430 and the suture locking tab 431 can be detached from the distal housing 420. In an example embodiment, the suture 409 may pass through the suture locking housing 430 at a particular angle (e.g., 20° to) 35°). Further, the suture locking tab 431 can also be inserted into the suture locking housing 430. In an example embodiment, after the suture locking tab 431 is inserted into the suture locking housing 430, a geometry inside of the suture locking housing 430 forces the suture 409 into a series of tight bends. In an example embodiment, the linear motion of the suture locking housing 430 generates the tight bends in the suture 409, which requires low force to lock but generates high slip force.

Figure 9C:
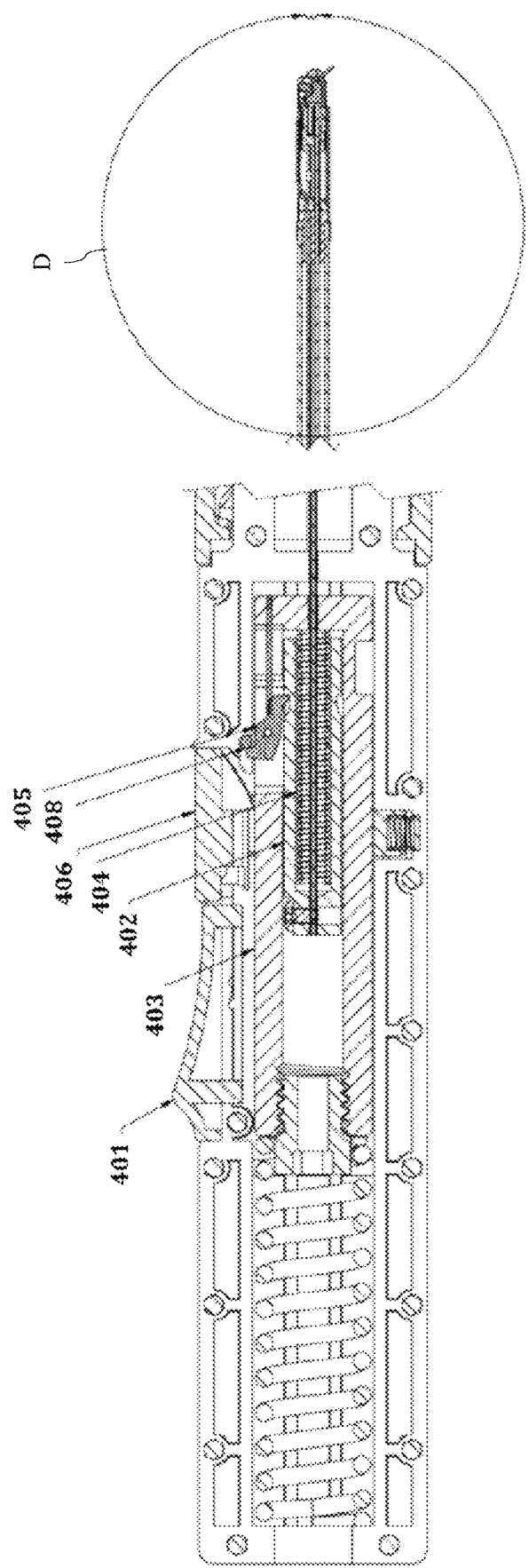
FIGS. 9C-9D show another configuration of the suture lock deployment mechanism in FIG. 9A in accordance with an example embodiment of the present invention.
Figure 9D:
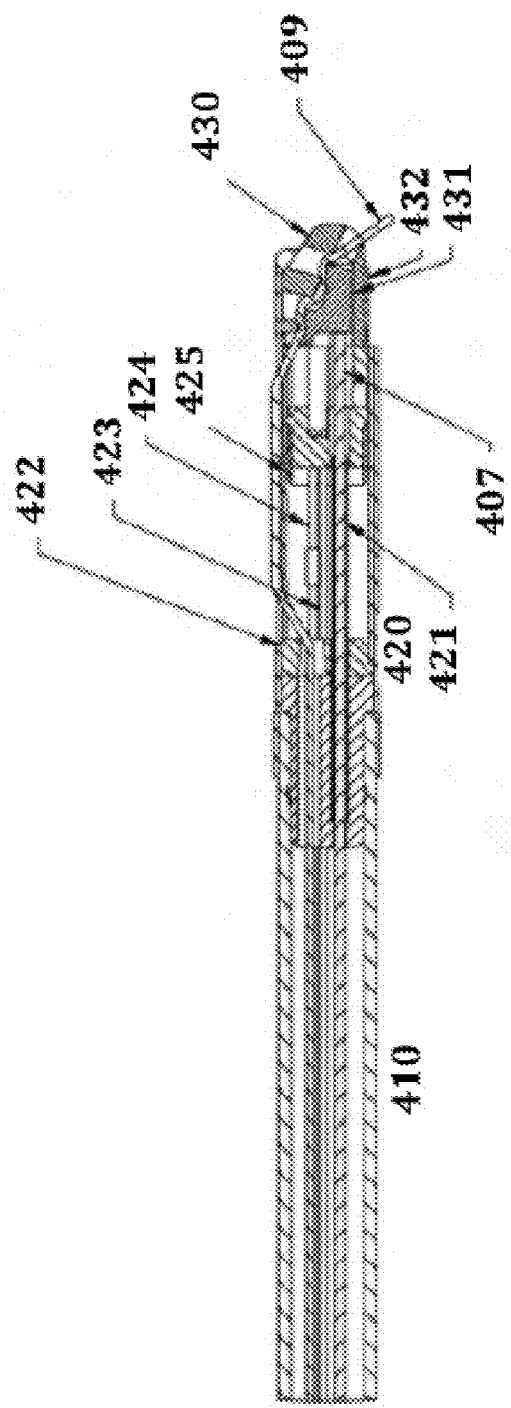

FIGS. 9C-9D show another configuration of the suture locking mechanism in FIGS. 9A-9B in accordance with an example embodiment of the present invention. In particular, FIGS. 9C-9D show the suture locking mechanism 400 with the safety button 401 in an "off" position, thereby allowing the user to engage the release button 406 to transfer a pushing force from the pusher 403 to a suture locking tab 431. Specifically, after the release button 406 is engaged (e.g., pressed), the release button 406 disengages from a notch in the pusher 403, thereby allowing the pusher 403 to exert a pushing force in the distal direction. In an example embodiment, the pushing force from the pusher 403 is transmitted to the anchors via the pusher wire 407. In another example embodiment, the pushing force exerted on the suture locking tab 431 may be imparted by other electrical, mechanical, or hydraulic operation. Further, after deployment of the suture locking tab 431, the pawl 405 may contact a pin 408. Further, as depicted in the figures, after the suture locking tab 431 is deployed, the suture lock housing 430 can begin crimping the suture 409. This figure illustrates an intermediate stage, as the pusher 403 depicted in this figure has not reached full travel.

Figure 9E:
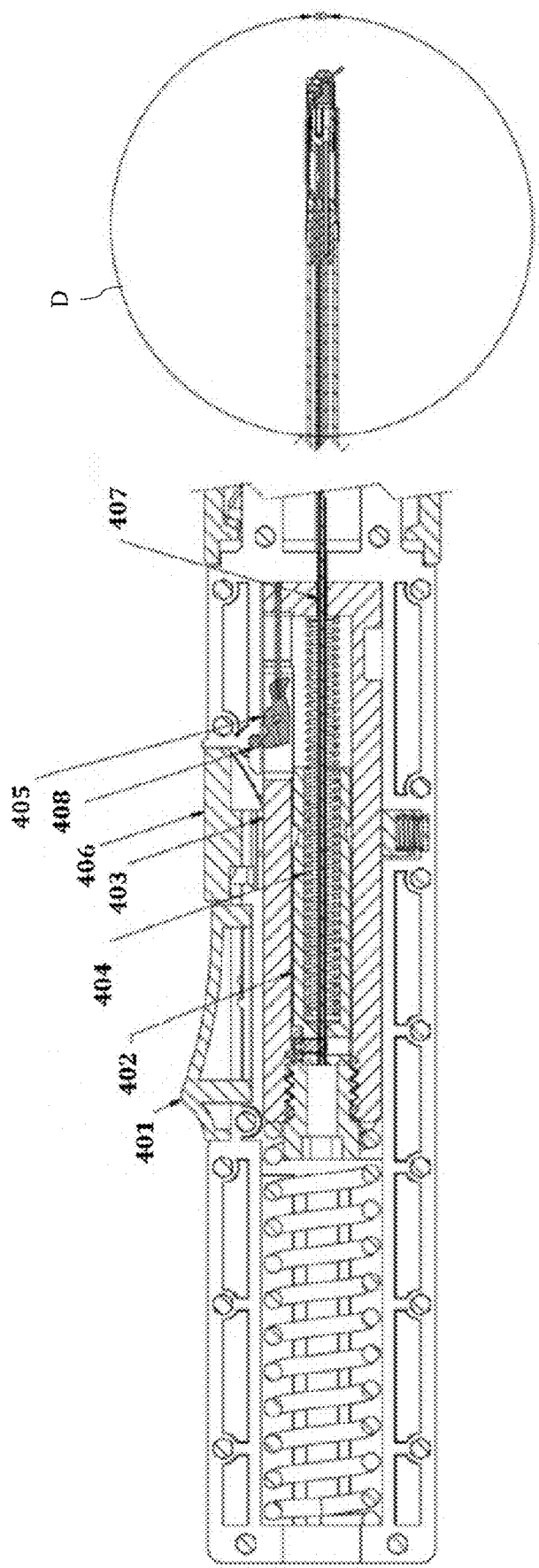
FIGS. 9E-9F show another configuration of the suture lock deployment mechanism in FIG. 9A in accordance with an example embodiment of the present invention.
Figure 9F:
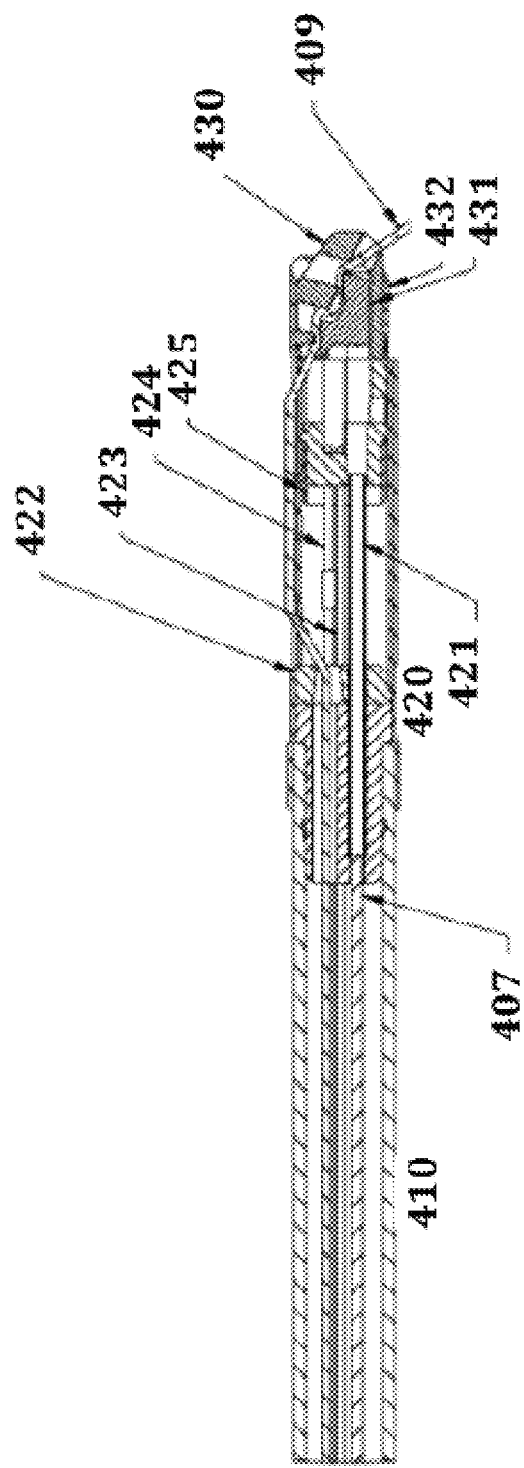

FIGS. 9E-9F show another configuration of the suture locking mechanism in FIGS. 9A-9B in accordance with an example embodiment of the present invention. In particular, FIGS. 9E-9F show the suture locking mechanism 400 after the pawl 405 is tripped by the pin 408, and the pusher 403 has reached full travel. As depicted in the figures, after the pawl 405 is tripped, the pin retractor 402 is released from the pawl 405's grip, which causes the corresponding pin retractor spring 404 to extend in the proximal direction. In an example embodiment, the extension of the pin retractor spring 404 in the proximal direction causes the pin retractor 402 to also move in the proximal direction. Further, because the proximal end of the pusher wire 407 is attached to the proximal end of the pin retractor 402, the pusher wire 407 is pulled (i.e., retracted) in the proximal direction.

FIGS. 9G, 9H, 9I, 9J, 9K, and 9L show additional configurations of the suture locking mechanism in FIGS. 9A-9B in accordance with an example embodiment of the present invention. In particular, once the suture has been locked into suture locking housing 430, FIGS. 9G, 9H, 9I, 9J, 9K, and 9L illustrate control knobs for releasing the suture lock from the distal housing, and for cutting the suture. The control knob for releasing the suture lock may be situated adjacent to the control knob for cutting the suture, so that the release of the suture lock and the cutting of the suture can be easily achieved in simple, similar motions.

Figure 9H:
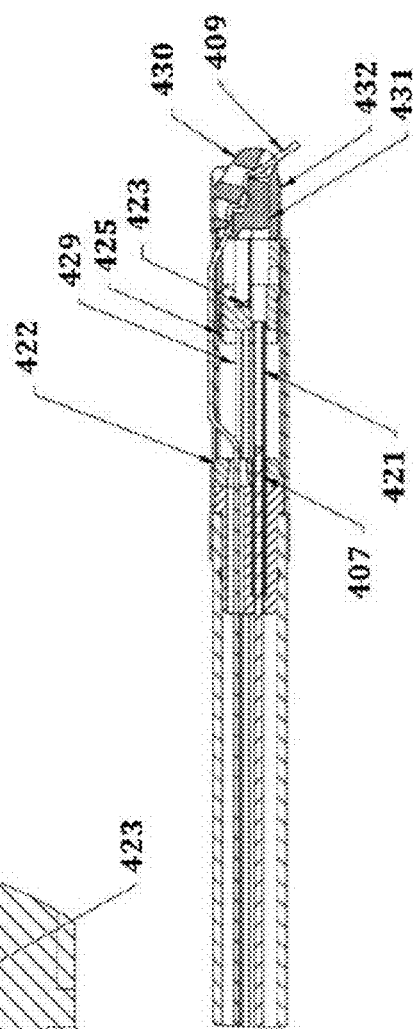
FIGS. 9G-9H show another configuration of the suture lock deployment mechanism in FIG. 9A in accordance with an example embodiment of the present invention.
Figure 9G:
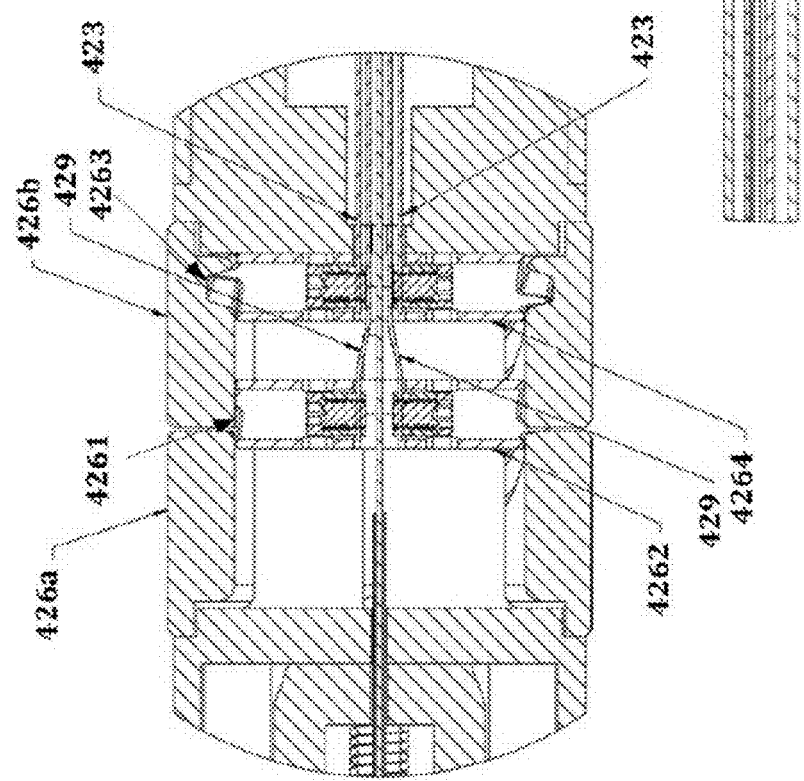

FIGS. 9G-9H show the suture locking mechanism 400 before the suture lock housing 430 and the suture locking tab 431 is detached from the distal housing 420. FIGS. 9G-9H also depicts a cross section of a suture lock control knob 426, which includes the suture cutting control wire 423 and a suture lock release wire 429. Suture lock control knob 426a includes suture lock threading 4261, which interacts with suture lock screw 4262, such that a turning of the suture lock control knob 426a translates the suture lock screw 4262 in the proximal or distal directions. By drawing the suture lock screw in the proximal direction, suture lock release wire 429 is drawn in the proximal direction, pulling the actuator 432 from around the suture lock to release the suture lock from the distal housing.

Figure 9I:
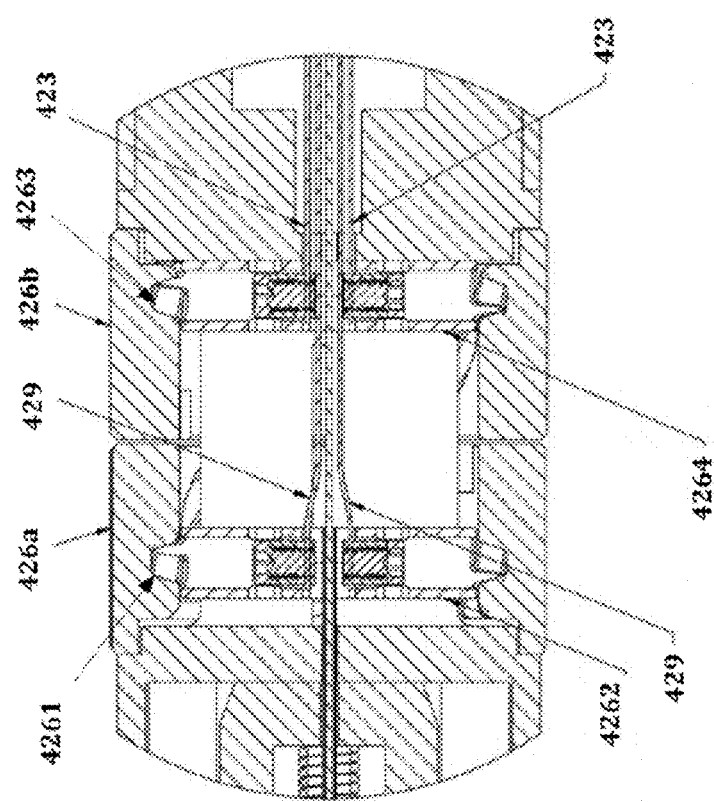
FIGS. 9I-9J show another configuration of the suture lock deployment mechanism in FIG. 9A in accordance with an example embodiment of the present invention.
Figure 9J:
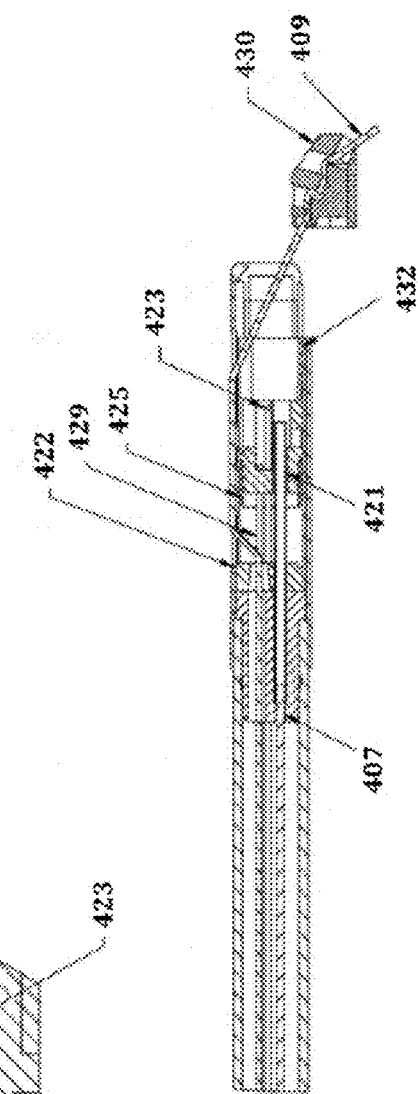

FIGS. 9I-9J shows the suture locking mechanism 400 after the suture lock housing 430 and the suture locking tab 431 is detached from the distal housing 420. The suture lock control knob 426a has been turned, translating suture lock screw 4262 in the proximal direction, drawing on suture lock release wire 429 to release the suture lock housing 430. In an example embodiment, the suture lock housing 430 and the suture locking tab 431 can be detached from the distal housing 420 after the actuator 432 is moved in the proximal direction. In particular, detachment may occur after the actuator 432 is no longer underneath the suture lock housing 430 and the suture locking tab 431. In FIGS. 9I-9J, the suture cutting control knob 426b has not yet been turned, so that suture cutting screw 4264 and remains in the distal position. The suture cutting control knob 426b includes suture cutting threading 4263, which interacts with suture cutting screw 4264, such that a turning of the suture cutting control knob 426b translates the suture cutting screw 4264 in the proximal or distal directions. By drawing the suture cutting screw in the proximal direction, suture cutting control wire 423 is drawn in the proximal direction, as is the suture cutting blade 425. When suture cutting blade 425 is drawn sufficiently in the proximal direction, the blade 425 meets suture 409 and cutting block 422, and presses against suture 409 with sufficient force to cut the suture. The suture lock control knob and the suture cutting control knob may instead be combined into one control knob, which first turns to release the suture lock, and then turns again to cut the suture.

Figure 9L:
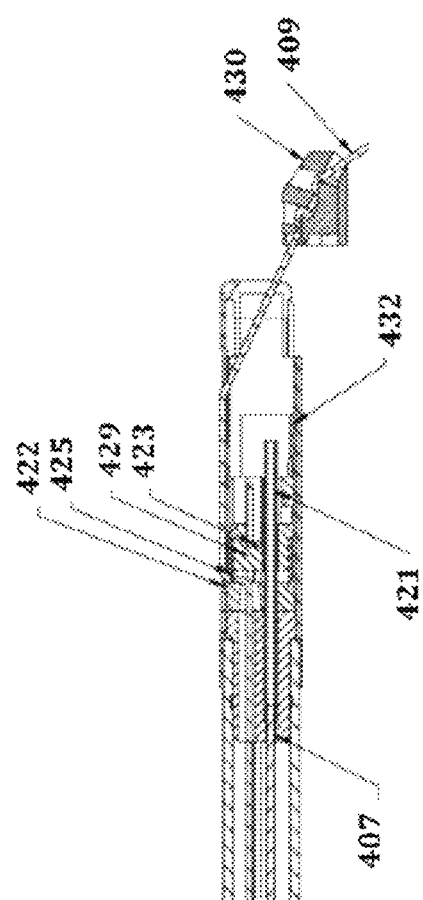
FIGS. 9K-9L show another configuration of the suture lock deployment mechanism in FIG. 9A in accordance with an example embodiment of the present invention.
Figure 9K:
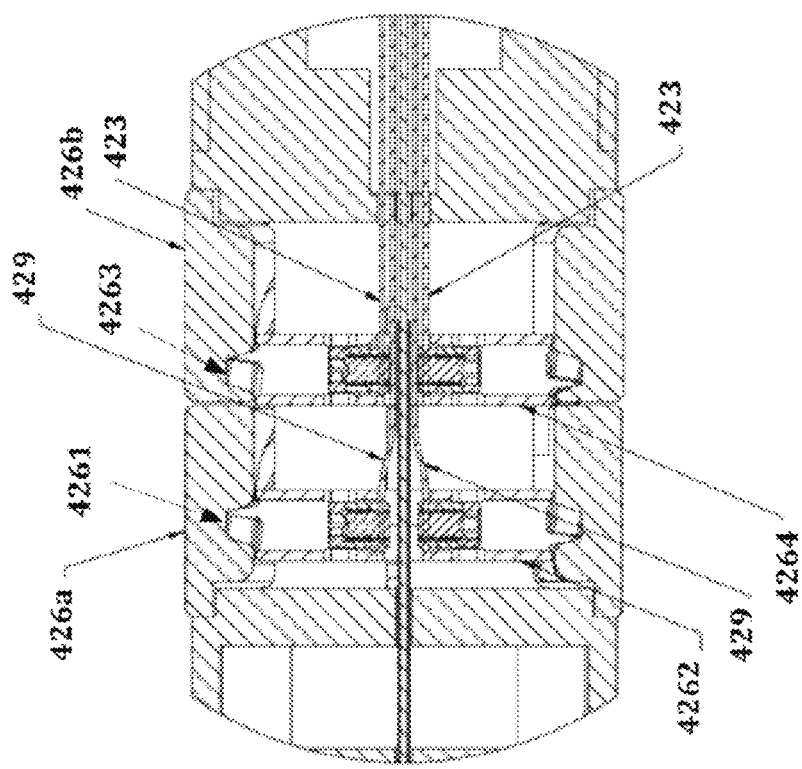

FIGS. 9K-9L shows the suture locking mechanism 400 after the suture 409 is cut by the suture cutting blade 425. The entire implant, including the anchors, the suture, and the suture lock, is now free of the surgical device, and may remain at the surgical site.

Figure 10E:
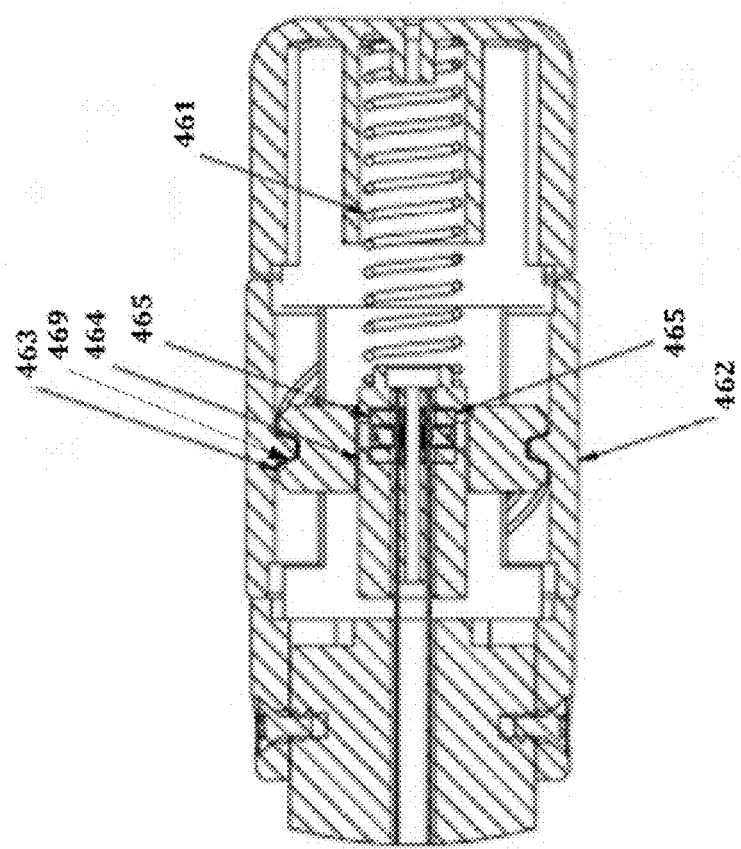
FIGS. 10D-10E show a cross sectional view of the suture cutting mechanism of FIG. 10A.
Figure 10D:
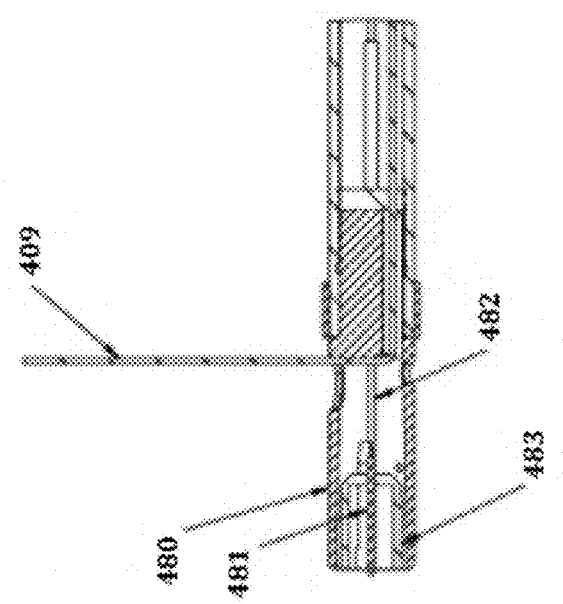
Figure 10G:
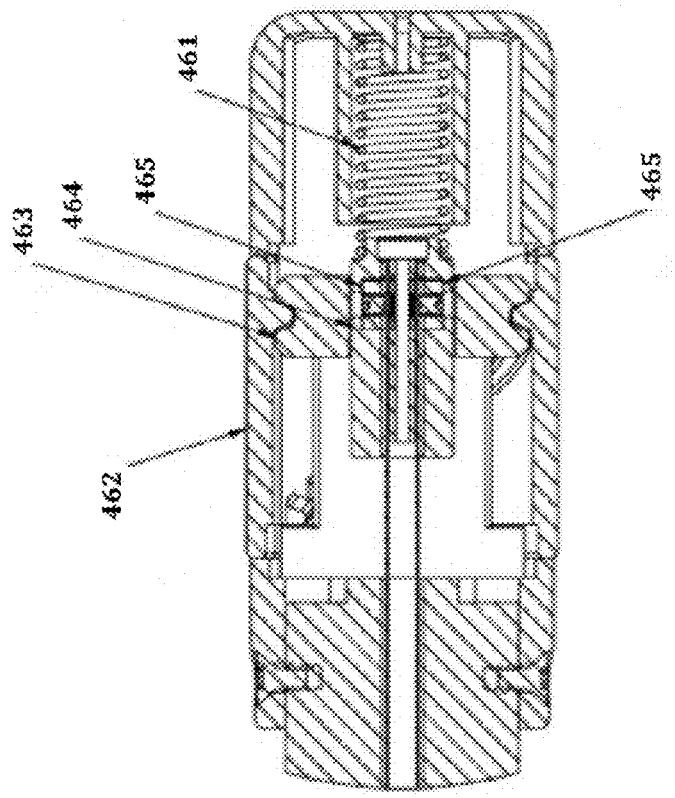
FIGS. 10F-10G show a cross sectional view of the suture cutting mechanism of FIG. 10A.
Figure 10F:
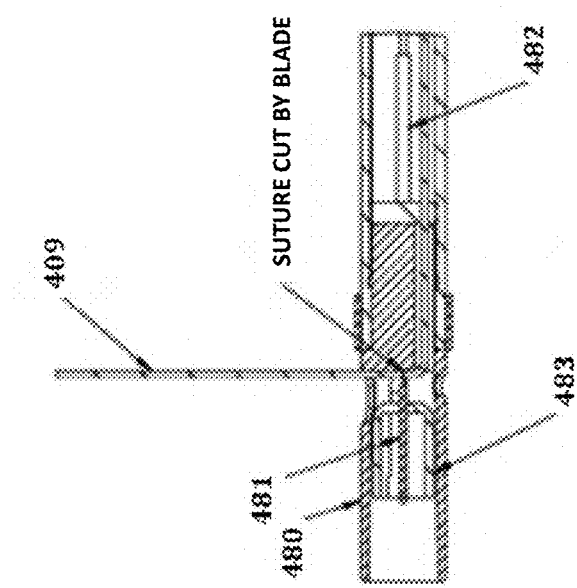

A further embodiment of the suture cutting mechanism is illustrated in FIGS. 10A, 10B, 10C, 10D, 10E, 10F, and 10G. FIGS. 10A, 10B, and 10C illustrate a surgical device 450 including the handle 460, catheter 470, and distal housing 480. Handle 460 includes the spring 461, suture cutting control knob 462, suture cutting screw 463, suture cutting wire mount 464, suture cutting wire clamp 465, safety 466, adapter 467, and cap 468. Distal housing 480 includes a suture cutting blade 481, suture cutting wire 482, and blade holder 483. FIGS. 10D-10E illustrate the handle 460 and the distal housing 480 in position to cut the suture 409. As illustrated in FIGS. 10D-10E, suture cutting screw 463 fits into the suture cutting threading 469, and is in a distal position within handle 460. Suture cutting wire mount 464 and suture cutting wire clamp 465 hold suture cutting wire 482 to the suture cutting screw 463. In the distal housing 480, suture cutting wire 482 is attached to blade 481, in position to cut suture 409. As illustrated in FIGS. 10F-10G, suture cutting control knob 462 has been turned, translating suture cutting screw 463 in the proximal direction, drawing suture cutting wire 482, and therefore blade 481, in the proximal direction into suture 409, cutting the suture.

Figure 11A:
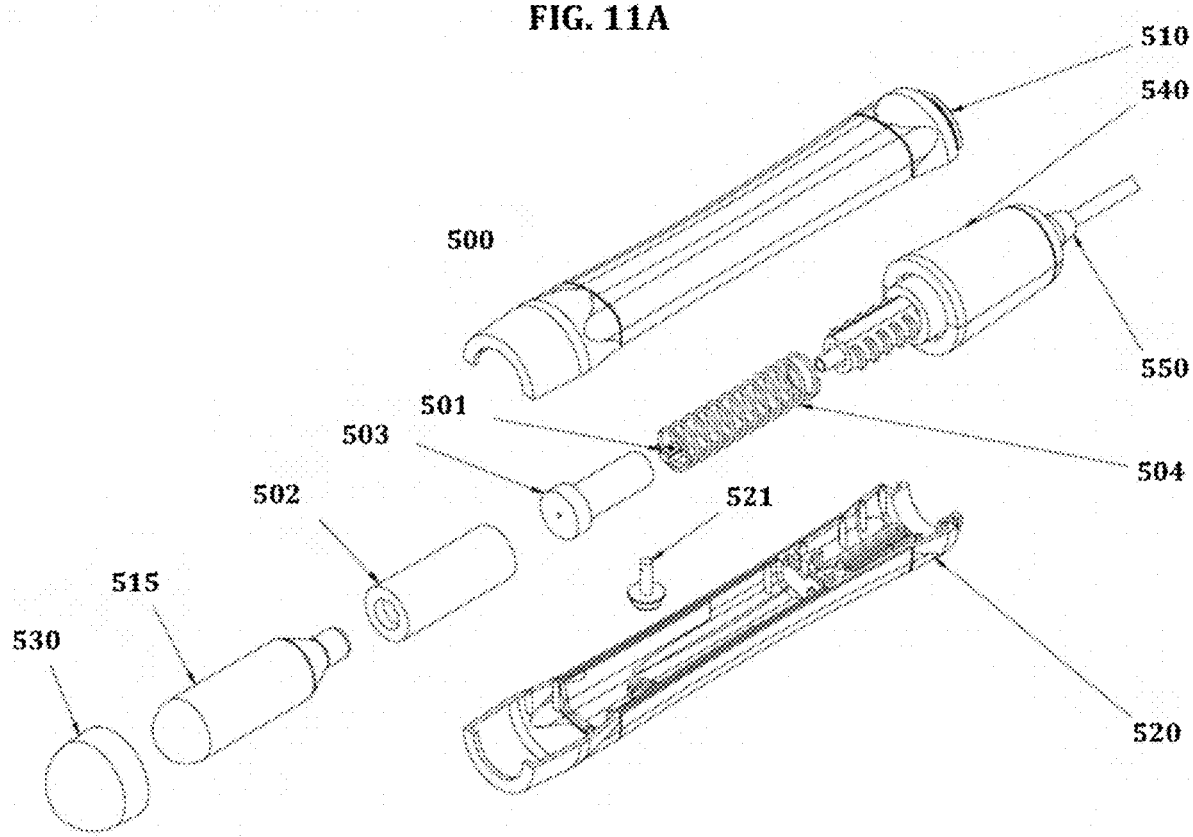
FIG. 11A shows an exploded view of an anchor deployment mechanism in accordance with an example embodiment of the present invention.

FIG. 11A shows an exploded view of an anchor deployment mechanism in accordance with an example embodiment of the present invention. As depicted in FIG. 11A, anchor deployment mechanism 500 includes an outer handle 510, a compressed gas tank 515, a trigger handle 520, a deployment button 521, a cap 530, a steering knob 540, a catheter 550, a retaining block 501, an actuation cylinder 502, a piston 503, and a return spring 504. Further, in an example embodiment, a distal end of the catheter 550 may be connected to a distal anchor housing (e.g., distal anchor housing 150 or 220) including one or more anchors.

Figure 11B:
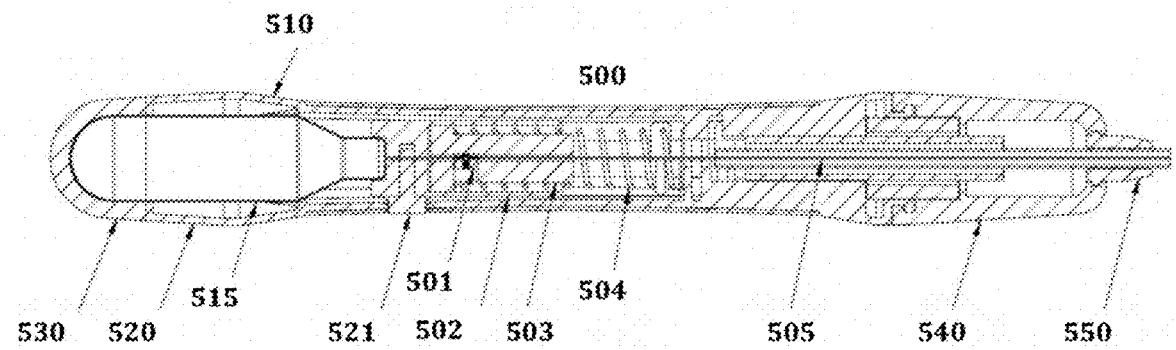
FIG. 11B shows a cross sectional view of the anchor deployment mechanism of FIG. 11A.

FIG. 11B is a cross-sectional view of the anchor deployment mechanism of FIG. 11A. As depicted in FIG. 11B, the anchor deployment mechanism 500 also includes a pusher wire 505. In an example embodiment, the elements within the anchor deployment mechanism 500 are configured to impart a pushing force on the anchor(s) in the connected distal anchor housing (not shown). Specifically, a pushing force is imparted onto the anchor(s) by the deployment of compressed gas from the compressed gas tank 515. For example, after the deployment button 521 is engaged (e.g., pressed), gas escaping from the compressed gas tank 515 and into a second closed system, e.g. a cylinder, exerts a pushing force in the distal direction. In an example embodiment, the pushing force from the released gas is transmitted to the anchors via the pusher wire 505. In an example embodiment, engaging the deployment button 521 releases gas sufficient to drive a single anchor into tissue. In another example embodiment, engaging the deployment button 521 releases gas sufficient to drive a plurality of anchors into tissue. Further, in an example embodiment, after the anchor is driven into tissue, the return spring 504 exerts a pulling force on the pusher wire 505 in the proximal direction. Accordingly, the pusher wire 504 is brought back to its original position and, therefore, the anchor deployment mechanism 500 can be utilized to drive additional anchors into tissue. In an example embodiment, the compressed gas tank 515 is disposable and replaceable. Further, in another example embodiment, carbon dioxide or a similar gas may be used to exert the pushing force on the anchors.

FIG. 12A shows an exploded view of an anchor deployment mechanism in accordance with an example embodiment of the present invention. As depicted in FIG. 12A, anchor deployment mechanism 600 includes an outer handle 610, a motor 615, a deployment button 621, a cap 630, an actuation shaft 602, and a pusher wire clamp 603. Further, in an example embodiment, a distal end of a catheter 650 may be connected to a distal anchor housing (e.g., distal anchor housing 150 or 220) including one or more anchors.

FIG. 12B is a cross-sectional view of the anchor deployment mechanism of FIG. 12A. As depicted in FIG. 12B, the anchor deployment mechanism 600 also includes a pusher wire 605. In an example embodiment, the elements within the anchor deployment mechanism 600 are configured to impart a pushing force on the anchor(s) in the connected distal anchor housing (not shown). Specifically, a pushing force is imparted onto the anchor(s) by the actuation of a motor 615. For example, after the deployment button 621 is engaged (e.g., pressed), motor 615 turns its rotor, and actuation shaft 602 is in a screw-threaded communication, such that the turning of the rotor translates to a pushing force on the actuation shaft in the distal direction. In an example embodiment, engaging the deployment button 621 presents sufficient force to drive a single anchor into tissue. In another example embodiment, engaging the deployment button 621 presents sufficient force to drive a plurality of anchors into tissue. Further, in an example embodiment, after the anchor is driven into tissue, the motor may be run in reverse, to exert a pulling force on the pusher wire 605 in the proximal direction. Accordingly, the pusher wire 605 is brought back to its original position and, therefore, the anchor deployment mechanism 600 can be utilized to drive additional anchors into tissue.

FIG. 13A shows an exploded view of an anchor deployment mechanism in accordance with an example embodiment of the present invention. As depicted in FIG. 13A, anchor deployment mechanism 700 includes an outer handle 710, a cylinder 715 housing an actuation shaft or plunger 702, a deployment button 721, a cap 730, and a set screw 703. Further, in an example embodiment, a distal end of a catheter 750 may be connected to a distal anchor housing (e.g., distal anchor housing 150 or 220) including one or more anchors.

FIG. 13B is a cross-sectional view of the anchor deployment mechanism of FIG. 13A. As depicted in FIG. 13B, the anchor deployment mechanism 700 also includes a pusher wire 705. In an example embodiment, the elements within the anchor deployment mechanism 700 are configured to impart a pushing force on the anchor(s) in the connected distal anchor housing (not shown). Specifically, a pushing force is imparted onto the anchor(s) by the actuation of an actuation shaft or plunger 702. For example, after the deployment button 721 is engaged (e.g., pressed), cylinder 715 is flooded with a hydraulic fluid, exerting a force on actuation shaft 702 in the distal direction. In an example embodiment, engaging the deployment button 721 presents sufficient force to drive a single anchor into tissue. In another example embodiment, engaging the deployment button 721 presents sufficient force to drive a plurality of anchors into tissue. Further, in an example embodiment, after the anchor is driven into tissue, the hydraulic fluid may be withdrawn from the cylinder, to exert a pulling force on the pusher wire 705 in the proximal direction. Accordingly, the pusher wire 705 is brought back to its original position and, therefore, the anchor deployment mechanism 700 can be utilized to drive additional anchors into tissue.

Figure 14A:
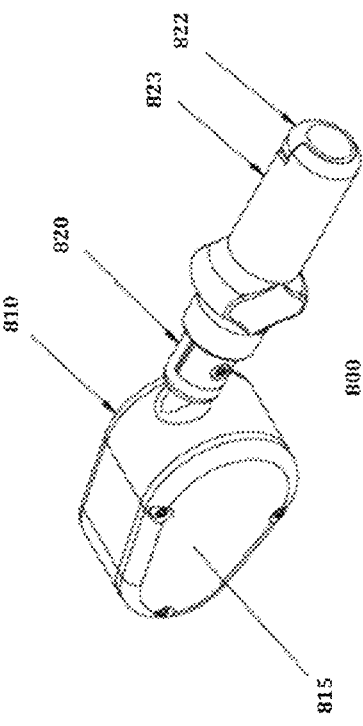
FIG. 14A shows a suture tensioner according to an exemplary embodiment of the present invention.

To ensure that the amount of force applied to an anchor already deployed in tissue during a percutaneous procedure is not too great, so as to damage the tissue, or too small, so as to allow for excess of suture in the surgical site that may become knotted or looped, a suture tensioner may be used to hold the suture. The suture tensioner 800, illustrated in FIG. 14A, can hold the suture during the surgical procedure, maintaining a constant force on the suture.

Figure 14B:
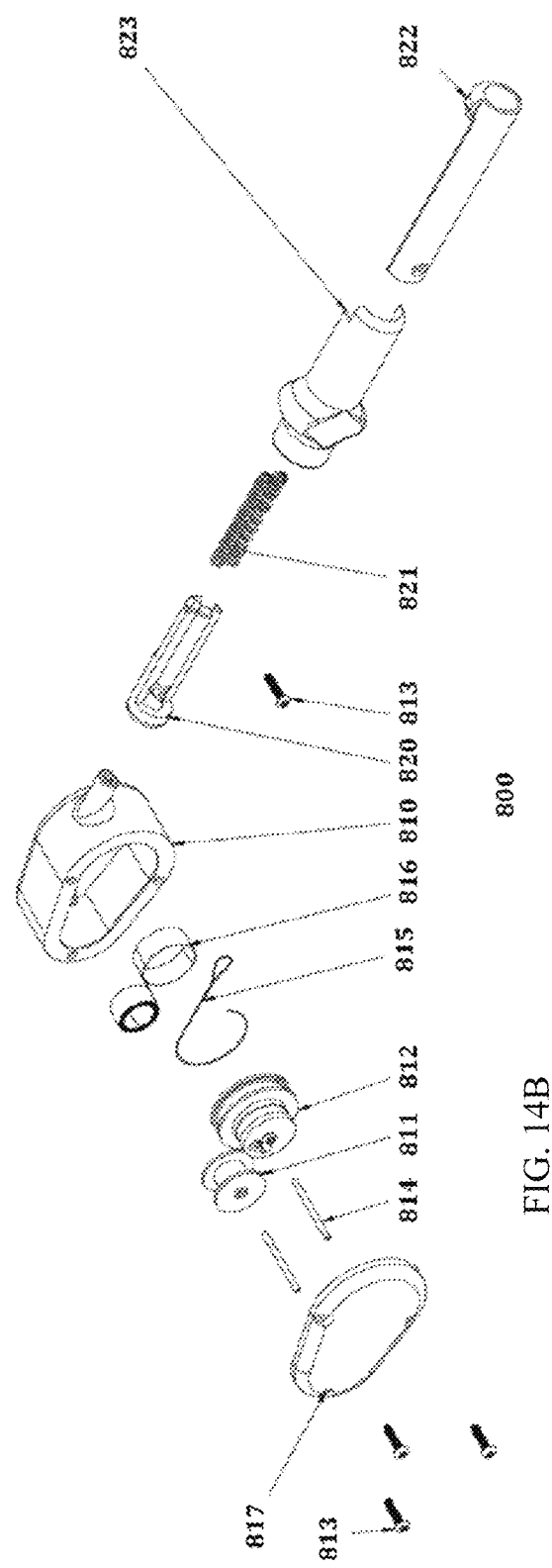
FIG. 14B shows an exploded view of the suture tensioner of FIG. 14A.

An exploded view of the suture tensioner 800 is illustrated in FIG. 14B. Suture tensioner 800 includes tensioner housing 810, spring pulley 811, suture pulley 812, screw(s) 813, dowel pin(s) 814, monofilament 815, constant force spring 816, tensioner cover 817, suture grip spring retainer 820, release button spring 821, suture grip base 822, and suture grip slide 823.

Figure 14C:
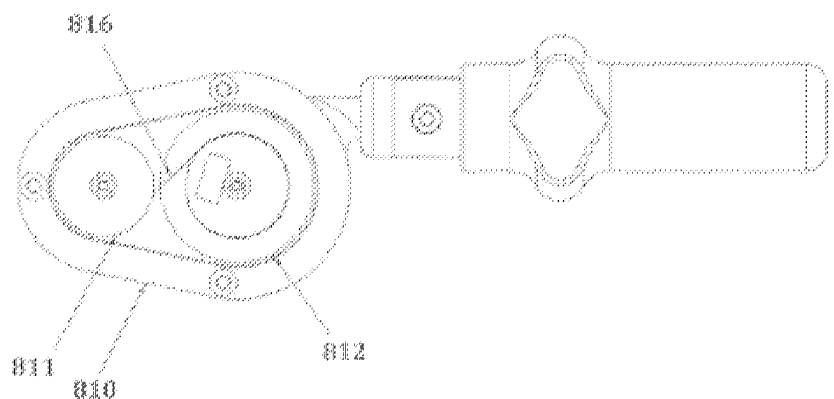
FIG. 14C shows a suture tensioner according to an exemplary embodiment of the present invention.
Figure 14D:
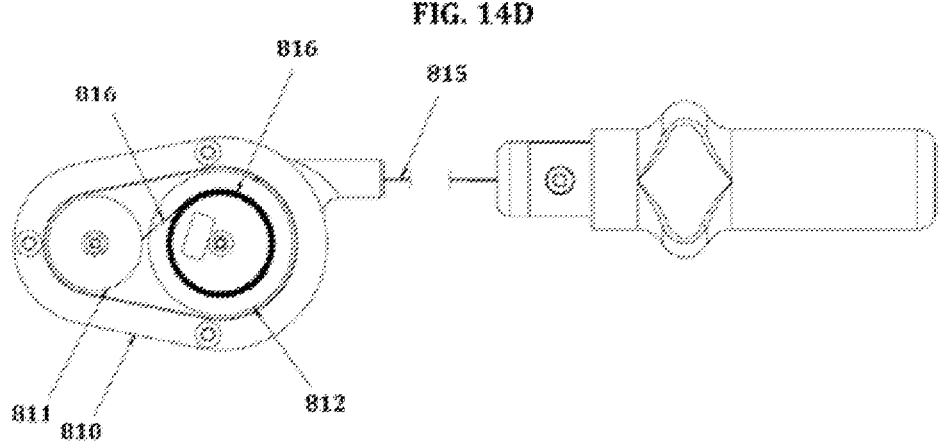
FIG. 14D shows a suture tensioner according to an exemplary embodiment of the present invention.

FIG. 14C illustrates the suture tensioner 800 in an exemplary embodiment of the present invention. The suture tensioner 800, including spring pulley 811 and suture pulley 812, is in its initial state, with no force applied. Constant force spring 816 is wrapped around the spring pulley 811. In FIG. 14D, the suture tensioner 800 is in its extended state, subject to an applied force. In this extended state, constant force spring 816 is extended from its wrapping around spring pulley 811, as monofilament 815 is drawn in the direction of suture grip slide 823 and suture grip base 822. The unwrapping of the constant force spring 816 from the spring pulley 811 provides a constant tension on the monofilament 815, which in turn provides the same constant tension on the clamped suture, as described below.

Figure 14E:
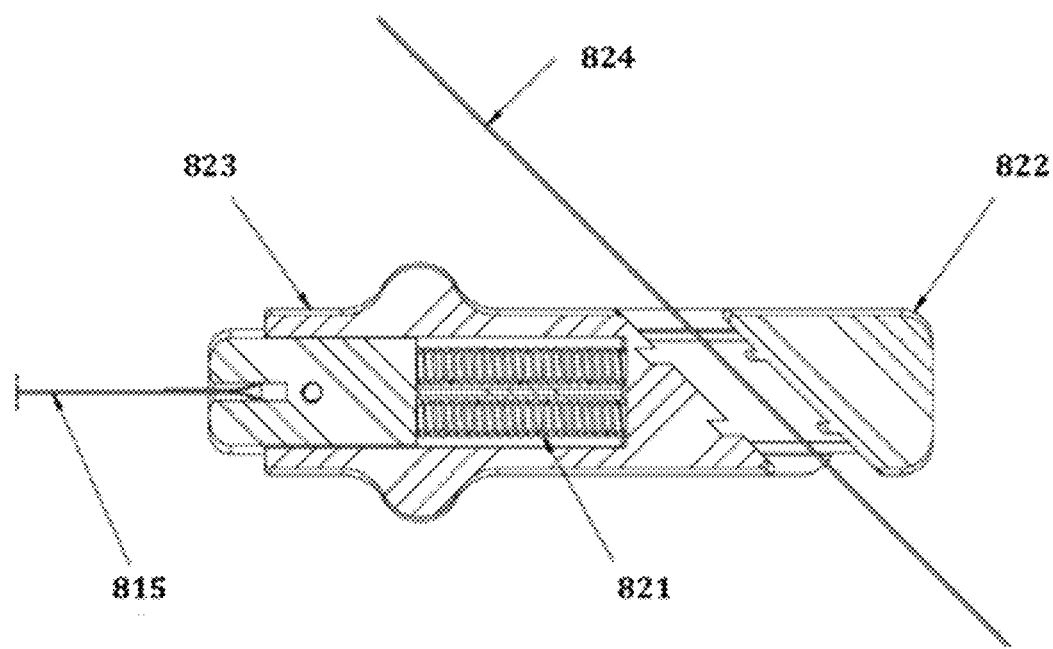
FIG. 14E shows a cross sectional view of the suture tensioner of FIG. 14A.
Figure 14F:
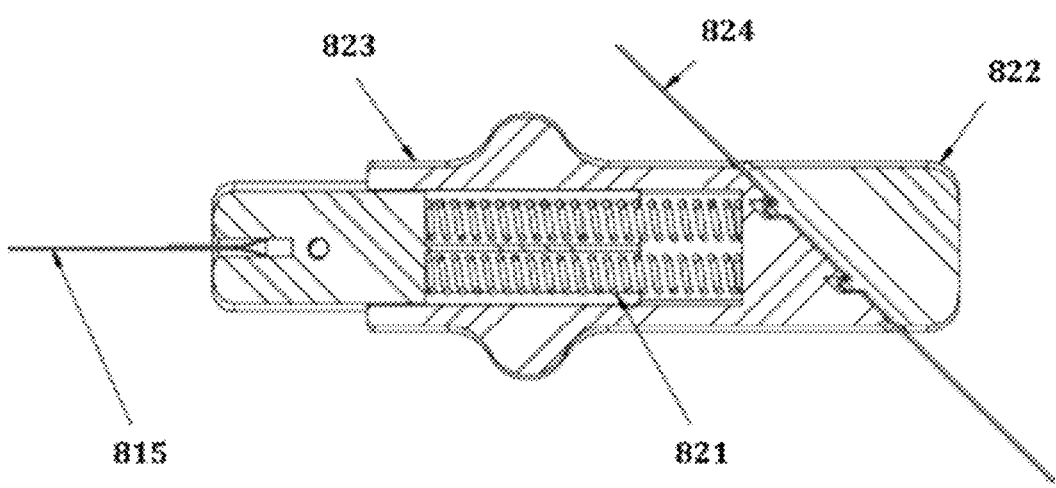
FIG. 14F shows a cross sectional view of the suture tensioner of FIG. 14A.

Clamping of the suture in the suture grip of the suture tensioner is illustrated in FIGS. 14E and 14F. In FIG. 14E, the suture clamp is open. The suture grip slide 823 has been drawn away from the suture grip base 822, compressing the release button spring 821. This slide operation may be achieved by hand during the surgical procedure. Suture 824 is then placed between the suture grip slide 823 and the suture grip base 822. In FIG. 14F, the suture grip slide 823 has been released, release button spring 821 has decompressed, pushing suture grip slide 823 into apposition with suture grip base 822. By this movement of the suture grip slide 823 to suture grip base 822, the suture clamp has been closed, and suture 824 has been clamped therein. By holding suture tensioner 800 by the tensioner housing 810, the tensioner 800 can be used to hold or manipulate suture 824, and only a constant force will be applied to the suture 824.

Figure 15:
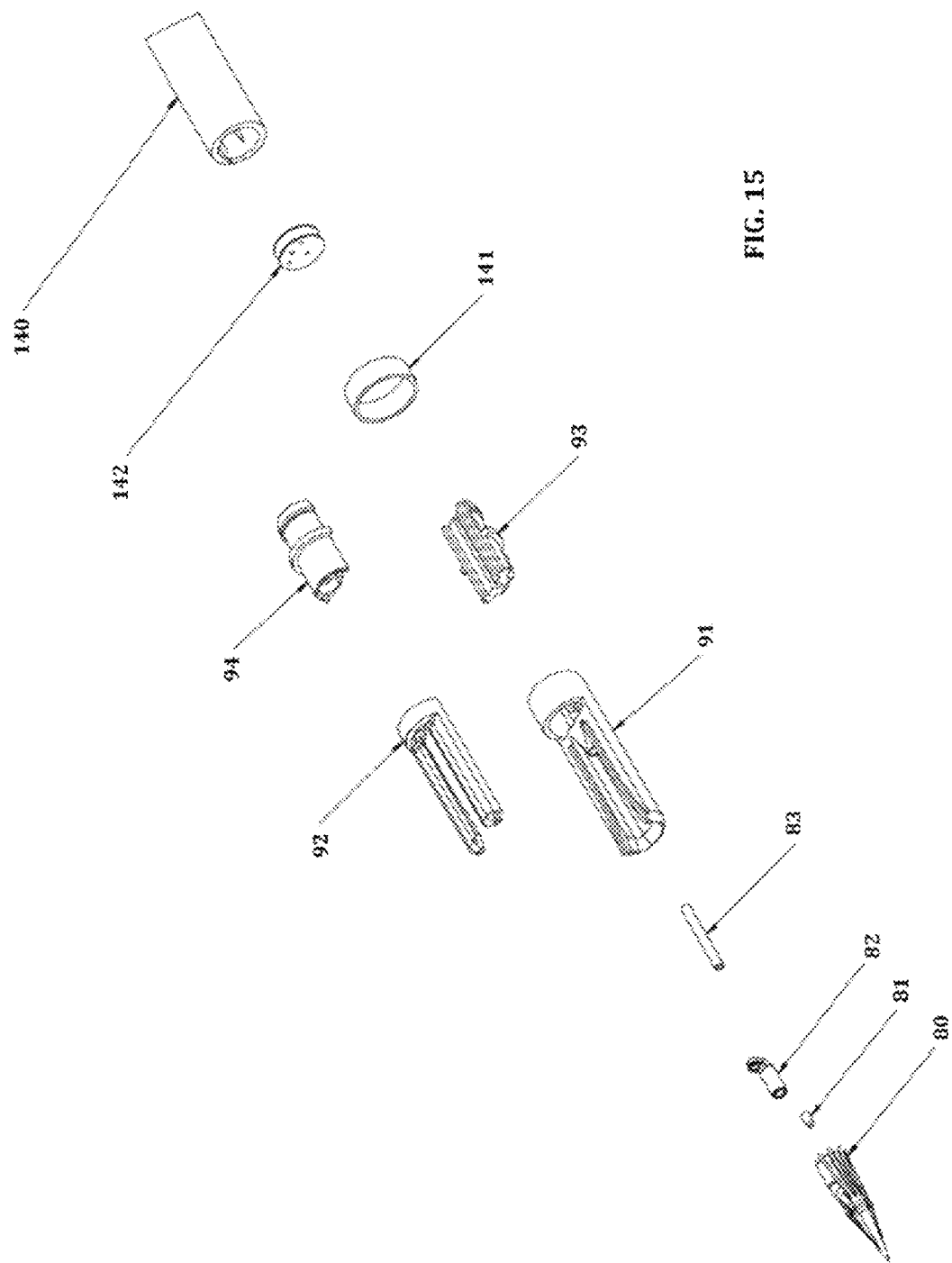
FIG. 15 shows an exploded view of an anchor deployment mechanism in accordance with an example embodiment of the present invention.

According to an exemplary embodiment of the present invention, the surgical device described herein may include a detachable reload anchor housing, to provide more rapid deployment of secondary anchors following the deployment of a primary anchor. FIG. 15 shows an exploded view of the distal end, including secondary anchor 80, anchor cup insert 81, eyelet 82, pusher wire guide tube 83, catheter 140, catheter crimp band 141, delivery device seal 142. The detachable reload anchor housing 90 may include reload base 91 and reload cap 92, and is formed to attach to, or detach from, the distal end of the surgical device, specifically with reload socket base 93, and reload socket cap 94.

Figure 16B:
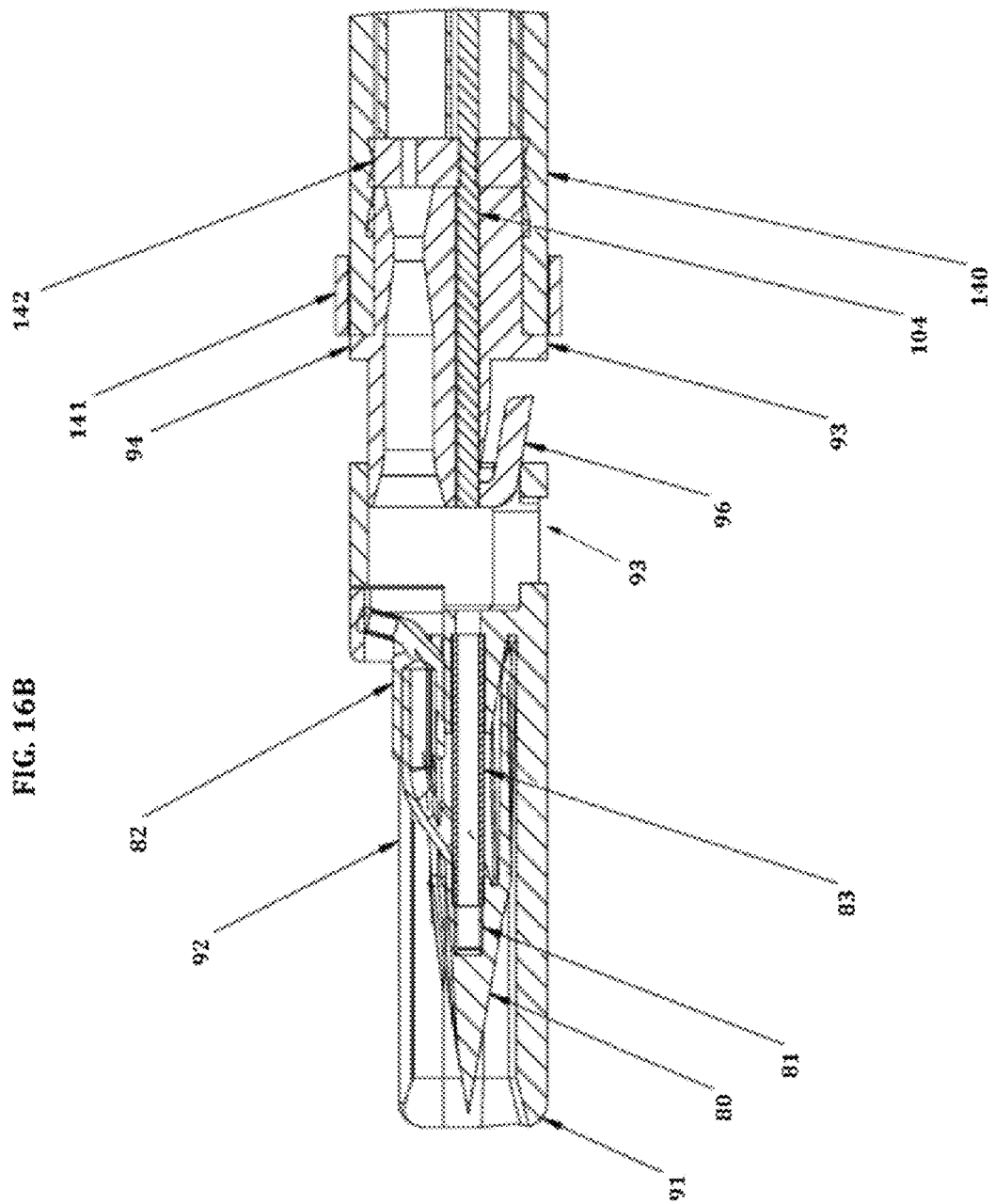
FIG. 16B shows a cross sectional view of the anchor deployment mechanism in accordance with an example embodiment of the present invention.

FIGS. 16A, 16B, and 16C show the mechanisms for installing a detachable reload anchor housing, for example, for preparing and deploying a secondary anchor. Anchor 80 is situated within the reload anchor housing 90. To attach the reload anchor housing 90 to the distal end of the surgical device, reload anchor housing is brought into apposition with reload socket base 93 and reload socket cap 94. Reload anchor housing 90 includes a notch 95. As the proximal end of reload anchor housing 90 is pressed against the distal end of reload socket base 93 and reload socket cap 94, reload catch 96 is compressed until the catch 96 passes in the notch 95. The catch 96 expands into the notch 95, and holds the reload anchor housing in place against the reload socket base 93 and reload socket cap 94. The reloaded device is now ready for a suture to be passed through the eyelet of the secondary anchor 80, to prepare for deployment.

Figure 17B:
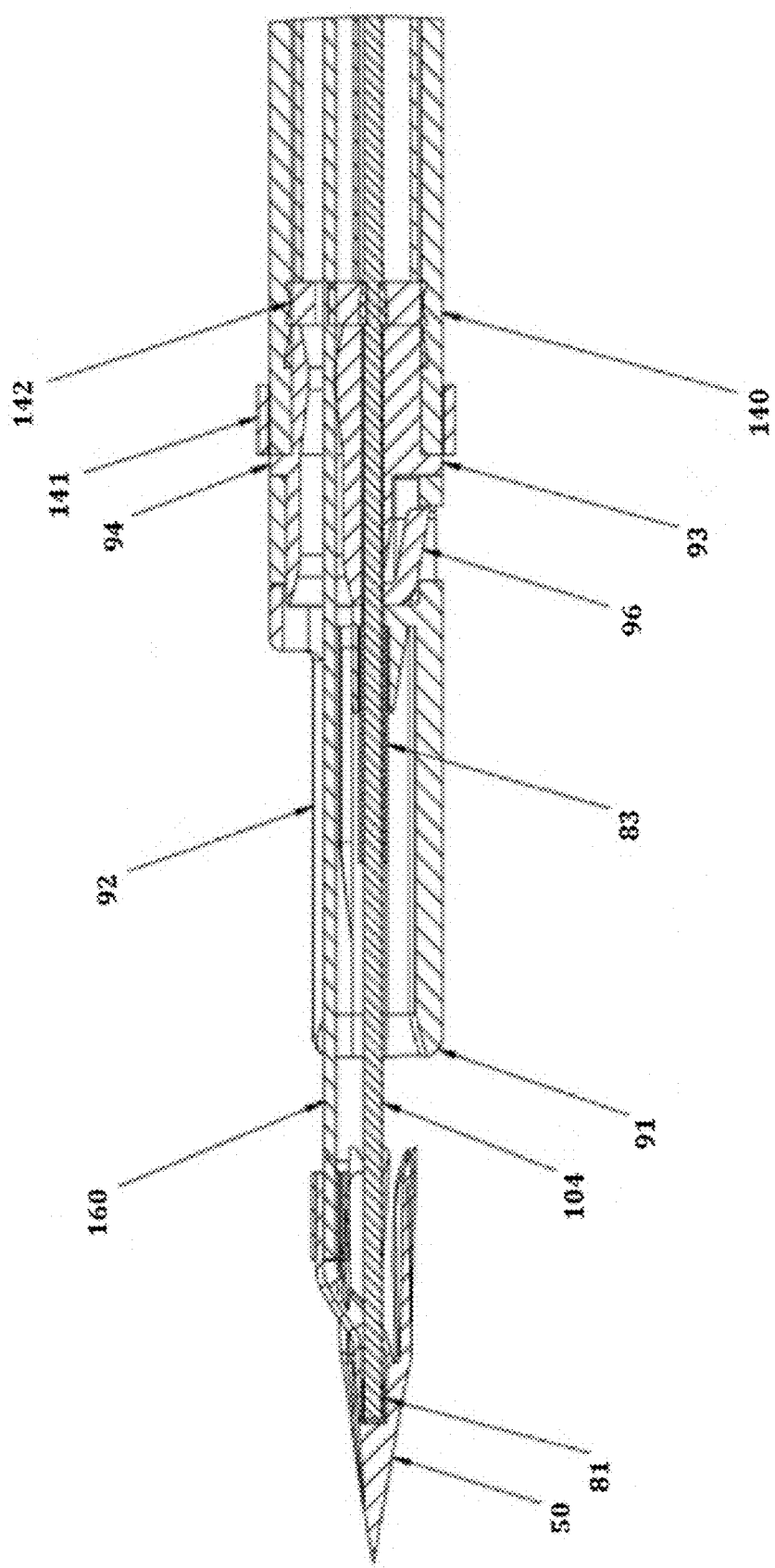
FIG. 17B shows a cross sectional view of the anchor deployment mechanism in accordance with an example embodiment of the present invention.
Figure 17C:
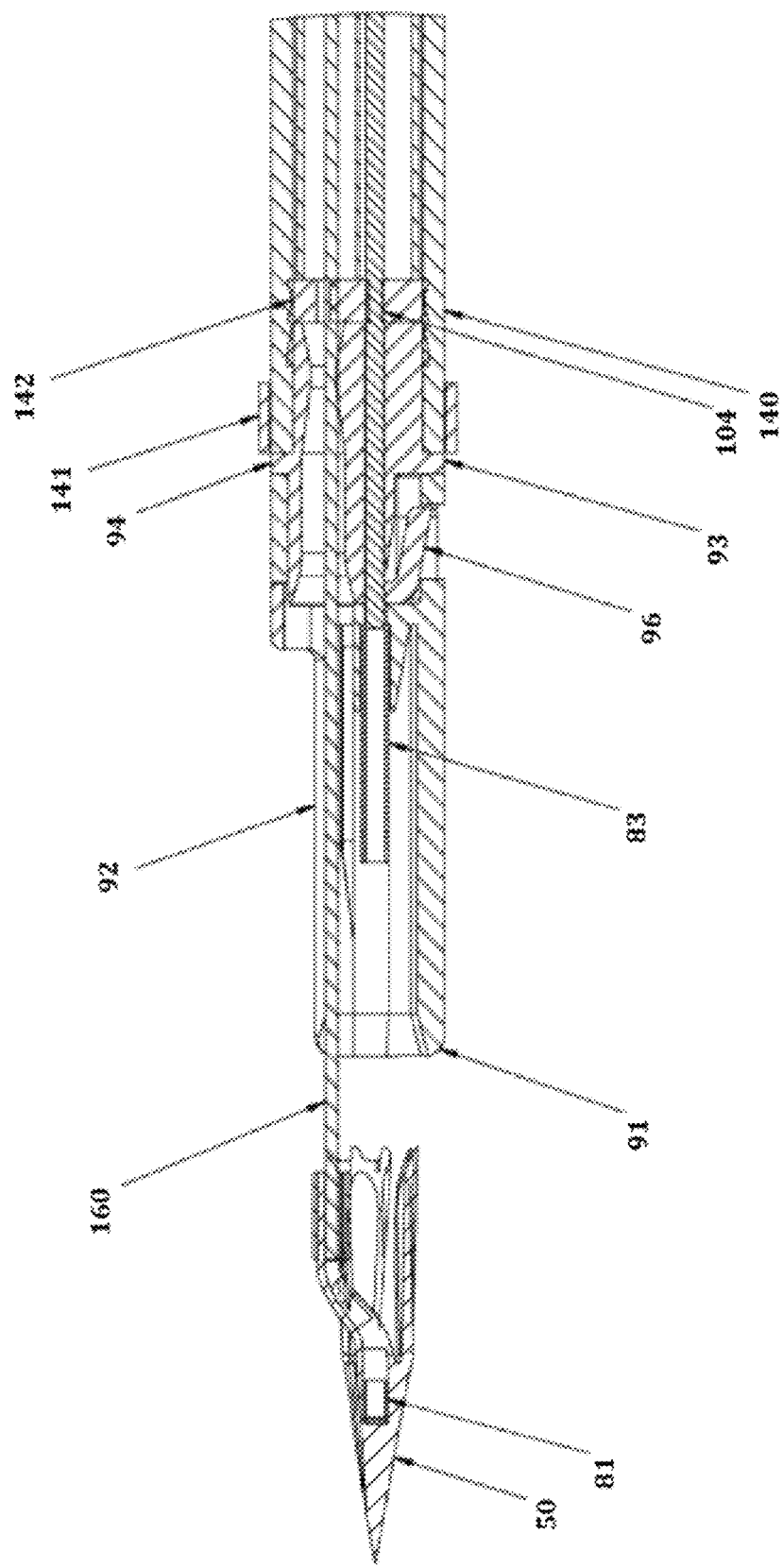
FIG. 17C shows a cross sectional view of the anchor deployment mechanism in accordance with an example embodiment of the present invention.
Figure 17D:
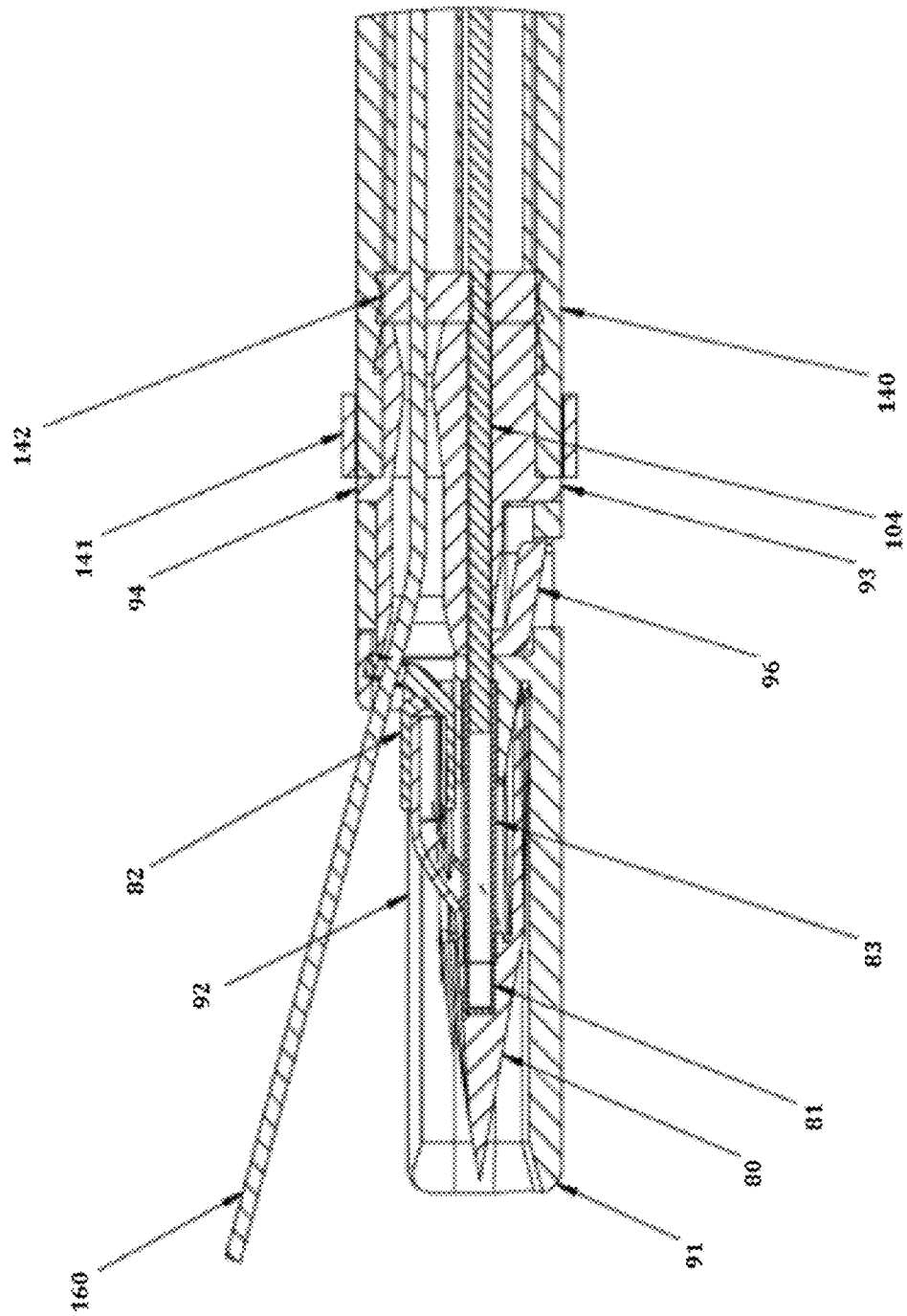
FIG. 17D shows a cross sectional view of the anchor deployment mechanism in accordance with an example embodiment of the present invention.
Figure 17E:
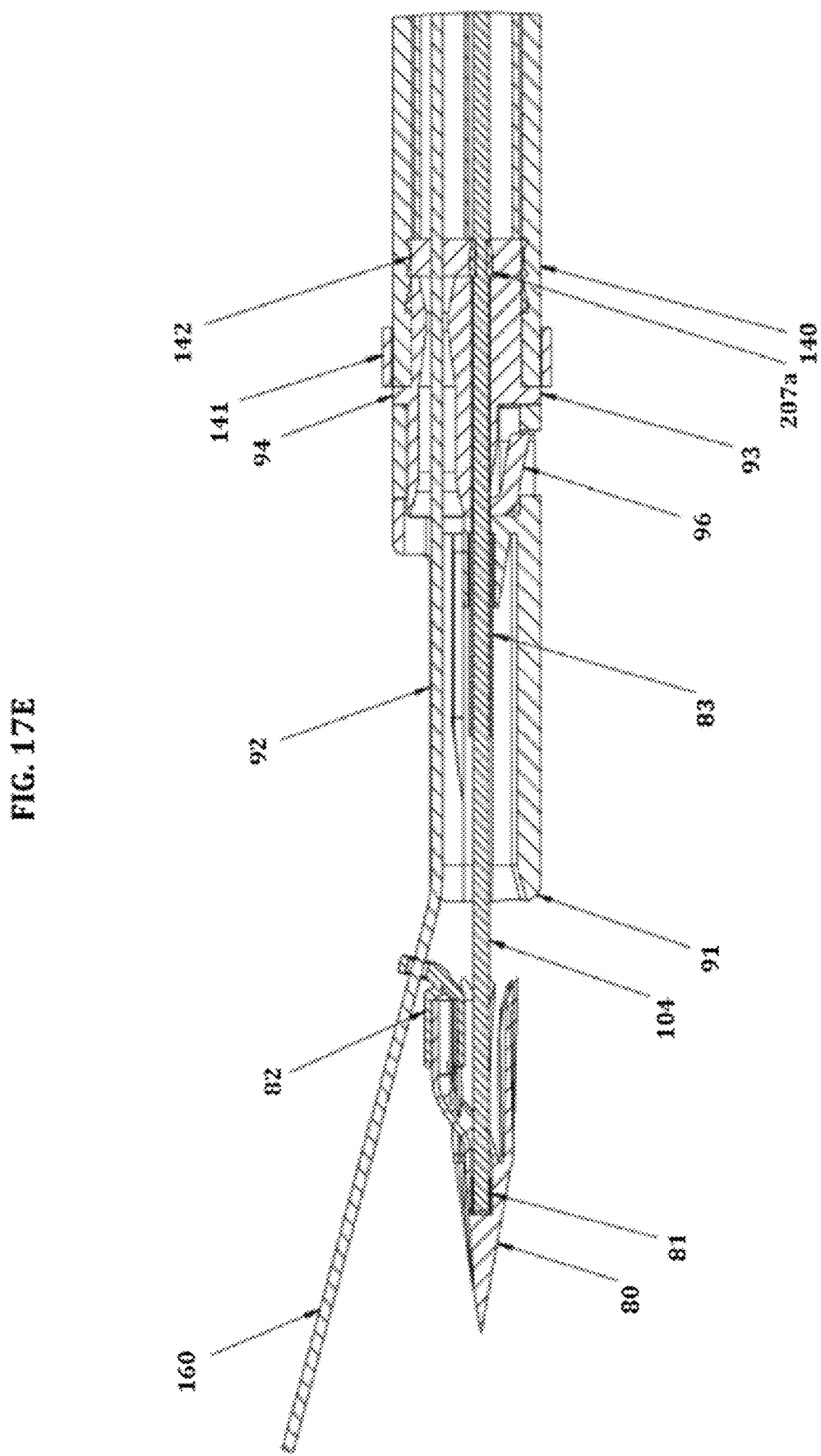
FIG. 17E shows a cross sectional view of the anchor deployment mechanism in accordance with an example embodiment of the present invention.
Figure 17F:
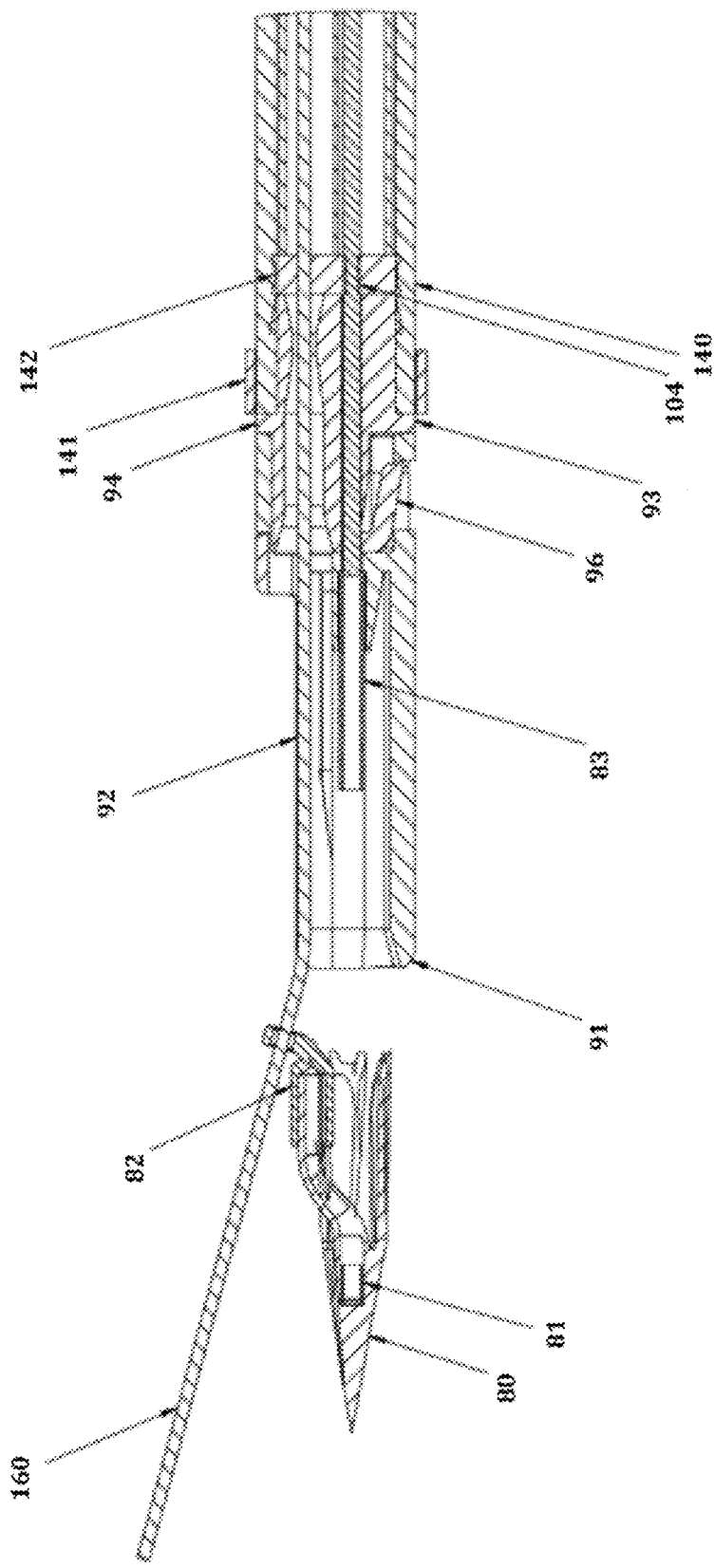
FIG. 17F shows a cross sectional view of the anchor deployment mechanism in accordance with an example embodiment of the present invention.

FIGS. 17A-17F illustrates the distal end of the surgical device through deployment of a primary anchor, and then deployment of a secondary anchor, according to an exemplary embodiment. FIG. 17A shows primary anchor 50, situated within reload anchor housing 90, connected to suture 160, with pusher wire 104 prepared to deploy the anchor. FIG. 17B shows pusher wire 104 extended beyond the distal end of the surgical device, to deploy the primary anchor 50 and the distal end of suture 160 into tissue (not shown). In FIG. 17C, anchor 50 has been deployed, and pusher wire 104 has been retracted. At this stage, the surgical device may be removed from the surgical site, and reload anchor housing 90 may be released from the distal end of the surgical device, by compressing reload catch 96 within notch 95. As described in the above FIGS. 16A, 16B, and 16C, another reload anchor housing 90 may be installed, including a secondary anchor 80. As described in the above FIG. 6A or 6B, suture 160 may be passed through the anchor eyelet 82 and into the catheter. Then, as shown in FIG. 17D, the secondary anchor 80 is ready for deployment. FIG. 17E shows pusher wire 104 extended beyond the distal end of the surgical device, to deploy the secondary anchor 80 and the associated portion of suture 160 into tissue (not shown). In FIG. 17F, secondary anchor 80 has been deployed, and pusher wire 104 has been retracted. The device is now ready for an additional component, for example, an additional secondary anchor, or a cutting and locking mechanism as described herein, to be attached to the deployed suture and used to complete the surgical procedure.

Figure 18B:
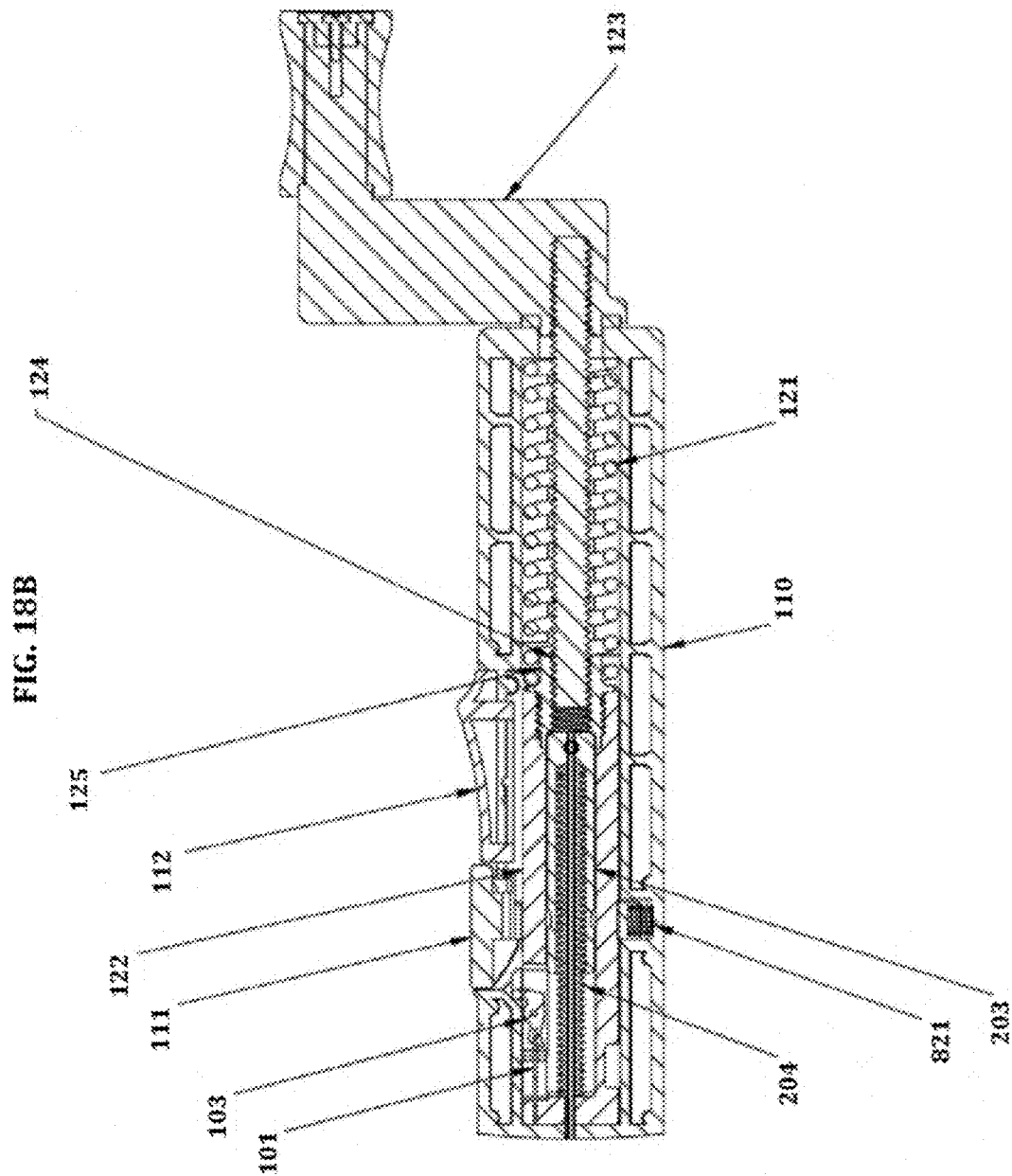
FIG. 18B shows a cross sectional view of the anchor deployment mechanism in accordance with an example embodiment of the present invention.
Figure 18C:
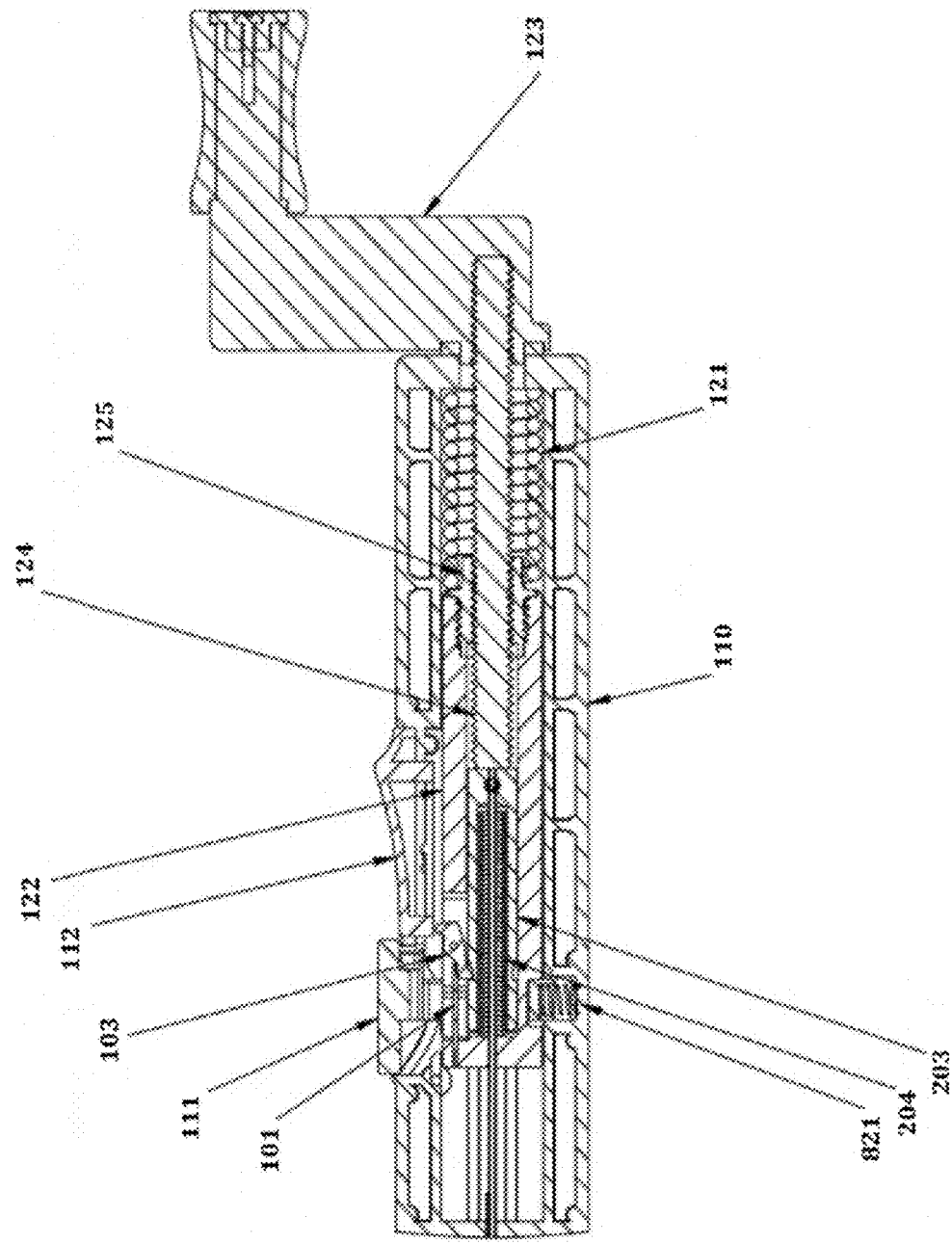
FIG. 18C shows a cross sectional view of the anchor deployment mechanism in accordance with an example embodiment of the present invention.

In an exemplary embodiment of the present invention, to deploy a secondary anchor after the deployment of a primary anchor, the driving mechanism must be re-armed, or otherwise re-set to a pre-firing position. FIGS. 18A, 18B, and 18C illustrate this re-arming in an exemplary embodiment of the present invention, for a spring-based driving mechanism. FIG. 18A shows a handle for an anchor deployment mechanism, similar to the anchor deployment mechanism shown in FIG. 1B. As in FIG. 1B, the handle 110 of FIG. 18A includes elements configured to impart a pushing force on anchors located in the distal anchor housing (not shown), including release button 111, pawl 103, tensioned spring 121, pawl spring 101, pin retractor spring 204, and pin retractor 203. In FIG. 18A, the tension of spring 121 has already been released, having exerted its pushing force. To re-arm the handle 110, crank 123 may be introduced, including a threaded shaft 124. Handle 110 may include a threaded pusher cap 125, situated between, and attached to, the pusher 122 and the spring 121. As shown in FIGS. 18B and 18C, shaft 124 of crank 123 may be inserted into the proximal end of handle 110, to be threaded into pusher cap 125. As the crank 123 is rotated, pusher cap 125 is drawn in the proximal direction, compressing the spring 121. As the spring 121 is compressed, and the pusher is moved in the proximal direction, the release button 111 is reset into a notch in the pusher 122 from pressure exerted by the release button spring 821. The safety button 112 may be reset manually. The spring 121 is now re-tensioned, and the device is re-armed for the next deployment. It should be noted that pin retractor 203 is held axially stationary by the end of the threaded shaft 124. When the pusher 122 is drawn fully proximal, the pin retraction spring 204 is compressed, and the pawl 103 re-engages with the groove in the pin retractor 203, resetting the pin retraction mechanism.

Figure 19A:
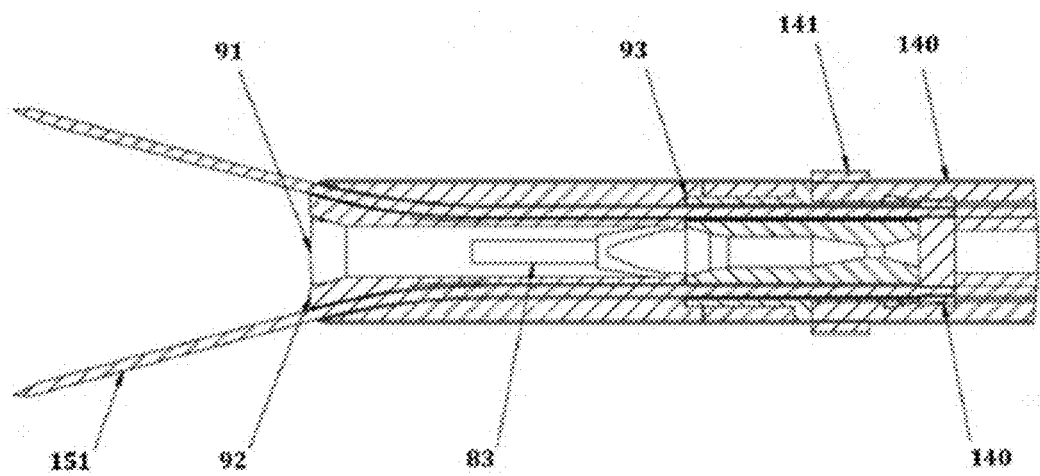
FIG. 19A shows a cross sectional view of the anchor deployment mechanism in accordance with an example embodiment of the present invention.
Figure 19B:
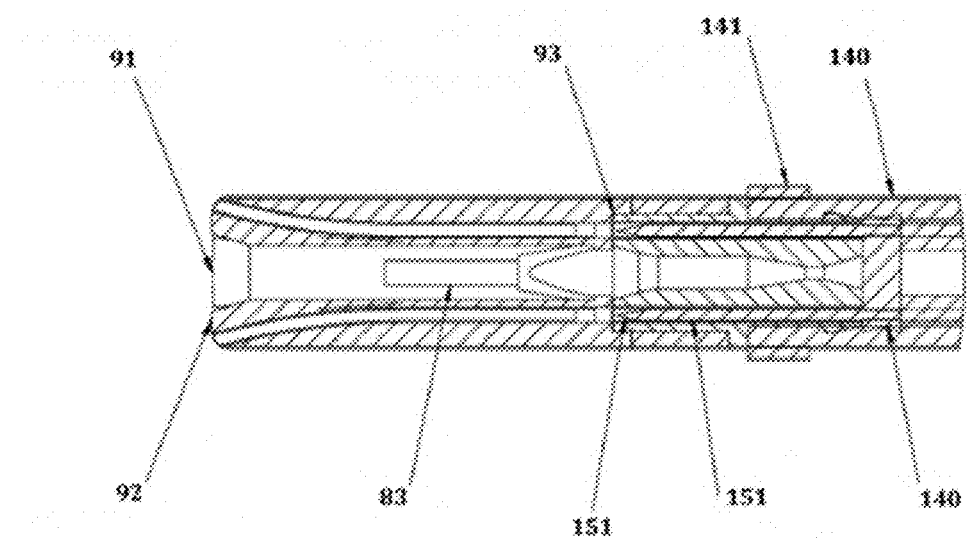
FIG. 19B shows a cross sectional view of the anchor deployment mechanism in accordance with an example embodiment of the present invention.

FIGS. 19A and 19B illustrate the retraction of the stabilization pins more fully described above in connection with FIGS. 2A-2D. In the context of a detachable reload anchor housing, FIGS. 19A and 19B show that the stabilization pins 151 may be sufficiently retracted to a position proximal to the reload anchor housing (as shown in FIG. 19B), so that the stabilization pins do not interfere with the detachment of the reload anchor housing.

Figure 20A:
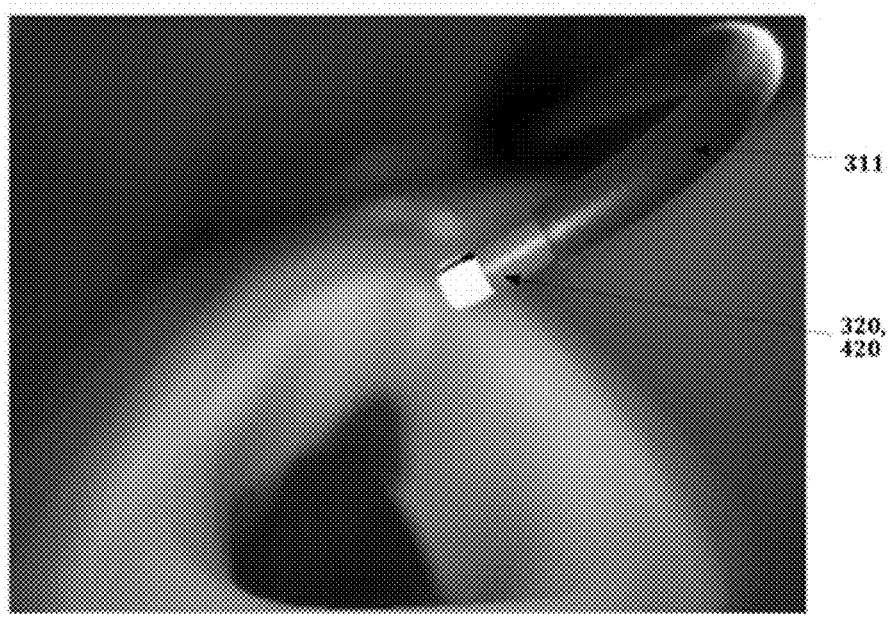
FIG. 20A shows a distal housing of the anchor deployment mechanism in accordance with an example embodiment of the present invention.
Figure 20B:
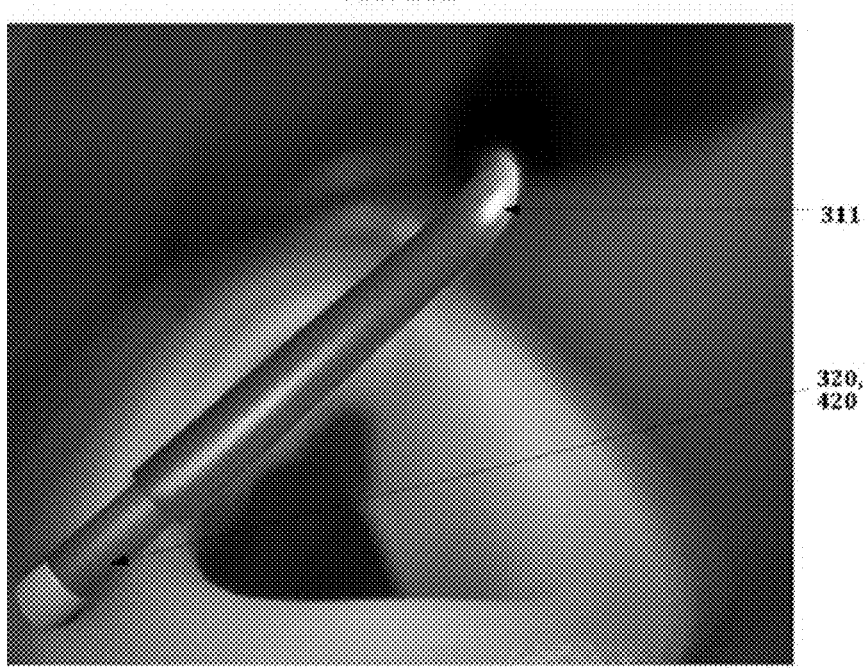
FIG. 20B shows a distal housing of the anchor deployment mechanism in accordance with an example embodiment of the present invention.
Figure 20C:
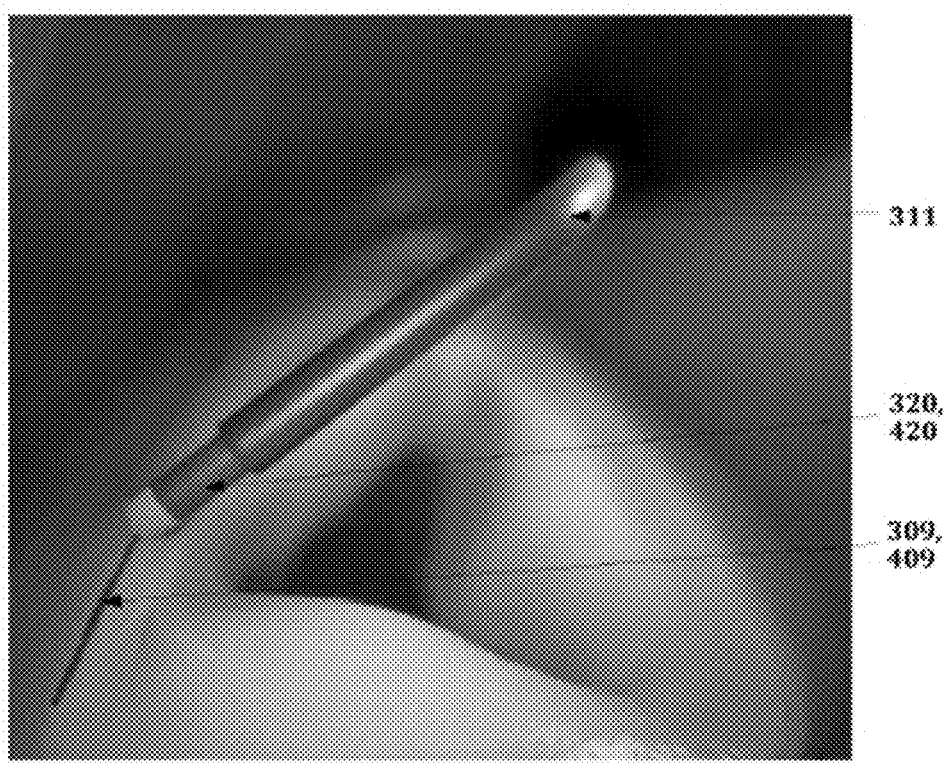
FIG. 20C shows a distal housing of the anchor deployment mechanism in accordance with an example embodiment of the present invention.
Figure 20D:
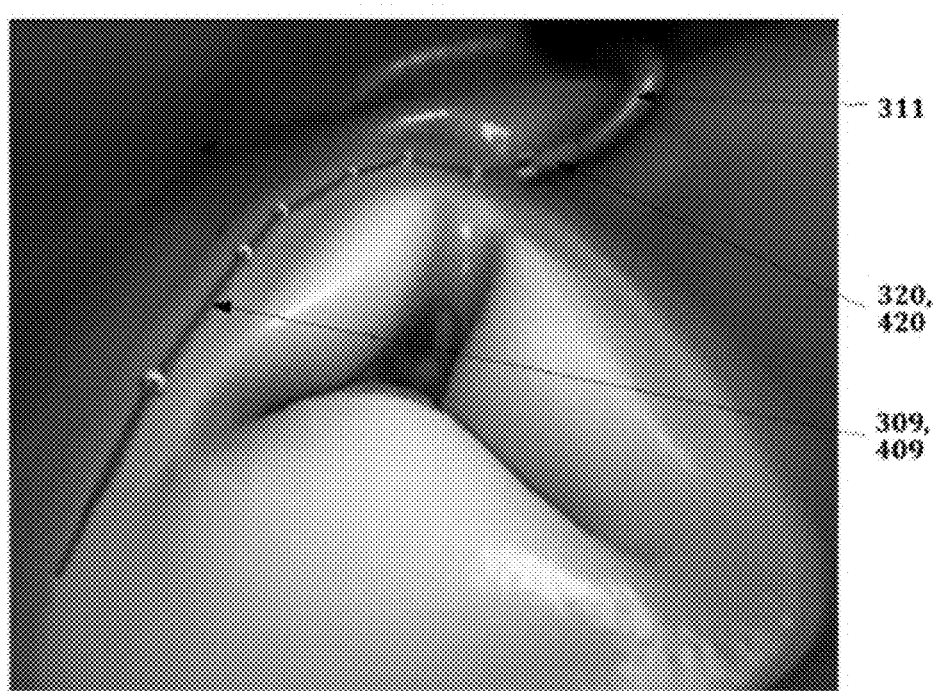
FIG. 20D shows a distal housing of the anchor deployment mechanism in accordance with an example embodiment of the present invention.
Figure 20E:
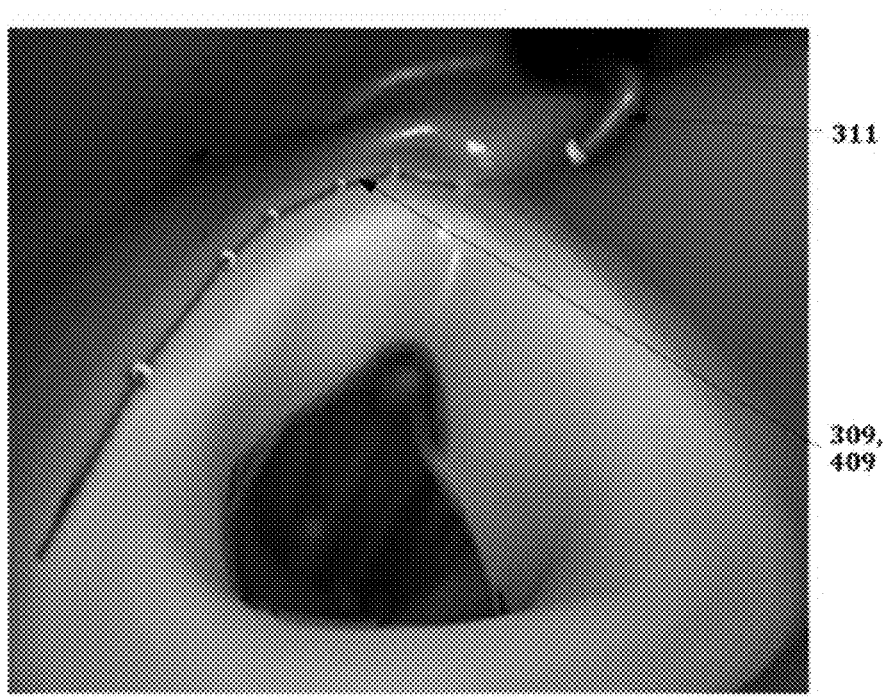
FIG. 20E shows a distal housing of the anchor deployment mechanism in accordance with an example embodiment of the present invention.
Figure 20F:
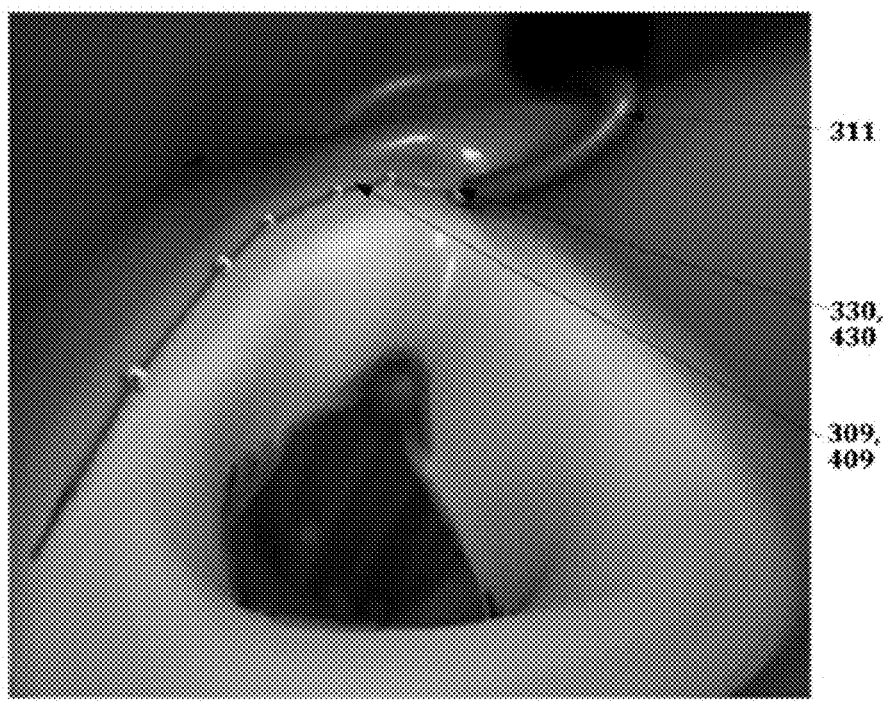
FIG. 20F shows a distal housing of the anchor deployment mechanism in accordance with an example embodiment of the present invention.
Figure 20G:
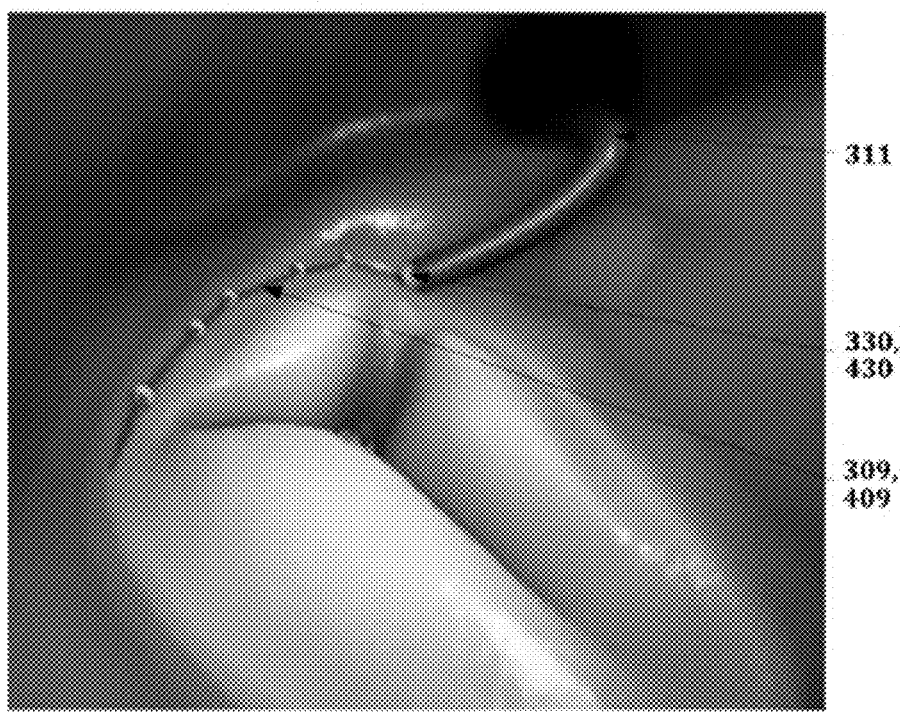
FIG. 20G shows a distal housing of the suture locking mechanism in accordance with an example embodiment of the present invention.
Figure 20H:
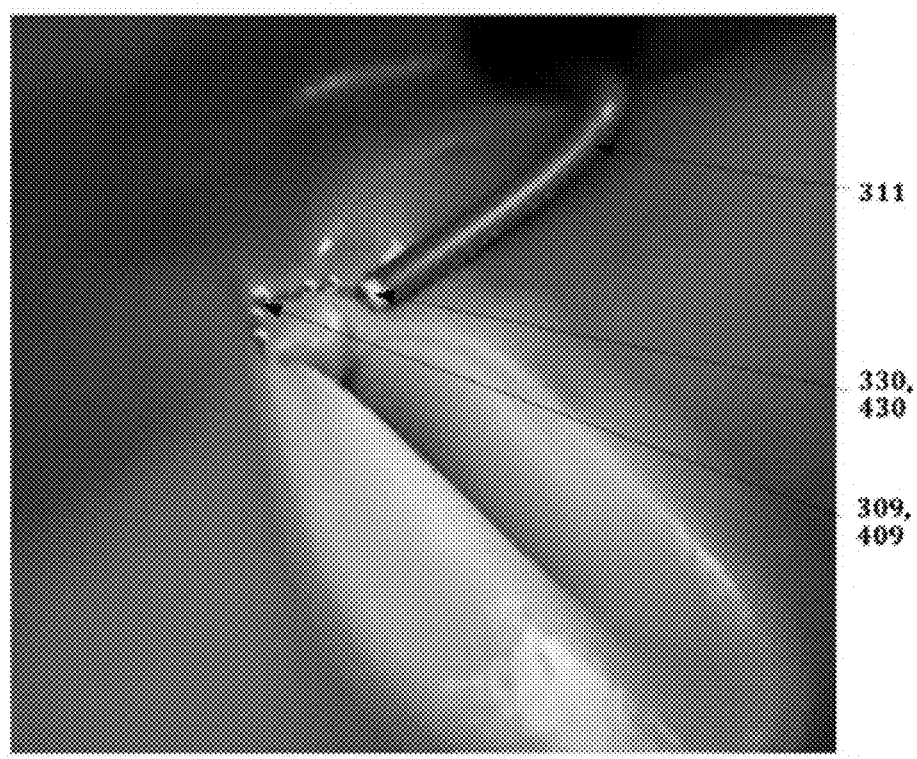
FIG. 20H shows a distal housing of the suture locking mechanism in accordance with an example embodiment of the present invention.
Figure 20I:
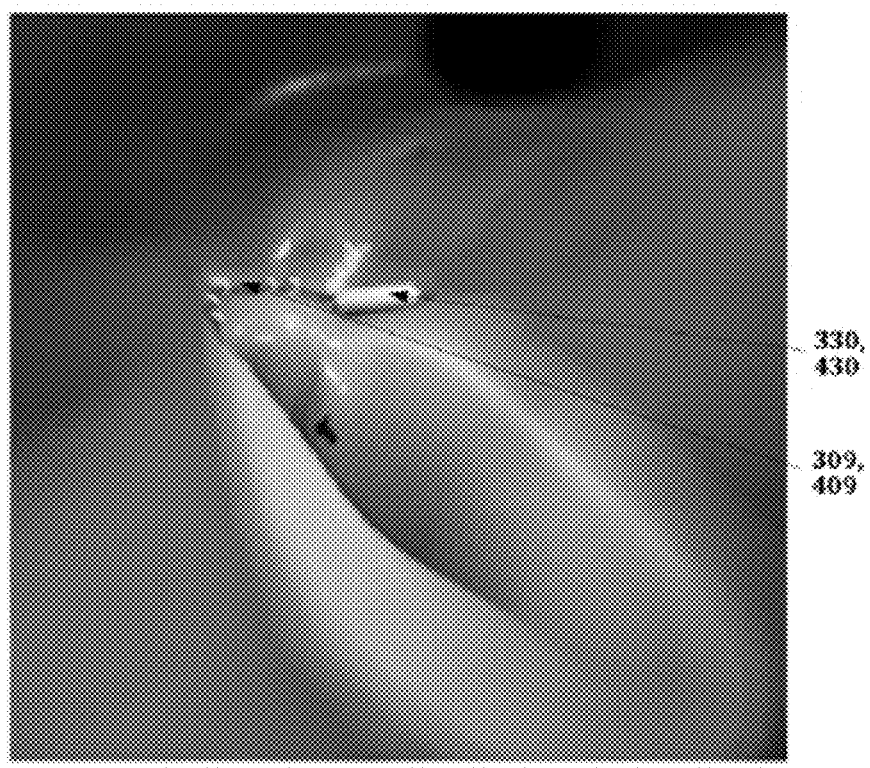
FIG. 20I shows a suture lock of the anchor deployment mechanism in accordance with an example embodiment of the present invention.

According to exemplary embodiments of the present invention, the surgical device described herein may be used to deploy a series of anchors along a suture, and draw the suture to bring the anchors into apposition around a valve. FIG. 20A illustrates a damaged valve, as a catheter sheath 311 is moved into position around the surgical site, the catheter sheath 311 containing catheter 310 or 410. A distal housing 320 or 420 is extended beyond the catheter sheath 311. In FIG. 20B, the distal housing 320 or 420 has been positioned against the tissue, in preparation for deploying an anchor into the tissue. The stabilization pins described herein may be used in this regard, to ensure that the distal housing 320 or 420 is in proper position with respect to the tissue before deployment of anchors. In FIG. 20C, a primary anchor has already been deployed into tissue, and a secondary anchor is being deployed in another tissue site, with a suture 309 or 409 connecting the two anchors. In FIG. 20D, a series of secondary anchors has been deployed along the suture 309 or 409. In FIG. 20E, the distal housing 320 or 420 is retracted as the anchor deployment mechanisms are switched for the locking and cutting mechanisms. In FIGS. 20F, 20G, and 20H, the suture 309 or 409 is drawn proximally into the catheter, pulling on the primary anchor and drawing the series of anchors into apposition, and in turn tightening the tissue surrounding the valve. Further, in FIG. 20H, the locking and cutting procedure is applied as discussed herein, to close the suture locking housing 330 or 430 on the suture 309 or 409, to cut the suture 309 or 409, and to separate the cut portion of the suture from the portion of the suture contained in the catheter. In FIG. 20I, the entire implant, including the anchors, suture, and suture locking housing remains, to maintain the position of the suture and the anchors in holding the tissue, the valve now being restructured to allow the leaflets to properly coapt.

Modern manufacturing processes allow for highly precise component features at previously unattainable scale. The anchors 30, 40, 50, 70, and 80 may have a diameter of, e.g., one millimeter, or approximately one millimeter, and a length that is in a range from, e.g., 5 millimeters to 10 millimeters. According to some example embodiments, the diameter is less than one millimeter. According to some example embodiments, the diameter is in a range from 0.8 millimeters to 1.2 millimeters. It should be understood, however, that other dimensions may be provided.

Further, the anchors 30, 40, 50, 70 and 80 are driven at an optimal speed, such that the anchor has sufficient velocity to overcome the surface tension of the tissue and penetrate the tissue, without displacing it. Sufficient deployment speeds allow the anchor to maintain a necessary rigidity to pierce tissue during deployment. In exemplary embodiments, such speeds may be up to 300 meters per second. However, it should be understood that the anchors may be driven at any suitable speed sufficient for the anchors to puncture tissue.

Further, the anchors 30, 40, 50, 70, and 80 may be driven into a single layer or multiple layers of tissue and that the speed may be selected based on the structural properties, dimensions, and relative locations of the one or more tissues into which the anchors are driven.

To accurately penetrate soft tissues that are not held or secured on a distal side, a rapid penetration of each layer of tissue may be required to effect penetration of the tissue layer or layers. If an anchor is applied slowly, the tissue or tissues may be pushed distally away by the anchor without adequate penetration. Thus, some example delivery mechanisms eject each anchor at a relatively high speed, as set forth above. Although the deployment mechanisms 100, 200, 300, 400, 450, and 500 may utilize a spring-loaded mechanical driving mechanism, it should be understood that other drivers may be provided. In some examples, saline is used to pressurize a channel within a catheter, needle, or other tube at such a rate that a plunger will eject the anchor at the precise speed. Further example embodiments push the anchors 30, 40, 50, 70, and 80 using long push rods which run the length of a catheter or other tube. The ejection modality may be computer-controlled and/or operator-controlled. For example, as with the spring loaded mechanical system of the illustrated examples, an ejection force may be predetermined and repeatable by an operator's actuation of a trigger.

Moreover, the driver may be configured to drive the anchors 30, 40, 50, 70, and 80 to a predetermined depth. In an example embodiment, the precision of the depth may be accomplished by a precise hydraulic driving force, engagement with other stops, or a suture that tautens to limit the depth. Further, the depth may be monitored using fluoroscopy, echocardiography, intravascular ultrasound or any other appropriate imaging mechanism. The driving mechanism may include pressurized saline or other hydraulic fluid that is pressurized through the thoracoscopic catheter shaft. Thus, very precise control may be accomplished.

The piercing of the tissue may provide access to the opposed side of the tissue (e.g., the interior of a viscus such as the heart, etc.) by thoracoscopic or other surgical and interventional instruments including guide wires and catheters.

Further, in an example embodiment, any of the anchors 30, 40, 50, 70, and 80 could be utilized with any of deployment mechanisms 100, 200, 300, 400, 450, and 500 of the present invention.

Further, the anchors 30, 40, 50, 70, and 80 may be driven after forming the aperture. Similarly, it is feasible to drive the anchors 30, 40, 50, 70, and 80 prior to dilating the hole.

Further, it should be understood that the deployment mechanisms 100, 200, 300, 400, 450, and 500 may be provided in connection with any appropriate surgical device, e.g., a catheter or flexible thoracoscopic shaft. Moreover, any appropriate driving mechanism for driving the anchors 30, 40, 50, 70, and 80 may be provided.

Further, although the sutures 60, 160, 309, and 409 are each formed as a single monolithic piece, it should be understood that any suture described herein may be comprised of multiple component pieces.

Moreover, although the examples described herein are described as firing a plurality of anchors that are each identical to each other, it should be understood that a driven set of anchors may include one or more anchors that differ from the other anchors of the set. For example, situations with non-uniform tissue properties and/or dimensions may be addressed by firing, e.g., simultaneously, different types of anchors at different locations. In this regard, the deployment mechanisms 100, 200, 300, 400, 450, and 500 may be adapted to receive different types of anchors in the same slot and/or have interchangeable housing portions to receive the various anchors.

Further, any of the implantable elements described herein, e.g., anchors 30, 40, 50, 70, and 80 and/or sutures 60, 160, 309, and 409 may be formed wholly or partly of a material absorbable into the patient's body, or of a non-absorbable material, depending on, e.g., the specific application. For example, these elements may be formed of polyglycolic acid (PGA), or a PGA copolymer. These elements may also, or alternatively, be formed of copolymers of polyester and/or nylon and/or other polymer(s). Moreover, these elements may contain one or more shape-memory alloys, e.g., nitinol, spring-loaded steel, or other alloy or material with appropriate properties. Additionally, biologics, e.g. Fibrin, may be utilized to enable tissue ingrowth.

Absorbable materials may be advantageous where there is a potential for misfiring or improper locating of the various implants. For example, in a situation where the driver drives an anchor 30, 40, 50, 70, and 80 at an unintended location, or where the tissue does not properly receive the implant, the implant even where not needed, would be relatively harmless, as it would eventually absorb into the patient's body.

Although particular example surgical applications have been described above, the deployment mechanisms 100, 200, 300, 400, 450, and 500 are in no way limited to these examples.

Although the present invention has been described with reference to particular examples and exemplary embodiments, it should be understood that the foregoing description is in no manner limiting. Moreover, the features described herein may be used in any combination.

What is claimed is:

1. An apparatus for deploying a tissue anchor comprising:
   a catheter tube having a proximal end and a distal end defining the catheter's length, wherein the distal end comprising an anchor housing configured to hold a tissue anchor before deployment; and
   a pusher wire positioned within the catheter tube and extending through the length of the catheter tube, wherein the pusher wire has a proximal end and a distal end corresponding with the proximal end and the distal end of the catheter tube,
   wherein the apparatus is configured to provide a pushing force on the pusher wire from the proximal end of the catheter tube, thus displacing the pusher wire in a distal direction to the pusher wire's fully extended anchor deployment position which in turn deploys the tissue anchor from the anchor housing in the distal direction by pushing the tissue anchor in the distal direction so that the tissue anchor can penetrate a target tissue, and
   one or more stabilization pins extending through the length of the catheter and through corresponding passageways provided in the anchor housing, wherein the stabilization pins are configured to be manipulated from the proximal end of the catheter tube to be moved between a retracted position in which the stabilization pins do not extend out of the anchor housing, and an extended position in which the stabilization pins are in their extended position extending out of the anchor housing;
   wherein the apparatus is configured to electrically bias the stabilization pins so that electrical current passes between the stabilization pins through the target tissue when the distal end of the distal anchor housing is pressed against or into the target tissue, thus providing a feedback that the apparatus is in a proper position against the target tissue.

2. The apparatus of claim 1, wherein each of the stabilization pins has a distal end and a proximal end, and each of the stabilization pins comprising a stabilization pin stop provided at a fixed distance form the distal end of the stabilization pin, wherein the stabilization pin stop prevents the stabilization pin from extending beyond a preset distance by interfering with the proximal end of the anchor housing.

3. The apparatus of claim 1, wherein the stabilization pins are radiopaque.

4. The apparatus of claim 1, wherein the stabilization pins are configured to extend distally form the center line of the anchor housing at an angle of 5°-20°.

5. The apparatus of claim 1, further comprising:
   a pusher carriage attached to the proximal end of the pusher wire and configured to travel linearly within the handle between a first position and a second position,
   a pin retractor provided within the pusher carriage and attached to the proximal end of the pusher wire,
   wherein the pin retractor is configured to travel linearly within the pusher carriage between a first position and a second position,
   wherein, in the first position, the pin retractor is in its locked position with respect to the pusher carriage which is most-distal position within the pusher carriage, and in the second position, the pin retractor is in its unlocked position with respect to the pushed carriage which is most-proximal position within the pusher carriage; and a pin retractor spring positioned within the pushed carriage and arranged to provide a force constantly urging the pin retractor toward the pin retractor's second position, wherein when the pusher carriage is in its first position, the pin retractor is in its first position and the pusher wire is in its retracted position, and when the pusher carriage reaches the pusher carriage's second position which corresponds to the pusher wire's fully extended anchor deployment position, the pin retractor transitions into its second position whereby retracting the pusher wire from the fully extended anchor deployment position to a retracted position.

\* \* \* \* \*